(12) United States Patent
Shao et al.

(10) Patent No.: US 6,716,604 B2
(45) Date of Patent: Apr. 6, 2004

(54) NUCLEIC ACID MOLECULES ENCODING A SUBUNIT OF A HUMAN CALCIUM/CALMODULIN-DEPENDENT PROTEIN KINASE

(75) Inventors: Wei Shao, Frederick, MD (US); Gennady V. Merkulov, Baltimore, MD (US); Valentina Di Francesco, Rockville, MD (US); Ellen M. Beasley, Darnestown, MD (US)

(73) Assignee: Applera Corporation, Norwalk (NO)

( * ) Notice: Subject to any disclaimer, the term of this patent is extended or adjusted under 35 U.S.C. 154(b) by 453 days.

(21) Appl. No.: 09/820,790

(22) Filed: Mar. 30, 2001

(65) Prior Publication Data

US 2003/0140354 A1 Jul. 24, 2003

(51) Int. Cl.$^7$ .................. C12N 15/52; C12N 15/54; C12N 15/67; C12N 15/12
(52) U.S. Cl. .................. 435/69.2; 435/69.1; 435/252.3; 435/254.11; 435/320.1; 435/325; 435/410; 435/455; 435/456; 435/468; 435/471; 536/23.1; 536/23.2; 536/23.5
(58) Field of Search .................. 435/69.1, 69.2, 435/252.3, 254.11, 320.1, 325, 410, 455, 456, 468, 471; 536/23.1, 23.2, 23.5

(56) References Cited

PUBLICATIONS

Karls et al. "Structure, Expression, and Chromosome Location of the Gene for the Beta Subunit of Brain–Specific Ca2+/Calmodulin–dependent Protein Kinase II Identified by Trangene integration in an Embryonic Lethal Mouse Mutant" Molecular and Cellular Biology. Aug. 1992, vol. 12, No. 8, pp. 3644–3652.

Bennet et al. Deduced Primary Structure of the Beta Subunit of Brain Type II Ca2+/Calmodulin–Dependent Protein Kinase Determined by Molecular Cloning. Proceedings of the National Academy of Sciences. USA. Apr. 1987. vol. 84, Pages.

Urquidi et al. "A Novel Pancreatic Beta–Cell Isoform of the Calcium/Calmodulin–dependent Protein Kinase II (Beta3 isoform) Contains a Proline–rich Tandem Repoeat in the Association Domain." FEBS Letters. 1995. vol. 358, pp. 23–26.

Li et al. "Molecular Cloning and Analysis of a Ca2+/Calmodulin–Dependent Protein Kinase II from the Chicken Broth." Journal of Molecular Neuroscience. 1998. vol. 11, No. 2, pp. 135–139.

Li et al. "Gallus Gallus Calcium/Calmodulin–dependent Kinase Type II Beta Subunit mRNA, Complete cds." Database GenBank, US National Library of Medicine, No. AF085249. Sep. 30, 1998.

Wang et al. "Identification of Alternative Splicing Variants of the Beta Subunit of Human Ca2+/Calmodulin–dependent Protein Kinase II with Different Activities." FEBS Letters. Jun. 16, 2000. vol. 475, No. 2, pp. 107–110.

Zhou et al. "Homo Sapiens Calcium/Calmodulin Dependent Kinase Type II Beta 6 Subunit (CAMKB) mRNA, Complete cds." Database GenBank, US National Library of Medicine No. AF081924. Jul. 2, 1999.

Zhou et al. "Homo Sapiens Calcium/Calmodulin Dependent Kinase Type II Beta Subunit mRNA, Complete cds." Database GenBank, US National Library of Medicine, No. AF078803. Jul. 2, 1999.

Waterson et al. "Homo Sapiens PAC Clone RP5–852P6 from 7p11.2–p21, Complete Sequence." Database GenBank, US National Library of Medicine, No. AC006454. Sep. 30, 2000.

Braun et al. "The Multifunctional Calcium/Calmodulin–dependent Protein Kinase: From form to Function." Annual Review of Physiology. 1995, vol. 57, pp. 417–445.

Soderling et al. Structure and Regulation of Calcium/Calmodulin–dependent Protein Kinases. Chemical Reviews. Aug. 2001. vol. 101, No. 8, pp. 2341–2352.

International Search Report dated Dec. 23, 2002.

Results of BLAST search of SEQ ID NO:2 against Derwent (FastAlert and GeneSeqP) and NCBI (pataa) protein patent databases on Jul. 23, 2003.

*Primary Examiner*—Scott D. Priebe
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

17 Claims, 23 Drawing Sheets

```
   1 CGGGCGCGGC GGCGGCGGCG GTGACAGCGG CGCCCGCGCC TCCCCGCGCG
  51 TAGGTGTGCG GCGCGCTCCT GGCGAGGACG GAGCGAGCAG ATCTCGCGTG
 101 CGCTCGCCGC CCGGCGCAGC CCAGCCCGGC CCCCGCCTGG CGCCGCGAGC
 151 CGAGGTGTCT CCCGCGCCCG CGCCCGTGTC GCCGCCGTGC CCGCGAGCGG
 201 GAGCCGGAGT CGCCGCCGCC CGAGCGCAGC CGAGCGCACG CCGAGCCCGT
 251 CCGCCGCCGC CATGGCCACC ACGGTGACCT GCACCCGCTT CACCGACGAG
 301 TACCAGCTCT ACGAGGATAT TGGCAAGGGG GCTTTCTCTG TGGTCCGACG
 351 CTGTGTCAAG CTCTGCACCG GCCATGAGTA TGCAGCCAAG ATCATCAACA
 401 CCAAGAAGCT GTCAGCCAGA GATCACCAGA AGCTGGAGAG AGAGGCTCGG
 451 ATCTGCCGCC TTCTGAAGCA TTCCAACATC GTGCGTCTCC ACGACAGCAT
 501 CTCCGAGGAG GGCTTCCACT ACCTGGTCTT CGATCTGGTC ACTGGTGGGG
 551 AGCTCTTTGA AGACATTGTG GCGAGAGAGT ACTACAGCGA GGCTGATGCC
 601 AGTCACTGTA TCCAGCAGAT CCTGGAGGCC GTTCTCCATT GTCACCAAAT
 651 GGGGGTCGTC CACAGAGACC TCAAGCCGGA GAACCTGCTT CTGGCCAGCA
 701 AGTGCAAAGG GGCTGCAGTG AAGCTGGCAG ACTTCGGCCT AGCTATCGAG
 751 GTGCAGGGGG ACCAGCAGGC ATGGTTTGGT TTCGCTGGCA CACCAGGCTA
 801 CCTGTCCCCT GAGGTCCTTC GCAAAGAGGC GTATGGCAAG CCTGTGGACA
 851 TCTGGGCATG TGGGGTGATC CTGTACATCC TGCTCGTGGG CTACCCACCC
 901 TTCTGGGACG AGGACCAGCA CAAGCTGTAC CAGCAGATCA AGGCTGGTGC
 951 CTATGACTTC CCGTCCCCTG AGTGGGACAC CGTCACTCCT GAAGCCAAAA
1001 ACCTCATCAA CCAGATGCTG ACCATCAACC CTGCCAAGCG CATCACAGCC
1051 CATGAGGCCC TGAAGCACCC GTGGGTCTGC CAACGCTCCA CGGTAGCATC
1101 CATGATGCAC AGACAGGAGA CTGTGGAGTG TCTGAAAAAG TTCAATGCCA
1151 GGAGAAAGCT CAAGGGAGCC ATCCTCACCA CCATGCTGGC CACACGGAAT
1201 TTCTCAGTGG GCAGACAGAC CACCGCTCCG GCCACAATGT CCACCGCGGC
1251 CTCCGGCACC ACCATGGGGC TGGTGGAACA AGCCAAGAGT TTACTCAACA
1301 AGAAAGCAGA TGGAGTCAAG CCCCAGACGA ATAGCACCAA AAACAGTGCA
1351 GCCGCCACCA GCCCCAAAGG GACGCTTCCT CCTGCCGCCC TGGAGCCTCA
1401 AACCACCGTC ATCCATAACC CAGTGGACGG GATTAAGGAG TCTTCTGACA
1451 GTGCCAATAC CACCATAGAG GATGAAGACG CTAAAGCCCG GAAGCAGGAG
1501 ATCATTAAGA CCACGGAGCA GCTCATCGAG GCCGTCAACA ACGGTGACTT
1551 TGAGGCCTAC GCATTCTACT TCGAGAACCT GCTGGCCAAG AACAGCAAGC
1601 CGATCCACAC GACCATCCTG AACCCACACG TGCACGTCAT TGGAGAGGAT
1651 GCCGCCTGCA TCGCTTACAT CCGGCTCACG CAGTACATTG ACGGGCAGGG
1701 CCGGCCCCGC ACCAGCCAGT CTGAGGAGAC CCGCGTGTGG CACCGCCGCG
1751 ACGGCAAGTG GCAGAACGTG CACTTCCACT GCTCGGGCGC GCCTGTGGCC
1801 CCGCTGCAGT GAAGCCAAGG GAGGGGCACA GAATGGGGAA CAGGACACAG
1851 GATCCTAAAC TCCAAGGGGA CTGTCCACCG ATGAACACTC AGAGTGGACA
1901 CCATCTTCCG TCCACGCTGT GCCCAGGACA GCTGTCCCCA TCCATGAACA
1951 CAGGGTAAAC ATCTGCCGGG CTCCGCACCA GTGGCTCCCT GGGCCATGGG
2001 ACAGCGGCAG GGCTCACCAC GGACAGCACG TGGCCCAGCA GCCGGCCACC
2051 CTGGCGTCCT GGGGCCTCCT CCCCTCCTCT CCCTCTCACC TTGTCACCTC
2101 CACGGAGCTG CCTGTCTGGG ATAATTTGGG GATTTTTTTT TCTGGGGGAT
2151 AATTCTTTTG CATGACCCCT AAAGAGCAAG CCACACCGGT CTGCTAGCTA
2201 GGTGTCCGCG GTGTGGTG   (SEQ ID NO:1)
```

FEATURES:
5'UTR: 1-261
Start Codon: 262
Stop Codon: 1810
3'UTR: 1813

FIGURE 1A

Homologous proteins:
Top 10 BLAST Hits

| | Score | E |
|---|---|---|
| CRA\|18000005245285 /altid=gi\|5326757 /def=gb\|AAD42035.1\|AF07880... | 1047 | 0.0 |
| CRA\|18000005199792 /altid=gi\|10835006 /def=ref\|NP_001211.1\| cal... | 1044 | 0.0 |
| CRA\|18000004938668 /altid=gi\|6671660 /def=ref\|NP_031621.1\| calc... | 1039 | 0.0 |
| CRA\|18000004937301 /altid=gi\|11120682 /def=ref\|NP_068507.1\| Ca+... | 1038 | 0.0 |
| CRA\|18000005245287 /altid=gi\|5326762 /def=gb\|AAD42037.1\|AF08192... | 1001 | 0.0 |
| CRA\|18000005171302 /altid=gi\|3668373 /def=gb\|AAC79460.1\| (AF085... | 999 | 0.0 |
| CRA\|1000737074531 /altid=gi\|6688228 /def=emb\|CAB65122.1\| (AJ252... | 986 | 0.0 |
| CRA\|18000005245288 /altid=gi\|5326764 /def=gb\|AAD42038.1\|AF08341... | 986 | 0.0 |
| CRA\|18000004964693 /altid=gi\|466360 /def=gb\|AAA81938.1\| (U06636... | 982 | 0.0 |
| CRA\|18000005199791 /altid=gi\|4139268 /def=gb\|AAD03743.1\| (AF112... | 982 | 0.0 |

BLAST dbEST hits:

| | Score | E |
|---|---|---|
| gi\|12801212 /dataset=dbest /taxon=960... | 1675 | 0.0 |
| gi\|12868201 /dataset=dbest /taxon=960... | 1453 | 0.0 |
| gi\|2053138 /dataset=dbest /taxon=9606 ... | 1247 | 0.0 |
| gi\|10213950 /dataset=dbest /taxon=96... | 1243 | 0.0 |
| gi\|9324431 /dataset=dbest /taxon=960... | 1233 | 0.0 |
| gi\|12921378 /dataset=dbest /taxon=960... | 910 | 0.0 |

EXPRESSION INFORMATION FOR MODULATORY USE:
library source:
From BLAST dbEST hits:
gi\|12801212 Fetal brain
gi\|12868201 Fetal brain
gi\|2053138 Testis
gi\|10213950 Lung small cell carcinoma
gi\|9324431 uterus endometrium adenocarcinoma cell libe
gi\|12921378 Fetal brain Tissue expression from PCR-based tissue screening panels:
hippocampus

FIGURE 1B

```
  1 MATTVTCTRF TDEYQLYEDI GKGAFSVVRR CVKLCTGHEY AAKIINTKKL
 51 SARDHQKLER EARICRLLKH SNIVRLHDSI SEEGFHYLVF DLVTGGELFE
101 DIVAREYYSE ADASHCIQQI LEAVLHCHQM GVVHRDLKPE NLLLASKCKG
151 AAVKLADFGL AIEVQGDQQA WFGFAGTPGY LSPEVLRKEA YGKPVDIWAC
201 GVILYILLVG YPPFWDEDQH KLYQQIKAGA YDFPSPEWDT VTPEAKNLIN
251 QMLTINPAKR ITAHEALKHP WVCQRSTVAS MMHRQETVEC LKKFNARRKL
301 KGAILTTMLA TRNFSVGRQT TAPATMSTAA SGTTMGLVEQ AKSLLNKKAD
351 GVKPQTNSTK NSAAATSPKG TLPPAALEPQ TTVIHNPVDG IKESSDSANT
401 TIEDEDAKAR KQEIIKTTEQ LIEAVNNGDF EAYAFYFENL LAKNSKPIHT
451 TILNPHVHVI GEDAACIAYI RLTQYIDGQG RPRTSQSEET RVWHRRDGKW
501 QNVHFHCSGA PVAPLQ  (SEQ ID NO:2)
```

FEATURES:
Functional domains and key regions:
[1] PDOC00001 PS00001 ASN_GLYCOSYLATION
N-glycosylation site Number of matches: 3
    1    313-316  NFSV  (residues 313-316 of SEQ ID NO:2)
    2    357-360  NSTK  (residues 357-360 of SEQ ID NO:2)
    3    399-402  NTTI  (residues 399-402 of SEQ ID NO:2)

[2] PDOC00004 PS00004 CAMP_PHOSPHO_SITE
cAMP- and cGMP-dependent protein kinase phosphorylation site Number of matches: 2
    1    48-51  KKLS  (residues 48-51 of SEQ ID NO:2)
    2    259-262  KRIT  (residues 259-262 of SEQ ID NO:2)

[3] PDOC00005 PS00005 PKC_PHOSPHO_SITE
Protein kinase C phosphorylation site

Number of matches: 4
    1    47-49  TKK
    2    51-53  SAR
    3    358-360  STK
    4    367-369  SPK

[4] PDOC00006 PS00006 CK2_PHOSPHO_SITE
Casein kinase II phosphorylation site

Number of matches: 9
    1    36-39  TGHE  (residues 36-39 of SEQ ID NO:2)
    2    51-54  SARD  (residues 51-54 of SEQ ID NO:2)
    3    79-82  SISE  (residues 79-82 of SEQ ID NO:2)
    4    94-97  TGGE  (residues 94-97 of SEQ ID NO:2)
    5    109-112  SEAD  (residues 109-112 of SEQ ID NO:2)
    6    262-265  TAHE  (residues 262-265 of SEQ ID NO:2)
    7    400-403  TTIE  (residues 400-403 of SEQ ID NO:2)
    8    401-404  TIED  (residues 401-404 of SEQ ID NO:2)
    9    485-488  SQSE  (residues 485-488 of SEQ ID NO:2)

[5] PDOC00007 PS00007 TYR_PHOSPHO_SITE
Tyrosine kinase phosphorylation site 9-17 RFTDEYQLY (residues 9-17 of SEQ ID NO:2)

FIGURE 2A

[6] PDOC00008 PS00008 MYRISTYL
   myristoylation site

Number of matches: 3
      1    302-307  GAILTT  (residues 302-307 of SEQ ID NO:2)
      2    332-337  GTTMGL  (residues 332-337 of SEQ ID NO:2)
      3    390-395  GIKESS  (residues 390-395 of SEQ ID NO:2)

[7] PDOC00100 PS00107 PROTEIN_KINASE_ATP
Protein kinases ATP-binding region signature 20-43  IGKGAFSVVRRCVKLCTGHEYAAK  (residues 20-43 of SEQ ID NO:2)

[8] PDOC00100 PS00108 PROTEIN_KINASE_ST
Serine/Threonine protein kinases active-site signature 132-144  VVHRDLKPENLLL  (residues 132-144 of SEQ ID NO:2)

Membrane spanning structure and domains:

| Helix | Begin | End | Score | Certainty |
|---|---|---|---|---|
| 1 | 195 | 215 | 1.665 | Certain |
| 2 | 319 | 339 | 1.301 | Certain |

FIGURE 2B

```
BLAST Alignment to Top Hit:
>CRA|18000005245285 /altid=gi|5326757 /def=gb|AAD42035.1|AF078803_1
        (AF078803) calcium/calmodulin-dependent protein kinase II
        beta subunit; CAM2 [Homo sapiens] /org=Homo sapiens
        /taxon=9606 /dataset=nraa /length=542
      Length = 542

Score = 1047 bits (2678), Expect = 0.0
Identities = 516/542 (95%), Positives = 516/542 (95%), Gaps = 26/542 (4%)
Frame = +1

Query:   1    MATTVTCTRFTDEYQLYEDIGKGAFSVVRRCVKLCTGHEYAAKIINTKKLSARDHQKLER    180
              MATTVTCTRFTDEYQLYEDIGKGAFSVVRRCVKLCTGHEYAAKIINTKKLSARDHQKLER
Sbjct:   1    MATTVTCTRFTDEYQLYEDIGKGAFSVVRRCVKLCTGHEYAAKIINTKKLSARDHQKLER     60

Query:  181   EARICRLLKHSNIVRLHDSISEEGFHYLVFDLVTGGELFEDIVAREYYSEADASHCIQQI    360
              EARICRLLKHSNIVRLHDSISEEGFHYLVFDLVTGGELFEDIVAREYYSEADASHCIQQI
Sbjct:  61    EARICRLLKHSNIVRLHDSISEEGFHYLVFDLVTGGELFEDIVAREYYSEADASHCIQQI    120

Query:  361   LEAVLHCHQMGVVHRDLKPENLLLASKCKGAAVKLADFGLAIEVQGDQQAWFGFAGTPGY    540
              LEAVLHCHQMGVVHRDLKPENLLLASKCKGAAVKLADFGLAIEVQGDQQAWFGFAGTPGY
Sbjct:  121   LEAVLHCHQMGVVHRDLKPENLLLASKCKGAAVKLADFGLAIEVQGDQQAWFGFAGTPGY    180

Query:  541   LSPEVLRKEAYGKPVDIWACGVILYILLVGYPPFWDEDQHKLYQQIKAGAYDFPSPEWDT    720
              LSPEVLRKEAYGKPVDIWACGVILYILLVGYPPFWDEDQHKLYQQIKAGAYDFPSPEWDT
Sbjct:  181   LSPEVLRKEAYGKPVDIWACGVILYILLVGYPPFWDEDQHKLYQQIKAGAYDFPSPEWDT    240

Query:  721   VTPEAKNLINQMLTINPAKRITAHEALKHPWVCQRSTVASMMHRQETVECLKKFNARRKL    900
              VTPEAKNLINQMLTINPAKRITAHEALKHPWVCQRSTVASMMHRQETVECLKKFNARRKL
Sbjct:  241   VTPEAKNLINQMLTINPAKRITAHEALKHPWVCQRSTVASMMHRQETVECLKKFNARRKL    300

Query:  901   KGAILTTMLATRNFSVGRQTTAPATMSTAASGTTMGLVEQAKSLLNKKADGVKPQTNSTK   1080
              KGAILTTMLATRNFSVGRQTTAPATMSTAASGTTMGLVEQAKSLLNKKADGVKPQTNSTK
Sbjct:  301   KGAILTTMLATRNFSVGRQTTAPATMSTAASGTTMGLVEQAKSLLNKKADGVKPQTNSTK    360

Query: 1081   NSAAATSPKGTLPPAALEPQTTVIHNPVDGIKESSDSANTTIEDEDAKARKQEIIKTTEQ   1260
              NSAAATSPKGTLPPAALEPQTTVIHNPVDGIKESSDSANTTIEDEDAKARKQEIIKTTEQ
Sbjct:  361   NSAAATSPKGTLPPAALEPQTTVIHNPVDGIKESSDSANTTIEDEDAKARKQEIIKTTEQ    420

Query: 1261   LIEAVNNGDPEAYA------------------------FYFENLLAKNSKPIHTTILN   1362
              LIEAVNNGDPEAYA                        FYFENLLAKNSKPIHTTILN
Sbjct:  421   LIEAVNNGDPEAYAKICDPGLTSFEPEALGNLVEGMDFHRFYFENLLAKNSKPIHTTILN    480

Query: 1363   PHVHVIGEDAACIAYIRLTQYIDGQGRPRTSQSEETRVWHRRDGKWQNVHFHCSGAPVAP   1542
              PHVHVIGEDAACIAYIRLTQYIDGQGRPRTSQSEETRVWHRRDGKWQNVHFHCSGAPVAP
Sbjct:  481   PHVHVIGEDAACIAYIRLTQYIDGQGRPRTSQSEETRVWHRRDGKWQNVHFHCSGAPVAP    540

Query: 1543   LQ  1548    (SEQ ID NO:2)
              LQ
Sbjct:  541   LQ  542     (SEQ ID NO:4)
```

FIGURE 2C

Hmmer search results (Pfam):

| Model | Description | Score | E-value | N |
|---|---|---|---|---|
| PF00069 | Eukaryotic protein kinase domain | 306.2 | 3.9e-88 | 1 |
| CE00022 | CE00022 MAGUK_subfamily_d | 293.8 | 1.3e-86 | 1 |
| CE00359 | E00359 bone_morphogenetic_protein_receptor | 15.0 | 0.0015 | 1 |
| CE00031 | CE00031 VEGFR | 0.9 | 2.1 | 1 |
| CE00287 | CE00287 PTK_Eph_orphan_receptor | -65.4 | 0.00046 | 1 |
| CE00292 | CE00292 PTK_membrane_span | -77.0 | 0.00018 | 1 |
| CE00291 | CE00291 PTK_fgf_receptor | -93.1 | 0.0021 | 1 |
| CE00286 | E00286 PTK_EGF_receptor | -132.2 | 0.0059 | 1 |
| CE00290 | CE00290 PTK_Trk_family | -161.3 | 0.00033 | 1 |
| CE00016 | CE00016 GSK_glycogen_synthase_kinase | -196.7 | 9.2e-06 | 1 |

Parsed for domains:

| Model | Domain | seq-f | seq-t | hmm-f | hmm-t | score | E-value |
|---|---|---|---|---|---|---|---|
| CE00359 | 1/1 | 132 | 186 .. | 272 | 327 .. | 15.0 | 0.0015 |
| CE00031 | 1/1 | 133 | 205 .. | 1068 | 1139 .. | 0.9 | 2.1 |
| CE00286 | 1/1 | 14 | 252 .. | 1 | 263 [] | -132.2 | 0.0059 |
| CE00290 | 1/1 | 15 | 253 .. | 1 | 282 [] | -161.3 | 0.00033 |
| CE00291 | 1/1 | 14 | 267 .. | 1 | 285 [] | -93.1 | 0.0021 |
| CE00292 | 1/1 | 14 | 267 .. | 1 | 288 [] | -77.0 | 0.00018 |
| CE00287 | 1/1 | 14 | 270 .. | 1 | 260 [] | -65.4 | 0.00046 |
| PF00069 | 1/1 | 14 | 272 .. | 1 | 278 [] | 306.2 | 3.9e-88 |
| CE00022 | 1/1 | 10 | 305 .. | 13 | 316 .. | 293.8 | 1.3e-86 |
| CE00016 | 1/1 | 1 | 343 [. | 1 | 433 [] | -196.7 | 9.2e-06 |

FIGURE 2D

```
   1 GAGCTGCTGT GTCTCTGTCC CCAGGGGCAG AGGGGCTGTG GGGTTGCAGG
  51 CTCAGCGTCT GGGACTCTGG GGTGAAGGCT CAGCCATGCC CTGCAGACAC
 101 CATGGGGCAG GGCTCAGACC TGTGCACCTG TCTCTTGCAA ACCACTGTTT
 151 TCTCTGTTTT GTAACCCCCC ACCCAACCCC ACATAACACC TCTGGGTTTA
 201 AACAACATGC ACCCTTGTGC CGGTCACCTC CCTGCAGCCG GAGAACCTGC
 251 TTCTGGCCAG CAAGTGCAAA GGGGCTGCAG TGAAGCTGGC AGACTTCGGC
 301 CTAGCTATCG AGGTGCAGGG GGACCAGCAG GCATGGTTTG GTGAGTGCCA
 351 GGGGCAGGGT GTGTTGGCTG GCAGTTGGCA GGGCAGGAGG TGATGCTGAC
 401 AGCCCCTTGT GGCCTCTTCC CCTCTCTCTA GGTTTCGCTG GCACACCAGG
 451 CTACCTGTCC CCTGAGGTCC TTCGCAAAGA GGCGTATGGC AAGCCTGTGG
 501 ACATCTGGGC ATGTGGTGAG GCCTGGCCTG AGTTGGTGCG GGGCAGGGCC
 551 TCGGGTGTTT CAGGACTTCC CACCTACATC CTGGAGTGTG CAGTGGCCAG
 601 CACGTCTTGC TCTCATCTGG GTTTATCTGT GTCAGACCTG CCCTTGAGCT
 651 GCCCTGGCAG GGGTCTGCCC ACACAGCCAA GAGCCCCTT TCCACCCAGA
 701 TTAGAATTGC TCACATGAAC CTGGCGCACC CCAGTGCTCG CCTGCGCTCA
 751 GCAGAGGTCT GGTCCAGAAG TGTGGTGGGT GGATGGGAGT GGAGAAGAGA
 801 GGTCAGGGGC TGTTGGGCCA TGGGCAGGGC CACCTCCTTG GGTAGGGGTC
 851 TCCTCCCACA GAGGTGGGGA GCAGCAGAGG GGCTTGACAT CACCCTCATC
 901 CCTGTGATAG TGTGGGTGTG GGGCAGAGGT CAGGGGGCCG GCTGTGCCCT
 951 TCTACCCCAG TGTCTGCTGC ACAGGTGGGG GCAAAGGAAT GCTGAGGACC
1001 CCAATGCCCT CCCAGGGCCA CAGGAGCTAG GCAGTGAGGG TGCAGGGCAT
1051 GGGCTTCATG GACGGTGGCA CCCTGCAAGT GGCTGCGGTG CTCACAGGCC
1101 CCATCCGCAG GGGTGATCCT GTACATCCTG CTCGTGGGCT ACCCACCCTT
1151 CTGGGACGAG GACCAGCACA AGCTGTACCA GCAGATCAAG GCTGGTGCCT
1201 ATGACGTGAG TGCACCAGCC CCTCTCTGAT GAGCTCCCTT CCTCCAGGTG
1251 TGGCCGGGTG AGGGCAGCGT GGGAAGAGGC TAGGAGTGGG GTGAAGCCAC
1301 CTGTGGCCAG GTCCTGGGTC CTGCTCTCCC AGATTCGTGG CTGGAGATGA
1351 AGCCCCTTGG AGAATTCTTG CCCCTGCCTG AGAGGGAGCT TCAGGCCCGG
1401 CCGGGGCGCT GTTTCCTTCT GCAGTTCCCG TCCCTGAGT GGGACACCGT
1451 CACTCCTGAA GCCAAAAACC TCATCAACCA GATGCTGACC ATCAACCCTG
1501 CCAAGCGCAT CACAGCCCAT GAGGCCCTGA AGCACCCGTG GGTCTGCGTG
1551 AGTCGCCCTT GGTGCCCATG GTGGGAGGG GGCTCCTGGT GGAGATGGCC
1601 TCAGACCACT CCCCTGGCAA GGACCCCAAG AGGGTCCTGT TCCTGACATC
1651 CAAGAGCTCC CTTGGGTCCC CTGGGTGCTC CTTGTGGCCT CTGGCTTGGG
1701 ACATACCAGC ACGTTTGTGA GGCCTGGGGC TTGGAAGGCA TTAGAGGGTA
1751 GAGGTGATCC CTTCCTCCCA ACTGCAGTCC TGTCTGTGAG GGGCAGAGTG
1801 GACGAGGCAA GGGAGAGACG AGTCTTGAAG TCCCAGGCGG GTGGGACAG
1851 ACAACCCTTG CCGCAATGGT GGCCGGTGGC TCTTGGCAAG TGGGGACCCC
1901 AGGGTGCCAC AAGCCTTGCC ACCCTGGCCT CTCCCCTGTG CCTCGGGCTC
1951 GGCTGCCATA TGACCACCCA TTTCCCCACA GCAACGCTCC ACGGTAGCAT
2001 CCATGATGCA CAGACAGGAG ACTGTGGAGT GTCTGAAAAA GTTCAATGCC
2051 AGGAGAAAGC TCAAGGTGAG GCCCTGGCCC CTAGTCCCAG GCACGGCCAT
2101 GCTTCTCTGT GTCCCTCTGG GCTGGAGCAG GGGGCCTTG GGGGTCTGG
2151 GCAGACCTAG GGGTTACTGC TGCCCCCAAG ACTGACTGTT AGCAAGTCCC
2201 AGACTGGATG CATCAGGTGA ACTCAGGCCA GCTTGGGAAT GAGTCCAGAG
2251 GGGCCCTGGG CCAGGTGTGG CTCCTCCTAG TTGTCTGTGC CACCTCCTAG
2301 CAGCCCTTGG AGGAGCTGTC CTGAAGCGCT CGCTGTGGGC TCCTCACCCG
2351 GGCTCTGCAG GCAGCACTCA CCCTCTGGCA GTCACACTGT TTAGTACAAG
2401 CAAGTCCGAA GCTTCCGGCT CAGACAGGTT TGGTAAGGAG AGCAGAGCCA
2451 CACACACTGG TCTTGGGTGG GCTGGGGGAG TTCTGGGAGG GAGGTGGGTC
2501 CCAGTAGGGT ATCCAACCTG CCTGCTTTGG TCAGGGCTGG CTCCGGTGAC
2551 CGCACACTGG CAGTCCCTCT ACTTGTGGGT TCCGGATGG GGACTTGTTG
2601 CCTGACTGCC CTCTGCTGGT CTCTGAGCAG TTCTCCCCGG AAGCCCCAGG
2651 ACTGTTGCCC TGTCTGAGCC TGTCAGGAAA AGAAGGGGCT GTCAGGGAGC
2701 TGGACCCCAG AGGAGCTGCC GTGGTGACCA GCTGTTCTGG TGACCCCTGA
2751 GGCTTGAGGG GTCTTGAAGC AGCTAGAAGC TGTAGTTGGT CAACAGGTTT
2801 AGGCCCAGGG TGTGTGTAGT TCTGGAAATA GGTGATCTGT CTCAGTGCGG
2851 CTGCTGGCTT CCTGGAGCTC TTGCCTCTCT GGAAGGCTGA GGTCATGTCA
2901 GCCTCATGAC AATGAGGCTG AGCATCTGGG CAGGAGGACA GGGGTCTTAT
2951 CCTGGCCAGA AGCCAGCAGG GAACACTGAT GGGATAGCCC CGGTTTTATC
3001 TGTGTCTCTC CCCAGGGAGC CATCCTCACC ACCATGCTGG CCACACGGAA
3051 TTTCTCAGGT GAGCCTTTCT TCTCCAGGGA GACAGGCGCT GCCCCCTCCC
```

FIGURE 3A

```
3101 TGCTGGCCCA CGCAGGAGAG CGCCTCCTTC CTCACCAGCC TCTCCACTCC
3151 TCCTCTGCGG CAGGCCTGCC CTCGGCGTCT GCCCTCAGCT CTGAGACCCA
3201 CTGCCCACCT GGCCCGCTG GGCTCCCACC TTGGGTGATA CCACAGGGTC
3251 CAGCCCCCCG AGGCCATCAC CTTCGTGCTG GGTCTGTGTC CCTCCACCCC
3301 CTGAACACGA GCGTCTGTGC TGCCCACTG GGGCTCACAG CATCGTGTGT
3351 GTCTGTCCAG GCGTTTGTCG GGCATCTATG TGGCCTCCTT GTCATTTTGA
3401 GTGCTCTGAA CATTGTGTTT TGTGCGGAG GTGGGCAGAA GGGATGCGGG
3451 GTGATGCGGG AGGCTCGGGG GCCTCCTTCC AAGTTCTGGA TGAGCTGCAG
3501 CCTCCTGTCC CGGCTGCTCA GGGTGGGTGG TTGGGAAGCA AGTTCTCTTG
3551 GCAGGGGGGT GGGGTCTGTT ATAGACCCCT GAGGCCCAGG GCGCTGGCAG
3601 ACCCATCGGG GCATGATGTT AGCCCCGGAG TGGAGCCGGC AGCCCAGGTC
3651 TGGACAAGCT GTACCTGTGG CTTCTCCGTC GTCCGACACT CCGTGTGCGA
3701 GCGTCTGTGA TCCGTCTCTC TCGTTGTCCG TTTGCATCTG GTGCCCCCCA
3751 CCCGCCATCC TGTTACTTTT GCTGTGATGC TGTAATGCCG GGAACGCGTG
3801 CACACGGTCA CACCAACACT AATAGGACTG TCCTGTCTGC TGTGTGCTCA
3851 CCACACCCTT TGGGCATGAG AAGCCCCAC TGGGGTTTTC TAAGGAGAAA
3901 GGAGGCAAAT GCTTTTCCGT GTCAATCAGT CCAATCTTGT TTTCACTCTC
3951 TTGAGCAAAG GATTCTGGAA CCATCTGTCA CCTAAACTTT AACTCTAATC
4001 TTCTTCTGCT TCCTTTGTCT CTTTTCTTCC CTTACCTCGC CCACCCCTCG
4051 TCTGTGTCCG CCCACCCCTC CCTTCCCCTC GTCTCTAACC CGGTGCTAAC
4101 AGTGGGCAGA CAGACCACCG CTCCGGCCAC AATGTCCACC GCGGCCTCCG
4151 GCACCACCAT GGGGCTGGTG GAACAAGGTA GATGTGTCTC GACCAGCGTC
4201 CCGCCCGCTC CCGCCCGTCC CTCCTGCCAG CATGCAGCCC CCTGCTGCAC
4251 GCAGCCGCTG GCCGGGCTCC AGAGCCGCCC CAGAGGCCGC CAGGCCCCCG
4301 GGAGCCCCTG CTCCCGTGTG GTCACATCCC AGCAGAGCCC ACCACAAGGG
4351 CAGGGAGGCA GCCCCCAAGG CTCCTCGCCT GTAAGAGGAG GGGCTGGGCT
4401 AGGTGGCCCC TGGGCTACAC CAAGCCCTTC TGGTCCTGGC CCCCGAGGTC
4451 TGGGGGTCCG GAGACCCCCA TTAAGAATGG CCTGGGCCCC ACAGGGAGCC
4501 ACTGGGCCTG CTGCTGGGGG GTCTGAATCC TGAAAGGAGA GCCTTGAGGA
4551 GCAGAGCCAG AGAGGCAGAG GCCCTTGGGG CAGACACACA CCCTGCCCCT
4601 CTGGGGCCGC ATGGAGACGG TGGTCTGTGC TGCTGAGTCC TACACATGCA
4651 TGTCTGCCCT GAGCATCCCC CCAGGACAAG CCGCTCTGGA GTGGGTGAGG
4701 GTTTTATGCA CCCTGAGGAG ACTTTCAAGG CTTCCTCTTG GGTTGTTTCT
4751 GCAAAGTCCT CCTCCCCTGG CCTCAAACCC TGTGAGGGAA AAGGCCGGCA
4801 CTGGCCACCT GCTCCTCTGG GCTGTGCGGG GCCAGAGCCC AGAGGCCCAA
4851 GTTGGCTTCT GCCCACCTGC TGGCTTGTGA CCATGGGCAG ACCCCATGAG
4901 GGCTAGGCGA CCCCAAGACC TCCTTGCAGC TCCAGCCTGA GCTGAAGGCT
4951 GGTGAGAGCT TAGGGCAGGC CAAGCTGACA ACGCCTGGCC ACAGAACACA
5001 GAGGGCTACA GGGGTGACCC CAGATCCTCC CTGGGCTGAG CTGCTGAGTT
5051 CCCTGTCGGT GCCTCCAACG TGGGCTGGGG ACCCGGCAGA GGTTCCAGGG
5101 TGCTGGAGAC TGCCTTCCCC AGGCCTCCTC ATGACCCACA GGGTGAGCAG
5151 CCTGGCCTTC CCAGCCAGAG AACCCTCCTT CTGGGGAGGC CCAGGGCGTC
5201 CTCGGGGAGG GCAGTCTATT CTCCTCCCAT GAGCCCAGTG GACGTGTCTA
5251 GCAGGCAGCA CCCCGGGAGA GCCCTCCCAC GTCTTCTCCA TTTGACAGGC
5301 CTTTCCAGAG CGCAGGCGGG AGGGGGCTGT GATTAGAAAA GAGTGAGGCT
5351 AGTGGCTTCT GGGGAGGCAC TGCTGCCCAG GGGACAGTGC TGAGAGACAG
5401 CTGCCTCTAC GCTGCCCTGT GCCCGGGGCT CCCGCTGCAA TGCCCGCCTG
5451 TCTGCAAGTG AACGTGGGGC GACGGTGCAT GAGGCCCTGC ATGTGTGGCT
5501 CCACCCTGGG CGCCGAGAGC AGCTCTGTCC TGGAGGGTGG TCAGTGCATG
5551 TGGACAGAGC CCAGCATGGC TGTCCTGGGT GACCAGCTAA GGGGACAAGG
5601 CAGAGGCAGG GCTGAGAGGA CCACCCATCC TGCTAGGTCA GCCCAGCTCA
5651 GCCATATCAC ACGGCAGTGA GCATGAGCT CAGTTCTCTG CCAATGGCAG
5701 CTGAGTCTAG TACCATCCAG TCAGAGTCTG GTACCAGCCC ATGTGGCATA
5751 GCCCCCTCGG CCCGCAGAGA GACCCCGTCT GTCGAGTGTG CTTCAGTTTG
5801 GCCTCTGTGG TCTCTCCTGC ATTGATCAGG TGTAAGGGCA TAGGAGACCC
5851 AGTGTCCGC CAGCTGCAGG GTGGCAGCAG TTGCCCCGGC CTGGAGACCC
5901 GGGAATGGGC AGTGCCTTCC CAGGATGGAG GGCAGAGGGT CTCTCCTTGT
5951 CCCACAGAGG CCTGCAGAAC CCCCAACCCA GGTGTCTGAG ATGCCTGTGA
6001 CTGCTCCGCC TACCCTGGGC TCCTGCGGCA CCTAACGCAT GCTTTGAACT
6051 TGAGACACAG AAAGGAAGTT CCCGTGCCCT TGAATGCTAG TGTAGATGGG
6101 CATCGACAGG ACTCTGGCCA CGGTGAATCT GGAGTTAGTC CCAGGCAGAG
6151 ATGTGAAATG AGCAGCCCCC CAAAAAATGG TTGGCCGGGA GCCATGCACT
```

FIGURE 3B

```
6201 CAGGAGGGCC GGGCCCATGC ACCCCACACT GCGCCCAAGG CGTGCACAAG
6251 CGATTGTTTT AAAAGCGGGT TCACAAGGAA GGATGTTTGG GAACTGACTG
6301 AGACAACAGG GACGTCTGCT GCAGGGCTTC CCAGAGCTCT GATGGCAGCG
6351 TCGGCCTGAG TCCTTCGAGG AGGGCTGGTT TGTACGTGGC ATTTGCTGCC
6401 CACTGGACTG TGAACTTCTG TCTTTTTATT TCCCACTGCT GCTGTGGTAC
6451 ATCTCCAGTA GCATAGTTTG GAAATGCAGG TTTTGATAGA CTCAAGGATC
6501 TAAATAGAAC CCTCTTAGTA CCAAGGACTG TCCGGGGTCT CTGCCAGCCC
6551 CGCCGATGGG CCTAACTGTG GTGCCTCCTT TCCTGTGAGA ATCTTCTGAG
6601 GACATGCCCG GGGAAAGAGC TCAGTTCTGC TGCTGCCTAG GGTGCCATGC
6651 TGGCCCCGGT TCCAATGCAG AGCCTAGCTG GAAGTACCGC TGGGTTGGCG
6701 GAGGCTACGT GCCTGACTGT CCCCTCGGGG GTGGGGTGGA ACTAGCCTTC
6751 TGAAACCGCC TGCTTCAGTT GGCCACAGCT TTTTGAAATG TGTGTTTCTG
6801 GAAGGGACTG GGTCCCTTCC TTGCCTGTTC AGCTCCCCAC GACAAATGTC
6851 CTCAAGGCGA GGCTGGATGC TTCCTTCCTC AGGCTCCTAG GAGGAGCCCG
6901 TCCCCAGCT GTGTCGGCA GCTGGTCACC AGCAAGGACA GGATCCCTCA
6951 GCTGCAGCCT CAGGCTGGCT GGCACTGGGC GGGTGTTTCT GGGATGAGTT
7001 GTGTGTACTG GAGATGGAG GGGAGCTGAG AGGGTGGGAT GCACAGACAG
7051 GAGAGGGGAC TGTGGGGGTC CTGGAACCCT GAGTTCCAAG TCTTCAGGAC
7101 TCTCCCTCCA TAGCAAGTTA CAGGGAAGCA GATTTGAGCC ACAGGGAAGC
7151 AGATTTGAGC TGCAGCGAGG GGGAGGGTTT TCAGTCTGTG CTATAGGGAA
7201 GTGGGCAGTC GGCATTTCTG GTCCTGGGAA CTCACTGGGC AGGGCTGCCT
7251 TGGGACATCA GGGAGGTGGC GCTGTGCTCA GCTTCACCAG GAGGGGCCTT
7301 AGGCCTGGGG ACGGAGAGTG ATGCCTGAGG CCCCTCTACT TCTCCATGGA
7351 TCCTGGGAGG GACTCCTGGG CTGGATACAA AATTGTTGAG AGTTAAGAGA
7401 TCTGTGAGGA AGGGGAGGCT GGGAATAGAA AGTGTGTGCC CACTGCACAT
7451 GGGGTCCGCA GGGCCACGTG CAGCCACTGC GCAGGCACAA CCCCAGTCCC
7501 CACAGAGCCC AGGAGGGGCC AGAGCCATGG AGGAGGCAGC ACTGGGCATT
7551 TGGACAGGGA GGGGGTGGTC AGCAGGCAGC AGGCCCAGGC CTGTCTATGC
7601 CCTGCGGGGT GCAGCCTCCT GATCTCCACG GCAACCTGGA GCACCCAGCG
7651 TCAGAACCAC CGGGAGGGCT TATGGAACAG ATGTCCAGCC CTGCAGAAGT
7701 TCTGGCTCAG GAGGGCGGGG TGGGCCTGGG AATTTGCATT TCTGACTGTA
7751 CAGGGCGATT CTGCTGCTGC TGCTGCTGCT GGGGTTGGGG GAGGATCCCA
7801 TTTGAGAAGC GCTGCAGTCC TAGGTTGAAA CGTGCCTGTC TGTCCCCACC
7851 CAGGCCTGCA TGGGCAGCAC GGGATCCCCA GGCAGGAGGA CCCAATTTCA
7901 TGGCCTGGCC AGCCAGGGTC CTGGAGCCAG GCGGTGGGGG AGGGATGGGG
7951 GATTGCTGTG CCACCTTCCT TCCCGGCTTG GCCCGGGGGC AAGCATCCTC
8001 ACACTTCCCA TGTCGTCATC CCCTTGGCTC CAGCCTGGCT GCCTCTCTAA
8051 CCCTGCTGTA CCGGCTGGCC GCATGGCCCT GGCTCTTTTT GGTGAGCGTG
8101 GTCCAGGACT GGTGACCTGT GAGTCCTGGG CCCGCAGTCT TGCGCCCCTG
8151 CCCGAACCAA CACAAATCTT GTTTTCTCTC TCTCTCTTCC TTCCTCACTC
8201 CCTCCCCTTC TCACCTTTCC TTTTCTGTAA GGTAAGCTGA CTTCCTCTTT
8251 TGGTTTTTTA TTTATTTTTA TTTTTTAGTT CTGTAATTAA AATCCTAACA
8301 GCCATGGAGG GTGTGGGCAC CGGGGCTGG GGCCAGGCCC CTCTGACCTC
8351 TGAGGGGGAA TGCTGGGTGA GGCAGGGCC CCGCTGCTGG GACCAAGTAT
8401 CCTCAGGGGC TTGTGGGCAG AAAGGCCTGT GCTGGCCCCA GTCAGTGCAC
8451 AGAAGCGGCC CCAAGGCCAG GGCTGCTGGG CAGCTCGGAA TGAGGGCGAG
8501 CAGGGCTGCC CTTGGTGCCT GAGCCAAGGA GCCAATGGGA CAGACCTCTG
8551 AGCCTGGGTG CCAAGTATGA GGTCTGAGAC AGGGTGAGCC CCTGGGCTGG
8601 GACAAGGCCC TCTGAGTGGG CGGCCAGCTG CAGCCCACCC ACCCCTACCC
8651 CAGGAAGGCA GGGCCCGGGA GGGCATGACC TCTGGGGTGC TGGCTCAGCT
8701 GCCCCACCC CAACCTGACA CCGCTAGTCC TGAGTTCCCA TCAGGGAGGA
8751 AGCAGCATCC TGCCTTCCTC TAGGAAGAGC TTGCATGTGG CCCAGAAGCC
8801 AAGGGGGCTC CCCAGCACCC ACGGGCATCT CTGGGTCTGG TCAGAGGAGA
8851 AATCTGGATG CTTGCAGGAG CCCCAGGGTC ATGGAGGAGG CTGGAGACAG
8901 GGCTGTCCTG GGGTGATGGG ATGGCCCCC CACCTGCTCA GAGCCAGCCT
8951 GGGTGCTGGA ACCACACTTG CCTCAGGACC CTGGGCTTGC TCCTGGGGAA
9001 AGAGTGGGGT CAGGCAAAGG GGTGGGGTTG CGCTGCAGCG AGACCCAGGC
9051 CCATCACTCA CCATACCTTC TTCCTCCCCA TGCAGCAGCC AAGAGTTTAC
9101 TCAACAAGAA AGCAGATGGA GTCAAGGTGA GGCTCCAGCC GGGCCCTGTG
9151 GTGCCGGGGA GCCCAGAGCC TGCAGCTTCA CCCCCACGCC CTGGGGCTCC
9201 TGCTCTGGAG TCCCCCTCCC CCCATGCCCT GAGAGACACG GGACAGGGAA
9251 TGGCGAGTGA GGGGCTTCTC CCACCTAAGA GTTCCTCTTC CCTCTCTCCA
```

FIGURE 3C

```
 9301 CAGCCCCAGA CGAATAGCAC CAAAAACAGT GCAGCCGCCA CCAGCCCCAA
 9351 AGGGACGCTT CCTCCTGCCG CCCTGGTACT GAGCTCCTCA AATTCTGCCT
 9401 CTCAGCCCCT CCTACGCCCC TGGCTGTGTG ATTGCCGCTG GTCAGAGGGG
 9451 GCCGGGTGAA GGTGGGGTCT GGCCCCGCCT GGCCTGTCTG ACAGCACTCG
 9501 CATGGCCCCC GCCCCTCATC CCTCACCGGT GGTGAAGTGG AGAGAAGAGG
 9551 CCACTGTTGT GGGGGGCTCC AATTCAGACA GGTTTAGGAC TGCTCTGGGG
 9601 AGCCCCTGGC TGAGACCCAC AGATGTTGGG GTGCAGGGGA GAGGCCCAGC
 9651 CTCCCACCCA TGTTGACTTG TGGATGTCTC TCCAGGAGTG TTCAGGAAGT
 9701 CAGTGAGGCA GAAGATACCC TCTCCCCACC AGGACCCCAC CCTCAGCTCC
 9751 TCCACCATCC TCAACAGGCC GACCCACAGA CCACTCCGAA GGTCTGGCTT
 9801 GGTGGGGCTG GGCCAGGATC TGCAGGGGGA ACAGCCCATA GTGGCACATT
 9851 CCACGGCCCA TGGGGAGACG GGGCCACGGT GGTGCAGTAG AGAGGTGTCT
 9901 AAGCCAGTGG CAGCCAAGGG GAGGGCTTGC CGTCACCTCT GTGTTCCCTC
 9951 AGTGCTGCTC TGTGGCTGCC TGAGAGGCAG GGCTTAGGGG CTCCCTGCCG
10001 GGGAGGGGAG GGGTCCCCAC CATGCTCCGC TCCAACTGCG CCCCTCAGTG
10051 CCCCTTGCCC TGGGGGCTCC TACAGGTGAA CCCTATAGCA GTACTCCCAA
10101 GGATGTAAAG TTGTGGCTGG TGGGTGCCGG CCTTCCTGCT GGGGCGCTGT
10151 GCTGTGTCCC CTCAGCTGTC CTAAGAGCTT TGGGGCTTGC TGGCCCGTAG
10201 GTCCCCATAT TTGCTGGAAG CAGGCTTGGT GTCCCCTGAG AACCCCAGGC
10251 CAGGCTTCGG GAGCCAGCCC CAGACCGCCC ACGGGAATAC TGGGTTTGCC
10301 AAATGGCCAC CTTGAGACCC AGGAGAGGAG AGCGGTCCTG GGAGGGGCGA
10351 GCTGCTCAGA GCAGCCAGGC CGTGGCTGGA GGGTGGCCTG GTGCAGCCTA
10401 CCTAGGGCCT TCCAGTGGCC AGGGCAGCCC ACGTGCCAGC CTCACAGCCA
10451 GCCCCATCTC GGACCCTGTC CATCCCATGT GCCACCGCCA CCCCCATGAC
10501 ATCTTCAAAC CTGTGCCCCC CACCACGCTG GGGCACAGGT TCAGGCAGTA
10551 AAGGGTAGGG AGAACCCCTC AAGACCGAGC CTGGCTTCTC TGGCTCCCAC
10601 ACACATTGTG CAGCTTGTCG GGGCCCCACA CGGTCCATCT CCCACCCTGG
10651 ACAGCAGCAC CTCCGCCAGC CTGGACAGAG CTCCTGTCCA TTCCATCCCT
10701 GCCGGCTGAC CCAGGCTCCT CCCCCAGCTG CTCCACGCCG CCTCCATCCC
10751 TGTCCCCCAC TCTGCTCTGC ACTTCTTTCT CGCAGGCTCT GGCCACCCAC
10801 ACCTCCTCTG TCTCCCTGTT CCCCTCCTGG TGGTCTCCGC TTCCTCCTCT
10851 TCTCACTTTC CCTCTCTTTC CTTCCTCTGT GTCTTCCTTC TTCTGTAGGA
10901 GCCTCAAACC ACCGTCATCC ATAACCCAGT GGACGGGATT AAGGTACTGC
10951 CCCACTTTCC TCCTCCCGCT TTCCCCAGGC AGGAGGCTCC AGGCCAGGAG
11001 AGAGGTCTGG GGCAGCATTT GTGCCAGAGT GGAGGGCAGA TGTCCCATGG
11051 CCCTGGCCGC CCCTCCCCGC AGTACGGTAG GGCCCCAGTC CGTCTTCGTG
11101 GGCAACAACA GGACAGACTG GCTCAGGCCC CAGGCGCGCC CCTGGAGGTG
11151 CTTGGCACAG TTGCGCCCGG TCCCCATGTG GCCGACACTC TCAGACCAGG
11201 GCTCTGCGTG TCCCACCTAC GGCAGGCAGT AGGGCTTCCT GAGGTCTGGA
11251 GCAGGGCCTG CATCTCAGGA GCTGCATCCT TGGCCCTCCT GGCTGTCCTC
11301 CACCCCACCT CCCTCACGTG GCCCCCAGTG CTTCCTGCTG AGCAGACCCT
11351 CCCTCCTCTG CTCCCCTCTC TGCTCTGGCC ATCAGCTCCC ATCACATTGG
11401 CATCATCACT CTGGGGCCAG GGAAGGGGCT GGCTCTCTGG GGTGGTGGGA
11451 GGGATGGGGC CAGCAGCCAA GCCATTTCCA GGACTTCCAA AACAGCGCCA
11501 CTACACCCAA CACGGCCCTC CAGCCCAGCT CCCACCTAGG CCTGGGCTCC
11551 TTACAGAGCC CCCAGAGTGC CTCTGTGGGG ACCCCCCACT TCCTTCTGGC
11601 CAGTGCCACC ACCCAGCCCA TCATCAGAAG ACATCTTTCT CCATGGCAGG
11651 GACCAGGGGG TCCAAGGGGC ACCCATGGTG CTAGGCACCA GGGCCTGGGC
11701 ATTCTTCCCA TCTGGCAGCT GGGGATGGGT GCCCCTGGGA CCCGTGTGTG
11751 TCTGGGGTGG GTCATGCTCT CTGCAGGACT CCTAAACAAC CTTCTGGGCT
11801 GTGGTGAACT CTGAGCCTGC ACCTAAAAGA CCTGTAGTTC TGGTCTAGGG
11851 CCTCCAAGCA GTGTCAGGC AGTGTCCAGA CCAGGGGGCG GTCCCCAGG
11901 GACCTTGTAA GATGTTTCCT CTGAGGAGCA GAGCAGGCCT CCTGGGGACC
11951 TGGGGATGG TCTTTTGAAG GGCAGCAGCC CTGGAGCAGG GTGGGAGAGT
12001 CTGGGGCCAC CTCTGCCCTC TAAGGCCACC TGAGAGGTGA GGCCGGGGCC
12051 TGACTGGACG TCCAGTCCCA GAGGGCAGG TGCCCTGAGG GAATGTGGGC
12101 GACAGGAATG CTCTGCCTGG GGCCAGGCCA AGGTTCCTGG AGCCCTGTGC
12151 GGATCTGCAG AGCTCCTGGG AACGCCTCAC CCTGTATTTT GGATGACACC
12201 GGCTGCTGCT TCATTGGAAC CAGCCAGTCC CATTGTGTTT TACGTCTTGG
12251 AATTTCAAAA AGCCCATTTT CCTCTCTTGT TAAAGAGTCA GCTGAGCATA
12301 CCAGTCTCTC TGCCAGGCTC ATCTTGCTGG GAGAAGTGGA GCCCTCATGT
12351 GTTGGGGATG CAGGGTGGCC ACAGCACTAG GGTGGCAGGG CCGGCCTCGG
```

FIGURE 3D

```
12401 ACTCCGTGCC AGCCTGTGCT GGCTGCCGTG AGAATGCACC CTGGTGAGGG
12451 GCGCCCTCCC AGGGACCAGC ACAGAACTGG GTGTCTTCTC CGGTCACTGC
12501 CGCATGAGGT CCACAGAGCT GGGGCCCTGC AGCCGCCAGA GGGCATGTCC
12551 CCTGAGCCCC TGGCCTTTAA GCCCCGTGGA AGCAGCCGAG GCAGAGATCA
12601 GCTTCAGAGC CTGGGCTGGT CCTGACACAG GCCCAGCCCT GTCCACCTGC
12651 CCTCAGCCAC GTCCCACCTA TCCTTGGCCG CATCCTGACC CGCTGCCTCC
12701 CGTGTTTCCT CAGGAGTCTT CTGACAGTGC CAATACCACC ATAGAGGATG
12751 AAGACGCTAA AGGTACCTGC ACTTGAGTCC TTGCCCCCCC AGCGGCCTTG
12801 GCATTGCTGG GTTGCTCTTT GAGGTGGGTG GGACTTGGGC AGGGTCAACT
12851 CTCCTGCGAC GCCTAGTTTA TGCATGTGTT GAGGGGCTCA GGGACCCTGT
12901 AGCTGTAATC CTGCTCCAAG CCTGGGTGTC AGGCCTGCCC AGAGCGGAGA
12951 AGCATGGCAG AGATGACCGA CAGCTGGGCA GTCTCGGTCA CCGCATCCAA
13001 GTGAGGAAGC CACGGCTTTG CATGGAGGCA GGTTCTCCAC ACCAGGACCC
13051 TCACGGGGAA ACAGGCCCAT GGGTAGAATT TGTTCCAAGA TGCTGTCCTT
13101 GTCTTAAAGC TCCTTAAGCT TGCGTTTCTG TCCAGCATGC ACTTGCCAAG
13151 TGGCCGGGCA GCTGGGTGAG TGTTTCCGTG TTTGCCTTTG CTTAGCCAGG
13201 AGTGTCCTGC TGCGGTGGGT TTCTGCACCA CAGATTCCAG GGCCCCCTCC
13251 CTTGCTCACC CAGGCCAATG TCTTGTGTGT TCCCCAAGAG GCCCCCAGGG
13301 CACCAGGCAC TGGGGCATGC TCCATGGATT CTGCCGCCTC CAGACCACCC
13351 ACATGGGGCC TCCTGACCCT CATCGCTCAC ACGGTCACCT AATAAGCCTT
13401 ATGCTGTTCT CAGGGCTACC CTGGTGCCCA AAAAGGGTCA GCCACTCTGC
13451 CAGTTTAGGG GAGAAAACTT CTCACCTGTC CAAAGCATAG CCTTGCTCCT
13501 GCCCGGCCTA CCCAGCTATG ACACTGTCCC TGAGCAGAGA TGAGCACAGG
13551 ACTTTGGGCC CTGGATGCCG GAGAGTGGGT GTTTGTGTGA TTCCCCTGCA
13601 GTCTGGAACA GGCCCCAAAG GCAACAGCAT GAAGGCTGTC CAGAGGTTCT
13651 CCATCACCCT CAGCCGAGTG GGGTGCTGAG CAGTGAGGGA GGGGACCTGG
13701 GAGGGGGGCC CAGCCTGGAT CCTGCAGGGG AGAAGAGAAG ACAGCCAGAA
13751 GCCAGCAGCT GTGGCTCAGA TCTGAGCCCG AGCAGCCTCT CGAGGTGGAG
13801 GCAGACACCC CCCACCCCAC CCCGTGCAGA AAGAAGCCTT GCCAGCCTGC
13851 CCTGAGGCTG GTACAGAGTC CAGGCAGGCT CAGTGGCCAT CATGCCCCTA
13901 CGATGACTGT CACTCCCTCT CCGTGCGCCT GGCCTCTGCT GGCTCTGGCC
13951 AGGGGTGGTC ACAGCACTAG GGTGGCAGGG TGGCCTCTGA CTCTGCGCCA
14001 GCCTGCACTG GCCTGTGCTG CCCTGGCCTC TGCTGGCTCT GGCTCTGGCA
14051 CCGGTCCCGT GTTGGCTCCT TCAGCCTTCA CATACCTGCT GCGGCCACCA
14101 CAGGCCCAGG ACCCCACAG GGTGGCCACC CCACCTCCAC CCCCCTGTCC
14151 CCAGGTATCC AGCTGTCACC CCCTCCCTCC CTCCTGGCCT CCCCCTGCCT
14201 TTCTCCAGTT GCCTTCTTTT CCTGCGGGCG CACCACCCAC CTGCCTGCCT
14251 CACCTGTTCC GCCTCAGCCC CCAGGGTCCC CGACATCCTG AGCTCAGTGA
14301 GGAGGGGCTC GGGAGCCCCA GAAGCCGAGG GGCCCCTGCC CTGCCCATCT
14351 CCGGCTCCCT TTAGCCCCCT GCCAGCCCCA TGTAAGTAGC CTGGGTCCTG
14401 CTGCTGTGGG GGTCATGTTG GAGGGCTGGC AACCCCCTAG AGGGGCCACT
14451 CCAGAGCCGA GGGCAGGCTG AGCGTGGACC CTGGCTCCAG CCTCATCACC
14501 CCACAATCCC TCACTGGGGC TTTCCAGGGT GGCCCAGCC CATCGAGCCC
14551 CACCTCTTTG TGAGGAGGGC CCTGGACCAC TTTCCTGCTC AAGGCCACTG
14601 GGCAGGATGG GAGGCCCTGG AGGCTCGGGC CTCAATTCCA GTCTTCAGGG
14651 TCGGTGCAGG CCTCACTCCA CCTCAGCTTG CGGGCGGGGG GGCTCCCTGC
14701 TATTGAGGCA GGCTCTGATT CAGGGCCTGA TCCCAGGGCC CAAGGGGTCT
14751 AGAACACGGG ACCCCTCCCA CTGGCCTCCT CCGCCTTGCC GCCGCCTCGT
14801 GTGTCTGTCT GCCTCATGTT CACGTCTCAT CTGTTCCACC CCAGCCCCA
14851 GGGATCTCTG ACATCCTGAA CTCTGTGAGA AGGGGTTCAG GAACCCCAGA
14901 AGCCGAGGGC CCCCTCTCAG CGGGGCCCCC GCCCTGCCTG TCTCCGGCTC
14951 TCCTAGGCCC CCTGTCCTCC CCGTGTAAGT AGTGGCCCCC AGGCCTGCCG
15001 CCTCTGCTGC CGGACAGCTC CCTGCGAATG GCCGGCGCTC AGCAGCTTCC
15051 CACCTGCATG CACGGCCCAG CTACCCTGCC CCGGCGCCGC AGCCTGGAGT
15101 CCTGCCCTGG CGGGGCTTCC TGTGGGCTCC CATGCTAACC AGCAGGGCAG
15151 CTCCTGGCTT CTCCCTAAGG GGCCCAGACC CCTCCACGGC TCCTGCTCCC
15201 ACTGCCACTC CCCGCTCGCT GTCCAGCCCC AGGCCCCCCC CCAAAATGTC
15251 TGTCCCAGCC CTGGGCAGCC CTGGCCCCTC CGAGGCCCCC CATGCCCCTA
15301 GGCCCTCTCT GCTGATCACT GTCCCAGCCC CACAGACTTC ACACCCACCC
15351 AGGGGCCCTG CCCATGGTGC CCAGGAGCTG CACTCAGGGC CACCCTGGTT
15401 CCTGATGTGG CCCCAACCCC TGAGCACCCT CCCTCAGTCT AGGAGGCTGA
15451 GGAAGGTGCC AAAACTGGAA CCCCGACCAG GGTCTCTGGA GCTCACCAAC
```

FIGURE 3E

```
15501 AAGGGGATAG TACGGAGAAT CATAAGCCTG GCCTCTGCTG ACCTGGGCTG
15551 TCCTCATGGG GCCAGGCCAG GCCTCCTCTG TAACGCCCGT GACTCCCTCC
15601 TCTCCCTGTA ACCCCGTCCA GCGTTCCTCA AGGGCCACTT ACCTGACAGC
15651 TTCTTGCTGG CCAGCAGCCT CTCCCTGGAG GGTGCCCTCT GCCCCCAGCA
15701 GCTTCAGCCC ACGCCACCCG ACAGCCAGAG CATCTGCCCT TCACTCCTGC
15751 AGCCTCCTCT CCACGCACCA CGCTGTCCGC AGCAGCACCC TCTGTCCCCC
15801 TGTCTCCCTC CGTCCCCCA TATCCCCTC GGTCAGCCTA CAACCTCTCC
15851 ACGTCCCCCT AAGTCCACGC TCTATCCCTA CATCCCCCTC TGTCCCCCAA
15901 ATTCCCCTCT TTCCCTCATT TCCATTTTCC TCCCCAAACT CTGCTCTGCC
15951 CCTCACATTC TCCCTCTGTC CCCCACACCC TCCTCTGTCC CCCACACCCT
16001 CCTGTGTCCC CCACACCCTC CTCTGTCCCC CATATACCCC TCTGTCCCCC
16051 ACACCCACCT TGGTCCCTTG CACGCCCTTT TCTGTCCCCC ACACCCCCTC
16101 TGTTCCCTAC ACTCTCCCTC TGTCCTCCAG ACCCTCTCC CTCTGCCCCC
16151 CTCCCTCTGT CCCCCACACC CCCTGTCCCC CACACTCTCC CTCTGCCCCC
16201 CAGACCCTCC TCTGTCCCCT ACACTCCCTC TGTCCCCCAT ATCCCCTCT
16251 GTCCCCCACA CCCTCCTCTG TCCTCCACCC CCTGCCCCCC ATACCCCCTT
16301 CTGTCCCCCA CACTTCCTCT GTCTTCCACA CCCCCTCCTG TCCCCCACAC
16351 CCCTCTGTC CCCCAGACTC TCCCTCTGTC CCCCACACTC CGTCTGTCCC
16401 CCACACCTCC TGTCTTCCAC ACCCCCTTCT GTCCCCACA CCCCCTCTGT
16451 CCCCCATACT CTCCTCTGTC CCCCACCTCC CCTCTGTTCC CCACACCGCT
16501 TCTGTCCCCC ACACCCCCTC TGTCTTCCAC TTCCCTCTG TCCCCCACAT
16551 CCCCCTCTGT CCCCTGCACC CTCCTCTGTC CCTGCACCC TCCTCTGTCC
16601 CATGCACCTC TCTCTGTCCC CCACATCCCC CTCTGTCCTC CACACTCCCT
16651 CTGTCCCCCA CATCCACCTT GGTCCCTCA CGCACCCCA TCCCCATGA
16701 CCCCTTCTGT CCCCCACACC CCCTCTGTCT TCCACACCCC CCTCTGTCCC
16751 CCACACCCAC CTTGGTCCCC TCATGCCCCC CATCCCCTAC ACCCCCACTT
16801 TGTCCCCCCA CATGCCCCTC TGTCCCCCAC GTTCCCTTCT GTCTCCCACG
16851 TCTCCTCCAT TTCCCGTTTC CCTCTCTGTC CCCCAAGCTC CCCTCCATCC
16901 CCCACATCCC CTTCTTTCCC CTATATCCCC TCTGTCGGCC CAGGTCCACC
16951 ATCTTCCCCC CACACCCCCC CATTCTCCCT TCCTCCCCTC TGTCCCCTTG
17001 TGCCCCATCC CCCACATCTG CCTCTGTGCC CCTCAATCTC TGGCTTGGCT
17051 GTCTGCCCAT GGTTTCTCTC CTGCGTGCCC CCCGTGCCTG CCTTGTGTTC
17101 ACGTCTCGTC TGTTCCGCCC CAGCCCCAG GATCTCTGAC ATCCTGAACT
17151 CTGTGAGGAG GGGCTCAGGG ACCCCAGAAG CCGAGGGCCC CTCGCCAGTG
17201 GGGCCCCGC CCTGCCCATC TCCGACTATC CCTGGCCCCC TGCCCACCCC
17251 ATGTAAGTAG CACCTTGAGT GGCCGTGGCA GCGGCTGCCT GGAGGGGCTC
17301 GGGGCGTGCG AGCCTGGCAG TGGTGCTCTG GGAAGGGCCA TTCTTGCGGA
17351 GGAGGGCGGG GCACAGGATC CCTCTGCTGG GTCCCAGGGA ATTGCTTTGA
17401 AGCACATGAA GGTGCCACTG GGTCTCAGAA AATGGAGGTT ATGGTTATGA
17451 AGTGTGTATG ACATATGTGT ATAGGAAGAG CGTCCGAAAG AGCAGGTTTG
17501 TTGCCGACCC CAGCATTCGC AACCCTGAGG TCCACAGCTT TCTCCTGATG
17551 GGAGGGGAAT GGGTGGCAAA GGGTCTGCGC GTGTGGCAAG GGCTAGCACG
17601 CCAGGAGCTG CTGGCTTGGG TCAAGGTGGA CCTGCTGGGC CGGGACAGAA
17651 AAGTGTCAGT CCCGGCCTGA GACGCTCTAG CATTAGAGCT GTCCAAGTCC
17701 AGACAGCAGG GAGCAGGTGG GGATCGGGAG GCGCGGATCT GGGGGGCAGC
17751 TGGGGCCAGG CTGAAACAGA GCGGGCGGGA CAGGAAGCAC AGGCTGGGCA
17801 GCCTCCCCGG CCAGGGAGGA GCCAGGCTGG GCCACCTCCC GGTCTGTCTG
17851 CCGACTACCC GCAGTATCAC TTACAGGGAT GGATGACATC CCAGGGCTGC
17901 TGCCACCCCC ACCTGTGGGG AGACACCAGA CTGGGGGTGG TGTGGAGATA
17951 CTCTTAGAGA AGAGGCTGCT GGGCCACGGG CTCGGCATGG CAGGGCAGTG
18001 GCTAGGTAAG TACTTGAGGG ACAGGTGGGG TCTGCTTGCC ACCGTCCCT
18051 CTGCAGGCTG GGCCTGGGGG CTGCTGCAGG CGGCCAGGGC AGAAGGGTGT
18101 GGGGAGAGTG AACCCACAGG AGCAGCGGCT CGAGGAGGGG GATGCAGGCT
18151 GCAGGCTCAA AGGGGCACTG GATCCACCCT GGGTGCCCGA GAGAGCAGGG
18201 GGCAGCCCCT GGAGGGGTAC TCAGGGCAG AGCTTCTGTG GTCGGCTGAG
18251 GACCCCAGC AGGGGTTGAC TGAGGGGATC AGAGGCAAGC AGCTGAGGGG
18301 AGAGGCAGG TTCTTGATGC TGATAGGGTC GGGGTGCCTG GGCGACCAGA
18351 ACTCAAGGAG GGAGGCATGG GGAGGGGCCG CCGTGCAGCT GGGGTGGGTG
18401 CACCGCAGGA CCTCTGGGAG TGGTCAGAAC CCCCGACACC TGCCACTTCT
18451 ACAGCAGCTC ATCTGATTTT AAGGGGCTTG CTGCCCTTGC AGAAGTGGAG
18501 GGGTGTGCCC AAAGGAGCCT GCCTGGAAGG TCACCCCATC AGGTTGGCAT
18551 GACCCCAGCC CAGGACTGCA GCCTGCCCTC AAGGTCTGTG CAGTATCTGG
```

FIGURE 3F

```
18601 GGTGAGTCCT CTGAGGACAG GGCCCAGGGT GGGTGTGGAG TGGCCAGCTC
18651 GGGGCTCGGT GTCCAGGCTC ACCTTCAGGG GCCACAGCAC AGACCTGCCC
18701 TTCCAGAGTC TTCCCTGAGC TTGGCTGGGG AGGAGGGGGC TGCAGGAAGG
18751 AGCTGTGAGC AGGGCAGGAT GGAGATTCGT GTGGCCCTCC TGGGAGGGGC
18801 TGGGCAGGGC TGGGAAAGGG GTGGGTGAGA TGTTCCGGAA CTCAGGGAAA
18851 GGAAGAGTCT GGGTACTGCC CTGGGGGCAC CTGGGCCCAG GTGGCAGGTG
18901 GCCAGCTTTC TGCCTCCTTT CCACCTCCTT TCTCCAGAAG GCACCCACCA
18951 GCTGTGTAAA TAGGGCAGGT GCCCACGCC CGCCTCAGGC CCCGTCTCCT
19001 CCCCACCCAC GCTCTCTAAT CGCGGATTAT ACACAATCCA GCCTGATCCC
19051 TGGGCAGCTG CCCTCCCTCC CGCAGCCACC TCTGGCTCTG AGAGATGGGC
19101 TTGGGGCCAG CCTGGGGTCC CAGGAGTCCA GGCCAGGATG AGAACCTGCT
19151 CTGACCCCAC CTGGACGCAT TAGGCCTGCC TGGACCTGTT GCCTCACCCC
19201 AAGAGAGCCA CAGGCAATGC AAAGGCTCCT GTTCATGTCA GGGCACCTGG
19251 AAGGCCTGAC TTGCAGAGGC TCTTGGCTCG TGCAGACCCC TCCAAGCCCA
19301 GGCCCTGCCC ACCACCTCCC CTTTGTCTCT GGAACTGCCA GGACAGCTTG
19351 TCCTCAGCCA GCAGGTTTCC CGACCCGGGC ACCTCTTCAT GTTGGGCCCC
19401 CCTCCTTTCC CTCCATCAGG GATCATGCCC TTCTTCAGGG GCCTGGATAT
19451 CAAGGACACA AAAGCTCCCA TGTGCTATGT GGGGAGGCAG AGTGGGGGCT
19501 GGGTTGAGCT GGGGTCTGGG CAGCGCCATT CCGCAGGGCA GGGGCAGCCT
19551 AGGCTTCCCA TCTGTGGAAT GGGTGGGTGG GTCTCACAAC GGACCTGCTT
19601 CCCGTACTTC AGCACGGTTA CCACTCTTGA TTGGAACTCT GACCATGCAT
19651 CTCCTCTTCT GTTTACTTCA CGCTTTCTCT TCCCATCAAC TCCCATTTTA
19701 ATTACAATTT GTTTAAAAGC ACTGCATATT ACTTCATTAA ACAGAAGATT
19751 AGTTTCACTT ACCATTAGTG TAAGGTGACT ATAGAACCAA AGCAGACTGG
19801 AAACCAAATG ACATAATGTC ATTCTCTTCT CCATTCCAGC TGCCTGCTGC
19851 TGTGCGCCTG AGAACCCCTG TGGAGTGGGA GGGGCAGCTG TCTCTGTACA
19901 TTAGAAAGGG AGGTTAACTA AGTGACAGGA GGTGTTTGGG ACATGTGGAC
19951 ACCAGACTTC TCTCTTGATG CAAGGAGGGC AGAGCCAGGC AGCCTAGTGG
20001 GGGCTGGCTT GGGGGCTGCT GGAAGGACTG GCTACAGGTG GAAGAGAGGT
20051 CAGACCTGAA GCTTGGGGCC ACCTCCAGGA AAGGACAGGT GAAAGTGGAG
20101 GCATGAGGCA GGGGAGAGGC AGGTGCCAGG CAGAGGGTGG AGAGGAGGCA
20151 GGAACATAGC AGCTGGGGCG GGGGCGGGCC CTCAAGTGTC ATATGCTACT
20201 TTCCTGGGGC CCAGGGGCAA GGACAGGAAC AGCCACAGCA TGTGTTGGGA
20251 CAGAGCCCTG TGCCTTCCTA GAGCTGGGCA GGTGGAATGG GGCAGGAATG
20301 GGACTCGTGG TGGCTGCAGC AGGAACTGGA GGGGAAGGGG CTTCTGGATC
20351 CTGCAGCCTA CCTTCCTAGA GGCCAGCTTT CCGGGGTCCA CCAGGTGGGT
20401 GGGAACTGGG CTTGTGTAGC AAGACTGCCC TGAGGACCAT CCATGACATG
20451 GTCTAGATGA AAGTTAGGAA AGAAAGGGAG ACAAGCTGGC AGCAGAAGTA
20501 CAGCTGGGTC AGGAGCAAGG GCCTTTCCAG ATAGGGACAA CCCAAGAGTG
20551 CACATGTGCC CACGCCACAC AACACAGGCA CACGACAC GTGCACGCTC
20601 ATAGGCACTG CACACACACA TGCACAGGTG CTCATGCATA TGTATGAGCT
20651 TCATCTACAC ACATTCACAT GCCGTCCTGC TTATGTCAT GTTTCCATAC
20701 ATGCACATGA ATGCACAATC ACGTGTACAC ACATGCATGT GATCACATAC
20751 ATGAACATGT GTGCACCCCA CTCCTCAGGT GCCATCGGGC TCCTCCTGCT
20801 GTCACTGTGC AGCAGGGGAC ATGAGGCCCC AGAGCAGACA GGTGCAGCAC
20851 AGGCGTTCCC AGGCAGTGCC CCACACACAT GCATGAGCAC ACCCGGGCAT
20901 GTGGCGCCTC CTTTGTGGAC TCAGTCCACC TGCCAGGTGG GCTCCCTGGT
20951 GGTGTGAGCT CCCAGAGGTC TGGCGAGAGA GATAAAGGCA ACCCCACCAC
21001 CAGGCGTGCT GAGAATTCCC TCTTCTGGCT GGGCACAGTG GCTCATACCT
21051 GTAATCCCAG CACTTTGGGA GGCCGAGGTG GGCAGATCAC TTGAGGTTAG
21101 GAGTTTGAGA CCAGCCTGGC CAATATGGTG AAACCTCATC TCCACTAAAA
21151 ATATACACAC ACAAAAATTA GCTGGGTGTG GTGGTGTGCA CCTGTAGTTC
21201 CAGCTACTCG GGAGGCTGAG GCAGGAGAAT CGCTTGAACC TGGGAGTCAG
21251 AGACTGCAGT GAGCCGAGAT CATGTCACTG CACTCCAGCC CGGGTGACAG
21301 AGTGAGACTC CATCTAAAAA AAAAAAAGAA TTCCCTCCTC TGGGAATTTA
21351 GACCACAGAC AGGTTGCATG TATGTGGCCG TTGGAGGCAG CACTCACAGC
21401 AAAGAGTGGA AACGTCACCA CAGGGCCTGC CTTCTGGTGA AAATGGTGTC
21451 CTGCAGGGCG GGCAGCTGTT TGAGGGCAGG TGTCCCAGGT GCGGCCTGCA
21501 GCAGCCTGAG GGTCACAGAG CGCAGTGCTG GGAGTGCAGA GACTTCCCCC
21551 ACAGGGAGAG TTCCCAGGAA CCTGCTTCCG GTGCACTTCT GGGGGTTTGA
21601 GTTTTTTCCA CGGACGAATT ACTTTGAGAA ACCACTGTTA CTCGTGTGTA
21651 TAGGTGAGCG TGCGTGTGCA TGTGTGTTCT GTGTGTGAGT GTGCATGTAT
```

FIGURE 3G

```
21701 GTGCGTGCCT GCGTATATAT CCTCGCAGAT ACGGCTAGGG ACCTCACTCA
21751 GGACAGTAGT TCTGCCTGAG GAGAGTGAAT GCGGCAAGAT TGAGGAGAAC
21801 ACAGGCATCT TCAAACTACA TGTGCGGTGC TTTATTTCTT TAAAAATGCG
21851 TCTAAAGCAA ATAGGAAAAT GTTAAGATTT GAATCCGTAG AGTGTGGGTT
21901 CTATTATTCT CTCCACATCT TCCATACGTT TAAAATCTTT TGCAATGAAA
21951 ATAAGCTGTA GTTAAAGCAG CAATGCAGGC TGCCAGTGAG CGCCCCGGAG
22001 GCCAGTGAGG ACCAGCATGG CTGGGTGGCC TGTTGGAATC CAAGGGGGGC
22051 GGGCAGGAGC TGCAGGCAGG CGCCCGGGAG TAGCCCGGGC ATGGGGTGC
22101 GGGGCAACAG GGATGTCTGC AGGGGTAGCA TGTGGGCCCC GGACTGCAAG
22151 CAGGTGGAGC CAGCCGGATG CGGCTCCTAT GAGAAAAGCG GGGAACAAGA
22201 GACCACGCTC GTTCTTCCTG CTGCGGGGAC AGCCCTGGTC ATCGCTCCGG
22251 GGAACCCTGC AGCCTGCGCC GCACGTGGCC GCCCCTGCT GCTTCCTCCT
22301 CCCCGGCCTC CGGGTGGCCT TGCTGACGGC TCCTTCTCTG AGGCAGGTCT
22351 CTGCCTTCTC GCCTGGTGCC TGCACTCAGT AGCCCCCTCA CCAGAGCTGC
22401 TGGGTGAAGG AAGCACTAAG AACCCAAGGC TCGGGAGGAG AGTGGGGCCG
22451 GGAAGCTGCA GGGAAGCGCA GGGCCAGGCC TGGTGGGCCC AGGGGCTGGC
22501 TCACGGGAGG GCAGGAGGGA GACTGTGGCG GACAGCACGT GGGGCCAGGA
22551 GGTGACCTCC AAGTGGATTG TGGGTGGGTT TTTTGTCCTC TTTCTGCATT
22601 TTCCAGGCAT TTTGTAATGT GGATAGAATA TTTCTGTTCT TCAAAAATAC
22651 TTTAGTTAAG AAAAATAAGA TGGAAGCTGT TGCACTTGAA AATGAGGAAG
22701 CCACTGGTGA TGCAGGGGGG GCGGCGGAGA GGACCTCTTC TGCAAATAGC
22751 GGCAGGAACA CGGCATGGAT GCAGCTCGCG CTCCCCCAGG CCCTCCCCTG
22801 GGCTGTGTGG AGGGGTCCGG GGGGAATGGG CCAGCGCCCA GTGGTCACCT
22851 GGCCATGTCT CCCCACAGCC CGGAAGCAGG AGATCATTAA GACCACGGAG
22901 CAGCTCATCG AGGCCGTCAA CAACGGTGAC TTTGAGGCCT ACGCGTGAGT
22951 CCCTGGGGCT GGGGGGGGGC TGTGCAGGAC AAGGATGTGG GACCCTTGGG
23001 GGGGCCTGCT CAGAGTCAGG GGTCCACGGG GCCCCTCCTC ACTTGGATTT
23051 GGCCCCCAGG AAAATCTGTG ACCCAGGGCT GACCTCGTTT GAGCCTGAAG
23101 CACTGGGCAA CCTGGTTGAA GGGATGGACT TCCACAGATT CTACTTCGAG
23151 AACCGTGAGT GAGGAAGCCC GGGTGGGCAT GAGGGGCGG TGCCCCCAGG
23201 AGAGCCTCTC GGCCCCTCCC AGGGACAGCA TGGTGGCTGC CTATGGAAGC
23251 CCTGTCCCCT CTGTGCCCAG GGTTGGCCAG CCACCTCTCC CCCGCCAGAG
23301 GCCATACCCA GCCCCAGAA TCCCACTCTT GGAGGGCCC ATGCTGCTCC
23351 CAGGAGAGCC GAGCCTCCCC AATAAGGGGA GTTGAGAGAG GGAAAGGATT
23401 AGGCTGGTGG GGTGAAGAC GGGCACCAGG GCAGTCATGG TAACCCGAGA
23451 CCCCCGCCCC GCCTGCTGTC CACAGTGCTG GCCAAGAACA GCAAGCCGAT
23501 CCACACGACC ATCCTGAACC CACACGTGCA CGTCATTGGA GAGGATGCCG
23551 CCTGCATCGC TTACATCCGG CTCACGCAGT ACATTGACGG GCAGGGCCGG
23601 CCCCGCACCA GCCAGTCTGA GGAGACCCGC GTGTGGCACC GCCGCGACGG
23651 CAAGTGGCAG AACGTGCACT TCCACTGCTC GGGCGCGCCT GTGGCCCCGC
23701 TGCAGTGAAG GTGAGTGTTC TGTGCTAAGT GACAGCTGGG GCAGAGGGT
23751 GGCGGTGGTG TGAGTGGCTG CAGCCTGGGG AGGCGATGGG GAGCGGTGGG
23801 GCCTGTGGCA GAGCCCATGC CTGGGAAGTC CCTGAGCTTT CCTGGTGAGG
23851 CCACAGGAAT GATGTCAAAT TAGGGACCAC GGCAGGCTGG GTGTGGCAGG
23901 CCTCCCCAGA GGACTGGGGA GCTGGTGAGG GCCTGAGCAG TCCACACTGG
23951 CCAGAGCTGG GTGGGTTGCA GGTGGATGGG CCCCGGGCAG CACAGTCCTG
24001 GGCACCATGC CCTGTTTGTG AGGACTGTTA GAGCCCCAGA TGGGCGTTCC
24051 CCAGGTGGTG GGTGCAGCGG GCCCAGAGCC CAGTGAGTGGGC CTTTTCTGG
24101 TAATTGGGTT GGGCACCTTG AACCTCTCTC CCGAGTGGGC CCTTTTCTGG
24151 ACTTTAACCC TCTCTGCAGT GCCGCATGGC AGACAGCAGA GCCTGGGGGT
24201 GGATGGGAGA GGGGGCTGCT GAGGAGCTGA CCCACCCGCC CCATTTCAGA
24251 GCTGCGCCCT GGTTTCGCCG GACAGAGTTG GTGTTTGGAG CCCGACTGCC
24301 CTCGGGCACA CGGCCTGCCT GTCGCATGTT TGTGTCTGCC TCGTTCCCTC
24351 CCCTGGTGCC TGTGTCTGCA GAAAACAAG ACCAGATGTG ATTTGTTAAA
24401 AAAAAAAAAA AAAAAAAAAA AAAAAACAAG ATGACGACGA CAACCACAAA
24451 AAAAATTGAC ATCAGATGAA ATGAAAAAAA AAAAAAACAA AAAAAACTAA
24501 AGGAAGGAAA AAGCTGTAAA AATCACTGGC ATTCGTGGGG CCACTCCCCA
24551 CCCAAGCTCC ACGTGTGTCC GTCTGTGCTC CTGGCCTCTG GGGGACCAGC
24601 TGGGACATGA ACTTGTCTGC CAGGCCCCG TCGCGTGCTG AACGGTGTTA
24651 GTTTGTAGGT AACGCACACA CCCCACACCT AAGGTGTCTG CATCCTCCTG
24701 CCAACGCATG GGCTCCACGT GGTGTGCTCG CTGGCTGTCG TGACTGTCAG
24751 CTGTCTCTTG GGAGGGGCTG TGGGGCCCG CTGGGCTGCC TCCTTTCCCG
```

FIGURE 3H

```
24801 CTAGTTGTGC CTGAGAGTTG CTGTTGTTCC TGCTTTCCCT TCCCTTCCTT
24851 TCATCCCCTG AAGGGCTAGG TGTGGGTTTT CCGTGCCCGG TATCCCCACA
24901 CACCCAGCAC GGACAACCCT TCGGCAGAGC CCAGGCCGGC CCCTCACCCC
24951 CTGGAGTATT GAAACTGGAG TCCCGTCCCC AAGGCCTTCA GAGATGCCCC
25001 TACACACCCA GGGCTCCAGC TCTGGTCCTT CTGGGGGAGT AAAGTGCAAA
25051 GAGGGGCACA GCTTAGTTTT GGGCCTCTCG CCGAGCAAGA GACAGCACTG
25101 CTGGCTACAG CTCCAACACA GCCAGCTGTG GCAAGAGGAC TCTGCCTGGG
25151 CTGGCCCCCC TCCTGTGTGA GGTGTCTGTC CCTTCTCTGC TGGCCAGCAG
25201 CAGATGCACT GGCAGCTCCC AACCCTGTTT CCGCCCCTCG GCCCTCCCCC
25251 AGCCTGTTCG GCTTCTCTGC AGCCCGCAAG GGGGAGCAGA CTTTTGACAA
25301 AGGACTGCGG GCCTCGCTCA AGTCCCTGAG CCCCCAGCTG AAGCTGGGAG
25351 GGGAGGCCAG GCTTTGTGTC TGGGCATATT CGTCTGCTGA TGGGGTTTGG
25401 GGAAGCCTGG GGCTTGGGGT TTGGTCGGGT GGTGCAGCTA GTGGCAGAGC
25451 GGGATCAGAG GTGGTGGCTG CCCAGCTTCT GGGCTGAGAC AAGGGTCTGT
25501 GCAGGGGTTT ACTGAAGTGG GAGTGCCTTT GGAATCTGGG CCGGGAGCAG
25551 AAGGGAGCAA AAGCTACAGT GGGAGCCAGC CTAGGGCACA TGGGAGGCGT
25601 GAGGGCAGTG CTGCCCGTGC AGTGTCAGGT GTGCCAGTGC CTTGGCGGGC
25651 TGCAGTGCGT GTGAGGGCAC CTTCTAGGTG GGCCAGGGAT GCAGCTATGG
25701 AGATAAGGCG GGCTGGGGAC AGAAACAGGT GGGCACAGGG CCCAGGACAC
25751 CAGCGGATGG AGGGCAGGGT CTAGCCCTGT GCTCCTGAGC GTCGGCTGCC
25801 TGGGTTCGAG GCGGTGGGTC CCCGGCCCCT TGTGATGGTG TGTACCATGG
25851 GGGAGCTCGG GGACAGGGCA AGCCCGAGCA TGGTGGGGCT GCAGGGTGGG
25901 TCTGAAGCCA GGTTGGGTGG GGGTGGTCAC AAGCCCTGAC TGCAGAGGGT
25951 CAGGGGCTCC TGCCCAGTG CCTGCCCACT TTCAATTCAC ATTGTTTTCA
26001 ACAAGGATTT TCTTTATCTT CCCCTACAAA TCAAGCCAAG GGAGGGGCAC
26051 AGAATGGGGA ACAGGACACA GGATCCTAAA CTCCAAGGGG ACTGTCCACC
26101 GATGAACACT CAGAGTGGAC ACCATCTTCC GTCCACGCTG TGCCCAGGAC
26151 AGCTGTCCCC ATCCATGAAC ACAGGGTAAA CATCTGCCGG GCTCCGCACC
26201 AGTGGCTCCC TGGGCCATGG GACAGCGGCA GGGCTCACCA CGGACAGCAC
26251 GTGGCCCAGC AGCCGGCCAC CCTGGCGTCC TGGGGCCTCC TCCCCTCCTC
26301 TCCCTCTCAC CTTGTCACCT CCACGGAGCT GCCTGTCTGG GATAATTTGG
26351 GGATTTTTTT TCTGGGGGAT AATTCTTTTG CATGACCCCT AAAGAGCAAG
26401 CCACACCGGT CTGCTAGCTA GGTGTCCGCG GTGTGGTGGT GGCGGCCGCT
26451 GGCCAGCGCT GCAAGGGGTC GGCTGCCCAC GGTGCTGGCT GGCCTCCCCT
26501 CCTCTCTCTT TTTGCTGAGT TTCATTGTCT TTTCTTTCTG AGCCTTGTAA
26551 GTGTACAAAA ATTATTCTTA TTTTGTTCTG TCTCGGGAAA CTGCAAATAA
26601 AAGAAAAACA GGACAAACTG CTTCAAGTGC AGCTGGGTGC TTTAGCTGGA
26651 ATCCTGCCGA CCTCCTGCGC CAAAATACAG ACTCAAGCCC GGTCCCTGGC
26701 CAAGACCCTA CTTGGGCCCC TCCTCCAATG AAAGGTAGTG CTATGGGAGC
26751 CCTGAGCTGG CCCTGACAGT CCTGAGCCCC TCTAGGGTGA ACGGCTCACC
26801 CCAGGTAGGG CACTAGTCAT AGATCATAGC TCTACCAGCT GTCTCCACCT
26851 CTTCCTCTGG TCCTCTGAAG TCTTCTGGGC CCAGCGCTGT CCACCCTGAA
26901 TGCTGGAACT GAAACTGGAT CCCAGCCCCC AACACCCCTG ACCTCTCCAT
26951 TCACCCCCGG TGGCCGCTAA GGATGTGGCC AGGGCAGCCT CTGGGCAGGA
27001 AGGAGCCCCA GGACCAAGAC CTCTGGCTGT CCTGCTGTTT CCTTCCGCCC
27051 CTGCTACATG TATTGGCTAT TCTGGATGCT GAGGACACAC AGTGACCACA
27101 GAGCCGGGCT CCACCCAGT GGATTATGCA GACAGATGGC ACGCAGGCCT
27151 GTGTGGACAT CAGCCTCGGG CACCAGACAT AGGCAAGGCG CAAGGTGATA
27201 CAGTAGGCAG CCACCATGGG GGCAGGAGG CTCCAGCAGA GGCCACACAA
27251 CCAGCCCAGA ATCCAGGACA GAGAGCTGGA ATGGAGACAG GGAAGCCAGA
27301 TACCAGGCCA GACTGGCCAG GTGCTACAGG CCTGTGGGCC AGGCCAGGCT
27351 TGGGACTTC GTCCTGGGTG TGAAGGAGAC AGGCACCCCT GAGGCCTTCC
27401 CTCTGCATCT CCAGCCCAAG CTAAGCGCAA ACTCTTAGGT TGGAGTAAGG
27451 AGTAACCCCC TGCCAAGTTT CTCCTGTCCT CAGGCTCCAC CCACCACCTA
27501 TGCTGCCTGG CCCCATGGGG CACACGCTCA GGCCCAGCCT GGGAAAGCAA
27551 CTGCACCTGC CTGTGCTATG CTGGCCCTTC TCAGCCTCAA TGCCCTCCTC
27601 CCTCCCCGAC GCACCCTCGT GGCCCCCGCT GGGCCCCCTG ATGCACCCTC
27651 ATGTCTCCAT GGCAACCTGC TCAGAGTGTG GCCCTGCCCT TGGCTCCCCT
27701 CCACACCTGT GTCCCAGGCA GTGCCACGGC ACTTTCCTAA ACAGAAGGAT
27751 GGGCTTCAAA ACAGTCCCAG ACACTAAACA CACCTGCATT TTGGGTCCAA
27801 GTAACTTCTG ACAAGACGAAG TGCCCCTACA CACCCTCAGT CCTATCCACT
27851 ATGGGCAAGG AGCCTGAAGG ATCCCCCAGA ACTGGCTAAA GCCCTCAGTC
```

FIGURE 3I

```
27901 TCCTCCTCCA CCCTGAGCAC CTTCACGCGG CAGAGTGGCC CTGGATGTCA
27951 GCTTCTTGCT CCCCATGGTC TGCACCTGGA CAGGTGCTCT CAGGTGTGTG
28001 GGTGGGCAGG TGGCAGGTCC CAAGAGCCAG GTGCAAAGAA TCTAGGCCAG
28051 TGCCCACGAG TGCTGCAGTG TCTGTCCCCA GCATGGTATC TAGGGCTCCA
28101 CTTGCCTATC AGCTGTAATC GGAGGAGGCT TTCCAGGCCA GGCCTCCCCC
28151 AGGAAGGCTG CAGGCACTGC GGATCGTGCG CCCTCACATG CATTATTCCT
28201 GAGGCCCTTC TGCAGATGCC ATCAGGGCAG CAACTCTGAT GAGGTATTAG
28251 GGCACAGCAC ACAGGGCTAA GCCACCCTGT ACTGGGCCAA GCGCTACAGG
28301 CAAAAGGAC ACCACCGACG GGCATTTCAT TCATCGCTTT TATTTTTATA
28351 TATTTTTGAG AGGGAGCCTC ACTCTGTCGC CCAGGCTGGA GTGCAGTGGC
28401 GCGATCTTGG CTCACTGCAA CTTCTCCCTC CTGGGTTC     (SEQ ID NO:3)
```

FEATURES:
| | |
|---|---|
| Exon: | 232-340 |
| Intron: | 341-431 |
| Exon: | 432-515 |
| Intron: | 516-1110 |
| Exon: | 1111-1205 |
| Intron: | 1206-1424 |
| Exon: | 1425-1547 |
| Intron: | 1548-1981 |
| Exon: | 1982-2065 |
| Intron: | 2066-3015 |
| Exon: | 3016-3058 |
| Intron: | 3059-4102 |
| Exon: | 4103-4177 |
| Intron: | 4178-9088 |
| Exon: | 9089-9126 |
| Intron: | 9127-9303 |
| Exon: | 9304-9375 |
| Intron: | 9376-10898 |
| Exon: | 10899-10943 |
| Intron: | 10944-12713 |
| Exon: | 12714-12762 |
| Intron: | 12763-17130 |
| Exon: | 17131-17133 |
| Intron: | 17134-22868 |
| Exon: | 22869-22944 |
| Intron: | 22945-23137 |
| Exon: | 23138-23154 |
| Intron: | 23155-23475 |
| Exon: | 23476-23705 |
| Stop: | 23706 |

CHROMOSOME MAP POSITION:
Chromosome 7

ALLELIC VARIANTS (SNPs):

| DNA Position | Major | Minor | Domain | Protein Position | Major | Minor |
|---|---|---|---|---|---|---|
| 487 | T | C | Exon | 55 | H | H |
| 496 | T | C | Exon | 58 | L | L |
| 1662 | T | C | Intron | | | |
| 1785 | T | A | Intron | | | |
| 1889 | A | T | Intron | | | |
| 2416 | C | T | Intron | | | |
| 4698 | A | G | Intron | | | |
| 5424 | C | T | Intron | | | |
| 8722 | C | A | Intron | | | |

FIGURE 3J

| | | | | | | | |
|---|---|---|---|---|---|---|---|
| 9982 | G | A | | Intron | | | |
| 10951 | C | T | | Intron | | | |
| 12603 | T | C | | Intron | | | |
| 14583 | C | T | | Intron | | | |
| 17290 | T | C | | Intron | | | |
| 18188 | C | T | | Intron | | | |
| 19911 | A | G | | Intron | | | |
| 21328 | C | A | G | Intron | | | |
| 21391 | T | C | | Intron | | | |
| 22588 | C | T | | Intron | | | |
| 22965 | - | G | | Intron | | | |
| 23498 | G | A | | Exon | 312 | R | R |
| 23663 | T | C | | Exon | 367 | S | S |
| 25427 | A | G | | Beyond ORF(3') | | | |
| 27727 | C | T | | Beyond ORF(3') | | | |
| 27834 | T | C | | Beyond ORF(3') | | | |
| 28336 | G | A | | Beyond ORF(3') | | | |

Context:

DNA
Position

487
CACCTCTGGGTTTAAACAACATGCACCCTTGTGCCGGTCACCTCCCTGCAGCCGGAGAAC
CTGCTTCTGGCCAGCAAGTGCAAAGGGGCTGCAGTGAAGCTGGCAGACTTCGGCCTAGCT
ATCGAGGTGCAGGGGGACCAGCAGGCATGGTTTGGTGAGTGCCAGGGGCAGGGTGTGTTG
GCTGGCAGTTGGCAGGGCAGGAGGTGATGCTGACAGCCCCTTGTGGCCTCTTCCCCTCTC
TCTAGGTTTCGCTGGCACACCAGGCTACCTGTCCCCTGAGGTCCTTCGCAAAGAGGCGTA
[T,C]
GGCAAGCCTGTGGACATCTGGGCATGTGGTGAGGCCTGGCCTGAGTTGGTGCGGGGCAGG
GCCTCGGGTGTTTCAGGACTTCCCACCTACATCCTGGAGTGTGCAGTGGCCAGCACGTCT
TGCTCTCATCTGGGTTTATCTGTGTCAGACCTGCCCTTGAGCTGCCCTGGCAGGGGTCTG
CCCACACAGCCAAGAGCCCCCTTTCCACCCAGATTAGAATTGCTCACATGAACCTGGCGC
ACCCCAGTGCTCGCCTGCGCTCAGCAGAGGTCTGGTCCAGAAGTGTGGTGGGTGGATGGG (SEQ ID
NO:5)

496
GTTTAAACAACATGCACCCTTGTGCCGGTCACCTCCCTGCAGCCGGAGAACCTGCTTCTG
GCCAGCAAGTGCAAAGGGGCTGCAGTGAAGCTGGCAGACTTCGGCCTAGCTATCGAGGTG
CAGGGGGACCAGCAGGCATGGTTTGGTGAGTGCCAGGGGCAGGGTGTGTTGGCTGGCAGT
TGGCAGGGCAGGAGGTGATGCTGACAGCCCCTTGTGGCCTCTTCCCCTCTCTCTAGGTTT
CGCTGGCACACCAGGCTACCTGTCCCCTGAGGTCCTTCGCAAAGAGGCGTATGGCAAGCC
[T,C]
GTGGACATCTGGGCATGTGGTGAGGCCTGGCCTGAGTTGGTGCGGGGCAGGGCCTCGGGT
GTTTCAGGACTTCCCACCTACATCCTGGAGTGTGCAGTGGCCAGCACGTCTTGCTCTCAT
CTGGGTTTATCTGTGTCAGACCTGCCCTTGAGCTGCCCTGGCAGGGGTCTGCCCACACAG
CCAAGAGCCCCCTTTCCACCCAGATTAGAATTGCTCACATGAACCTGGCGCACCCCAGTG
CTCGCCTGCGCTCAGCAGAGGTCTGGTCCAGAAGTGTGGTGGGTGGATGGGAGTGGAGAA (SEQ ID
NO:6)

1662
GAATTCTTGCCCCTGCCTGAGAGGGAGCTTCAGGCCCGGCCGGGGCGCTGTTTCCTTCTG
CAGTTCCCGTCCCCTGAGTGGGACACCGTCACTCCTGAAGCCAAAAACCTCATCAACCAG
ATGCTGACCATCAACCCTGCCAAGCGCATCACAGCCCATGAGGCCCTGAAGCACCCGTGG
GTCTGCGTGAGTCGCCCTTGGTGCCCATGGTGGGGAGGGGGCTCCTGGTGGAGATGGCCT
CAGACCACTCCCCTGGCAAGGACCCCAAGAGGGTCCTGTTCCTGACATCCAAGAGCTCCC
[T,C]
TGGGTCCCCTGGGTGCTCCTTGTGGCCTCTGGCTTGGGACATACCAGCACGTTTGTGAGG
CCTGGGGCTTGGAAGGCATTAGAGGGTAGAGGTGATCCCTTCCTCCCAACTGCAGTCCTG
TCTGTGAGGGGCAGAGTGGACGAGGCAAGGGAGAGACGAGTCTTGAAGTCCCAGGCGGGT
GGGGACAGACAACCCTTGCCGCAATGGTGGCCGGTGGCTCTTGGCAAGTGGGGACCCCAG
GGTGCCACAAGCCTTGCCACCCTGGCCTCTCCCCTGTGCCTCGGGCTCGGCTGCCATATG (SEQ ID
NO:7)

1785
CTGACCATCAACCCTGCCAAGCGCATCACAGCCCATGAGGCCCTGAAGCACCCGTGGGTC

FIGURE 3K

```
             TGCGTGAGTCGCCCTTGGTGCCCATGGTGGGGAGGGGGCTCCTGGTGGAGATGGCCTCAG
             ACCACTCCCCTGGCAAGGACCCCAAGAGGGTCCTGTTCCTGACATCCAAGAGCTCCCTTG
             GGTCCCCTGGGTGCTCCTTGTGGCCTCTGGCTTGGGACATACCAGCACGTTTGTGAGGCC
             TGGGGCTTGGAAGGCATTAGAGGGTAGAGGTGATCCCTTCCTCCCAACTGCAGTCCTGTC
             [T,A]
             GTGAGGGGCAGAGTGGACGAGGCAAGGGAGAGACGAGTCTTGAAGTCCCAGGCGGGTGGG
             GACAGACAACCCTTGCCGCAATGGTGGCCGGTGGCTCTTGGCAAGTGGGGACCCCAGGGT
             GCCACAAGCCTTGCCACCCTGGCCTCTCCCCTGTGCCTCGGGCTCGGCTGCCATATGACC
             ACCCATTTCCCCACAGCAACGCTCCACGGTAGCATCCATGATGCACAGACAGGAGACTGT
             GGAGTGTCTGAAAAAGTTCAATGCCAGGAGAAAGCTCAAGGTGAGGCCCTGGCCCCTAGT  (SEQ ID
NO:8)

1889      GTGGAGATGGCCTCAGACCACTCCCCTGGCAAGGACCCCAAGAGGGTCCTGTTCCTGACA
             TCCAAGAGCTCCCTTGGGTCCCCTGGGTGCTCCTTGTGGCCTCTGGCTTGGGACATACCA
             GCACGTTTGTGAGGCCTGGGGCTTGGAAGGCATTAGAGGGTAGAGGTGATCCCTTCCTCC
             CAACTGCAGTCCTGTCTGTGAGGGGCAGAGTGGACGAGGCAAGGGAGAGACGAGTCTTGA
             AGTCCCAGGCGGGTGGGGACAGACAACCCTTGCCGCAATGGTGGCCGGTGGCTCTTGGCA
             [A,T]
             GTGGGGACCCCAGGGTGCCACAAGCCTTGCCACCCTGGCCTCTCCCCTGTGCCTCGGGCT
             CGGCTGCCATATGACCACCCATTTCCCCACAGCAACGCTCCACGGTAGCATCCATGATGC
             ACAGACAGGAGACTGTGGAGTGTCTGAAAAAGTTCAATGCCAGGAGAAAGCTCAAGGTGA
             GGCCCTGGCCCCTAGTCCCAGGCACGGCCATGCTTCTCTGTGTCCCTCTGGGCTGGAGCA
             GGGGGGCCTTGGGGGGTCTGGGCAGACCTAGGGGTTACTGCTGCCCCAAGACTGACTGT  (SEQ ID
NO:9)

2416      TCTGGGCTGGAGCAGGGGGGCCTTGGGGGGTCTGGGCAGACCTAGGGGTTACTGCTGCCC
             CCAAGACTGACTGTTAGCAAGTCCCAGACTGGATGCATCAGGTGAACTCAGGCCAGCTTG
             GGAATGAGTCCAGAGGGGCCCTGGGCCAGGTGTGGCTCCTCCTAGTTGTCTGTGCCACCT
             CCTAGCAGCCCTTGGAGGAGCTGTCCTGAAGCGCTCGCTGTGGGCTCCTCACCCGGGCTC
             TGCAGGCAGCACTCACCCTCTGGCAGTCACACTGTTTAGTACAAGCAAGTCCGAAGCTTC
             [C,T]
             GGCTCAGACAGGTTTGGTAAGGAGAGCAGAGCCACACACACTGGTCTTGGGTGGGCTGGG
             GGAGTTCTGGGAGGGAGGTGGGTCCCAGTAGGGTATCCAACCTGCCTGCTTTGGTCAGGG
             CTGGCTCCGGTGACCGCACACTGGCAGTCCCTCTACTTGTGGGTTCCGGGATGGGGACTT
             GTTGCCTGACTGCCCTCTGCTGGTCTCTGAGCAGTTCTCCCCGGAAGCCCCAGGACTGTT
             GCCCTGTCTGAGCCTGTCAGGAAAAGAAGGGGCTGTCAGGGAGCTGGACCCCAGAGGAGC  (SEQ ID
NO:10)

4698      GCTAGGTGGCCCCTGGGCTACACCAAGCCCTTCTGGTCCTGGCCCCCGAGGTCTGGGGGT
             CCGGAGACCCCCATTAAGAATGGCCTGGGCCCCACAGGGAGCCACTGGGCCTGCTGCTGG
             GGGGTCTGAATCCTGAAAGGAGAGCCTTGAGGAGCAGAGCCAGAGAGGCAGAGGCCCTTG
             GGGCAGACACACACCCTGCCCCTCTGGGCCGCATGGAGACGGTGGTCTGTGCTGCTGAG
             TCCTACACATGCATGTCTGCCCTGAGCATCCCCCCAGGACAAGCCGCTCTGGAGTGGGTG
             [A,G]
             GGGTTTTATGCACCCTGAGGAGACTTTCAAGGCTTCCTCTTGGGTTGTTTCTGCAAAGTC
             CTCCTCCCCTGGCCTCAAACCCTGTGAGGGAAAAGGCCGGCACTGGCCACCTGCTCCTCT
             GGGCTGTGCGGGGCCAGAGCCCAGAGGCCCAAGTTGGCTTCTGCCCACCTGCTGGCTTGT
             GACCAT  (SEQ ID NO:11)

5424      CCTCCTCATGACCCACAGGGTGAGCAGCCTGGCCTTCCCAGCCAGAGAACCCTCCTTCTG
             GGGAGGCCCAGGGCGTCCTCGGGGAGGGCAGTCTATTCTCCTCCCATGAGCCCAGTGGAC
             GTGTCTAGCAGGCAGCACCCCGGGAGAGCCCTCCCACGTCTTCTCCATTTGACAGGCCTT
             TCCAGAGCGCAGGCGGGAGGGGGCTGTGATTAGAAAAGAGTGAGGCTAGTGGCTTCTGGG
             GAGGCACTGCTGCCCAGGGGACAGTGCTGAGAGACAGCTGCCTCTACGCTGCCCTGTGCC
             [C,T]
             GGGGCTCCCGCTGCAATGCCCGCCTGTCTGCAAGTGAACGTGGGGCGACGGTGCATGAGG
             CCCTGCATGTGTGGCTCCACCCTGGGCGCCGAGAGCAGCTCTGTCCTGGAGGGTGGTCAG
             TGCATGTGGACAGAGCCCAGCATGGCTGTCCTGGGTGACCAGCTAAGGGGACAAGGCAGA
             GGCAGGGCTGAGAGGACCACCCATCCTGCTAGGTCAGCCCAGCTCAGCCATATCACACGG
             CAGTGAGCATGGAGCTCAGTTCTCTGCCAATGGCAGCTGAGTCTAGTACCATCCAGTCAG  (SEQ ID
NO:12)
```

FIGURE 3L

8722  AAGGCCTGTGCTGGCCCCAGTCAGTGCACAGAAGCGGCCCCAAGGCCAGGGCTGCTGGGC
AGCTCGGAATGAGGGCGAGCAGGGCTGCCCTTGGTGCCTGAGCCAAGGAGCCAATGGGAC
AGACCTCTGAGCCTGGGTGCCAAGTATGAGGTCTGAGACAGGGTGAGCGCCTGGGCTGGG
ACAAGGCCCTCTGAGTGGGCGGCCAGCTGCAGCCCACCCACCCCTACCCCAGGAAGGCAG
GGCCCGGGAGGGCATGACCTCTGGGGTGCTGGCTCAGCTGCCCCCACCCCAACCTGACAC
[C,A]
GCTAGTCCTGAGTTCCCATCAGGGAGGAAGCAGCATCCTGCCTTCCTCTAGGAAGAGCTT
GCATGTGGCCCAGAAGCCAAGGGGGCTCCCCAGCACCCACGGGCATCTCTGGGTCTGGTC
AGAGGAGAAATCTGGATGCTTGCAGGAGCCCCAGGGTCATGGAGGAGGCTGGAGACAGGG
CTGTCCTGGGGTGATGGGATGGCCCCCCCACCTGCTCAGAGCCAGCCTGGGTGCTGGAAC
CACACTTGCCTCAGGACCCTGGGCTTGCTCCTGGGGAAAGAGTGGGGTCAGGCAAAGGGG  (SEQ ID
NO:13)

9982  CCAGGAGTGTTCAGGAAGTCAGTGAGGCAGAAGATACCCTCTCCCCACCAGGACCCCACC
CTCAGCTCCTCCACCATCCTCAACAGGCCGACCCACAGACCACTCCGAAGGTCTGGCTTG
GTGGGGCTGGGCCAGGATCTGCAGGGGGAACAGCCCATAGTGGCACATTCCACGGCCCAT
GGGGAGACGGGGCCACGGTGGTGCAGTAGAGAGGTGTCTAAGCCAGTGGCAGCCAAGGGG
AGGGCTTGCCGTCACCTCTGTGTTCCCTCAGTGCTGCTCTGTGGCTGCCTGAGAGGCAGG
[G,A]
CTTAGGGGCTCCCTGCCGGGGAGGGGAGGGGTCCCCACCATGCTCCGCTCCAACTGCGCC
CCTCAGTGCCCCTTGCCCTGGGGGCTCCTACAGGTGAACCCTATAGCAGTACTCCCAAGG
ATGTAAAGTTGTGGCTGGTGGGTGCCGGCCTTCCTGCTGGGCGCTGTGCTGTGTCCCCT
CAGCTGTCCTAAGAGCTTTGGGGCTTGCTGGCCCGTAGGTCCCCATATTTGCTGGAAGCA
GGCTTGGTGTCCCCTGAGAACCCCAGGCCAGGCTTCGGGAGCCAGCCCCAGACCGCCCAC  (SEQ ID
NO:14)

10951 ACAGCAGCACCTCCGCCAGCCTGGACAGAGCTCCTGTCCATTCCATCCCTGCCGGCTGAC
CCAGGCTCCTCCCCCAGCTGCTCCACGCCGCCTCCATCCCTGTCCCCCACTCTGCTCTGC
ACTTCTTTCTCGCAGGCTCTGGCCACCCACACCTCCTCTGTCTCCCTGTTCCCCTCCTGG
TGGTCTCCGCTTCCTCCTCTTCTCACTTTCCCTCTCTTTCCTTCCTCTGTGTCTTCCTTC
TTCTGTAGGAGCCTCAAACCACCGTCATCCATAACCCAGTGGACGGGATTAAGGTACTGC
[C,T]
CCACTTTCCTCCTCCCGCTTTCCCCAGGCAGGAGGCTCCAGGCCAGGAGAGAGGTCTGGG
GCAGCATTTGTGCCAGAGTGGAGGGCAGATGTCCCATGGCCCTGGCCGCCCCTCCCCGCA
GTACGGTAGGGCCCCAGTCCGTCTTCGTGGGCAACAACAGGACAGACTGGCTCAGGCCCC
AGGCGCGCCCCTGGAGGTGCTTGGCACAGTTGCGCCCGGTCCCCATGTGGCCGACACTCT
CAGACCAGGGCTCTGCGTGTCCCACCTACGGCAGGCAGTAGGGCTTCCTGAGGTCGGAG  (SEQ ID
NO:15)

12603 AGTCTCTCTGCCAGGCTCATCTTGCTGGGAGAAGTGGAGCCCTCATGTGTTGGGGATGCA
GGGTGGCCACAGCACTAGGGTGGCAGGGCCGGCCTCGGACTCCGTGCCAGCCTGTGCTGG
CTGCCGTGAGAATGCACCCTGGTGAGGGGCGCCCTCCCAGGGACCAGCACAGAACTGGGT
GTCTTCTCCGGTCACTGCCGCATGAGGTCCACAGAGCTGGGGCCCTGCAGCCGCCAGAGG
GCATGTCCCCTGAGCCCCTGGCCTTTAAGCCCCGTGGAAGCAGCCGAGGCAGAGATCAGC
[T,C]
TCAGAGCCTGGGCTGGTCCTGACACAGGCCCAGCCCTGTCCACCTGCCCTCAGCCACGTC
CCACCTATCCTTGGCCGCATCCTGACCCGCTGCCTCCCGTGTTTCCTCAGGAGTCTTCTG
ACAGTGCCAATACCACCATAGAGGATGAAGACGCTAAAGGTACCTGCACTTGAGTCCTTG
CCCCCCCAGCGGCCTTGGCATTGCTGGGTTGCTCTTTGAGGTGGGTGGGACTTGGGCAGG
GTCAACTCTCCTGCGACGCCTAGTTTATGCATGTGTTGAGGGGCTCAGGGACCCTGTAGC  (SEQ ID
NO:16)

14583 ACATCCTGAGCTCAGTGAGGAGGGGCTCGGGAGCCCCAGAAGCCGAGGGCCCCTGCCCT
GCCCATCTCCGGCTCCCTTTAGCCCCCTGCCAGCCCCATGTAAGTAGCCTGGGTCCTGCT
GCTGTGGGGGTCATGTTGGAGGGCTGGCAACCCCCTAGAGGGGCCACTCCAGAGCCGAGG
GCAGGCTGAGCGTGGACCCTGGCTCCAGCCTCATCACCCCACAATCCCTCACTGGGGCTT
TCCAGGGTGGCCCCAGCCCATCGAGCCCCACCTCTTTGTGAGGAGGGCCCTGGACCACTT
[C,T]
CCTGCTCAAGGCCACTGGGCAGGATGGGAGGCCCTGGAGGCTCGGGCCTCAATTCCAGTC
TTCAGGGTCGGTGCAGGCCTCACTCCACCTCAGCTTGCGGGCGGGGGGCTCCCTGCTAT
TGAGGCAGGCTCTGATTCAGGGCCTGATCCCAGGGCCCAAGGGGTCTAGAACACGGGACC
CCTCCCACTGGCCTCCTCCGCCTTGCCGCCGCCTCGTGTGTCTGTCTGCCTCATGTTCAC

FIGURE 3M

```
              GTCTCATCTGTTCCACCCCAGCCCCCAGGGATCTCTGACATCCTGAACTCTGTGAGAAGG   (SEQ ID
      NO:17)

17290   CTGTCCCCTTGTGCCCCATCCCCCACATCTGCCTCTGTGCCCCTCAATCTCTGGCTTGGC
              TGTCTGCCCATGGTTTCTCTCCTGCGTGCCCCCGTGCCTGCCTTGTGTTCACGTCTCGT
              CTGTTCCGCCCCAGCCCCCAGGGATCTCTGACATCCTGAACTCTGTGAGGAGGGGCTCAGG
              GACCCCAGAAGCCGAGGGCCCCTCGCCAGTGGGGCCCCCGCCCTGCCCATCTCCGACTAT
              CCCTGGCCCCCTGCCCACCCCATGTAAGTAGCACCTTGAGTGGCCGTGGCAGCGGCTGCC
              [T,C]
              GGAGGGGCTCGGGGCGTGCGAGCCTGGCAGTGGTGCTCTGGGAAGGGCCATTCTTGCGGA
              GGAGGGCGGGGCACAGGATCCCTCTGCTGGGTCCCAGGGAATTGCTTTGAAGCACATGAA
              GGTGCCACTGGGTCTCAGAAAATGGAGGTTATGGTTATGAAGTGTGTATGACATATGTGT
              ATAGGAAGAGCGTCCAAAGAGCAGGTTTGTTGCCGACCCCAGCATTCGCAACCCTGAGG
              TCCACAGCTTTCTCCTGATGGGAGGGGAATGGGTGGCAAAGGGTCTGCGCGTGTGGCAAG   (SEQ ID
      NO:18)

18188   ATCCCAGGGCTGCTGCCACCCCCACCTGTGGGGAGACACCAGACTGGGGGTGGTGTGGAG
              ATACTCTTAGAGAAGAGGCTGCTGGGCCACGGGCTCGGCATGGCAGGGCAGTGGCTAGGT
              AAGTACTTGAGGGACAGGTGGGGTCTGCTTGCCACCGTCCCCTCTGCAGGCTGGGCCTGG
              GGGCTGCTGCAGGCGGCCAGGGCAGAAGGGTGTGGGGAGAGTGAACCCACAGGAGCAGCG
              GCTCGAGGAGGGGGATGCAGGCTGCAGGCTCAAAGGGGCACTGGATCCACCCTGGGTGCC
              [C,T]
              GAGAGAGCAGGGGGCAGCCCCTGGAGGGGTACTCACCCCCAGAGCTTCTGTGGTCGGCTG
              AGGACCCCCAGCAGGGGTTGACTGAGGGGATCAGAGGCAAGCAGCTGAGGGGAGAGGCCA
              GGTTCTTGATGCTGATAGGGTCGGGGTGCCTGGGCGACCAGAACTCAAGGAGGGAGGCAT
              GGGGAGGGGCCGCCGTGCAGCTGGGGTGGGTGCACCGCAGAGCCTCTGGGAGTGGTCAGA
              ACCCCCGACACCTGCCACTTCTACAGCAGCTCATCTGATTTTAAGGGGCTTGCTGCCCTT   (SEQ ID
      NO:19)

19911   AGCACGGTTACCACTCTTGATTGGAACTCTGACCATGCATCTCCTCTTCTGTTTACTTCA
              CGCTTTCTCTTCCCATCAACTCCCATTTTAATTACAATTTGTTTAAAAGCACTGCATATT
              ACTTCATTAAACAGAAGATTAGTTTCACTTACCATTAGTGTAAGGTGACTATAGAACCAA
              AGCAGACTGGAAACCAAATGACATAATGTCATTCTCTTCTCCATTCCAGCTGCCTGCTGC
              TGTGCGCCTGAGAACCCCTGTGGAGTGGGAGGGGCAGCTGTCTCTGTACATTAGAAAGGG
              [A,G]
              GGTTAACTAAGTGACAGGAGGTGTTTGGGACATGTGGACACCAGACTTCTCTCTTGATGC
              AAGGAGGGCAGAGCCAGGCAGCCTAGTGGGGGCTGGCTTGGGGGCTGCTGGAAGGACTGG
              CTACAGGTGGAAGAGAGGTCAGACCTGAAGCTTGGGGCCACCTCCAGGAAAGGACAGGTG
              AAAGTGGAGGCATGAGGCAGGGAGAGGCAGGTGCCAGGCAGAGGGTGGAGAGGAGGCAG
              GAACATAGCAGCTGGGGCGGGGCGGGCCCTCAAGTGTCATATGCTACTTTCCTGGGGCC   (SEQ ID
      NO:20)

21328   GCTGGGCACAGTGGCTCATACCTGTAATCCCAGCACTTTGGGAGGCCGAGGTGGGCAGAT
              CACTTGAGGTTAGGAGTTTGAGACCAGCCTGGCCAATATGGTGAAACCTCATCTCCACTA
              AAAATATACACACACAAAAATTAGCTGGGTGTGGTGGTGTGCACCTGTAGTTCCAGCTAC
              TCGGGAGGCTGAGGCAGGAGAATCGCTTGAACCTGGGAGTCAGAGACTGCAGTGAGCCGA
              GATCATGTCACTGCACTCCAGCCCGGGTGACAGAGTGAGACTCCATCTAAAAAAAAAAAA
              [C,A,G]
              AATTCCCTCCTCTGGGAATTTAGACCACAGACAGGTTGCATGTATGTGGCCGTTGGAGGC
              AGCACTCACAGCAAAGAGTGGAAACGTCACCACAGGGCCTGCCTTCTGGTGAAAATGGTG
              TCCTGCAGGGCGGGCAGCTGTTTGAGGGCAGGTGTCCCAGGTGCGGCCTGCAGCAGCCTG
              AGGGTCACAGAGCGCAGTGCTGGGAGTGCAGAGACTTCCCCCACAGGGAGAGTTCCCAGG
              AACCTGCTTCCGGTGCACTTCTGGGGGTTTGAGTTTTTTCCACGGACGAATTACTTTGAG   (SEQ ID
      NO:21)

21391   TTGAGGTTAGGAGTTTGAGACCAGCCTGGCCAATATGGTGAAACCTCATCTCCACTAAAA
              ATATACACACACAAAAATTAGCTGGGTGTGGTGGTGTGCACCTGTAGTTCCAGCTACTCG
              GGAGGCTGAGGCAGGAGAATCGCTTGAACCTGGGAGTCAGAGACTGCAGTGAGCCGAGAT
              CATGTCACTGCACTCCAGCCCGGGTGACAGAGTGAGACTCCATCTAAAAAAAAAAAAGAA
              TTCCCTCCTCTGGGAATTTAGACCACAGACAGGTTGCATGTATGTGGCCGTTGGAGGCAG
              [T,C]
              ACTCACAGCAAAGAGTGGAAACGTCACCACAGGGCCTGCCTTCTGGTGAAAATGGTGTCC
```

FIGURE 3N

```
              TGCAGGGCGGGCAGCTGTTTGAGGGCAGGTGTCCCAGGTGCGGCCTGCAGCAGCCTGAGG
              GTCACAGAGCGCAGTGCTGGGAGTGCAGAGACTTCCCCCACAGGGAGAGTTCCCAGGAAC
              CTGCTTCCGGTGCACTTCTGGGGGTTTGAGTTTTTTCCACGGACGAATTACTTTGAGAAA
              CCACTGTTACTCGTGTGTATAGGTGAGCGTGCGTGTGCATGTGTGTTCTGTGTGTGAGTG    (SEQ ID
       NO:22)

22588  GCTGCTTCCTCCTCCCCGGCCTCCGGGTGGCCTTGCTGACGGCTCCTTCTCTGAGGCAGG
              TCTCTGCCTTCTCGCCTGGTGCCTGCACTCAGTAGCCCCCTCACCAGAGCTGCTGGGTGA
              AGGAAGCACTAAGAACCCAAGGCTCGGGAGGAGAGTGGGGCCGGGAAGCTGCAGGGAAGC
              GCAGGGCCAGGCCTGGTGGGCCCAGGGGCTGGCTCACGGGAGGGCAGGAGGGAGACTGTG
              GCGGACAGCACGTGGGGCCAGGAGGTGACCTCCAAGTGGATTGTGGGTGGGTTTTTTGTC
              [C,T]
              TCTTTCTGCATTTTCCAGGCATTTTGTAATGTGGATAGAATATTTCTGTTCTTCAAAAAT
              ACTTTAGTTAAGAAAAAATAAGATGGAAGCTGTTGCACTTGAAAATGAGGAAGCCACTGGT
              GATGCAGGGGGGCGGCGGAGAGGACCTCTTCTGCAAATAGCGGCAGGAACACGGCATGG
              ATGCAGCTCGCGCTCCCCAGGCCCTCCCCTGGGCTGTGTGGAGGGGTCCGGGGGGAATG
              GGCCAGCGCCCAGTGGTCACCTGGCCATGTCTCCCCACAGCCCGGAAGCAGGAGATCATT    (SEQ ID
       NO:23)

22965  ATAAGATGGAAGCTGTTGCACTTGAAAATGAGGAAGCCACTGGTGATGCAGGGGGGCGG
              CGGAGAGGACCTCTTCTGCAAATAGCGGCAGGAACACGGCATGGATGCAGCTCGCGCTCC
              CCCAGGCCCTCCCCTGGGCTGTGTGGAGGGGTCCGGGGGGAATGGGCCAGCGCCCAGTGG
              TCACCTGGCCATGTCTCCCCACAGCCCGGAAGCAGGAGATCATTAAGACCACGGAGCAGC
              TCATCGAGGCCGTCAACAACGGTGACTTTGAGGCCTACGCGTGAGTCCCTGGGGCTGGGG
              [-,G]
              GGGGCTGTGCAGGACAAGGATGTGGGACCCTTGGGGGGGCCTGCTCAGAGTCAGGGGTCC
              ACGGGGCCCCTCCTCACTTGGATTTGGCCCCCAGGAAAATCTGTGACCCAGGGCTGACCT
              CGTTTGAGCCTGAAGCACTGGGCAACCTGGTTGAAGGGATGGACTTCCACAGATTCTACT
              TCGAGAACCGTGAGTGAGGAAGCCCGGGTGGGCATGAGGGGCGGTGCCCCAGGAGAGC
              CTCTCGGCCCCTCCCAGGGACAGCATGGTGGCTGCCTATGGAAGCCCTGTCCCCTCTGTG    (SEQ ID
       NO:24)

23498  CCCGCCAGAGGCCATACCCAGCCCCCAGAATCCCACTCTTGGAGGGGCCCATGCTGCTCC
              CAGGAGAGCCGAGCCTCCCCAATAAGGGGAGTTGAGAGAGGGAAAGGATTAGGCTGGTGG
              GGTGGAAGACGGGCACCAGGGCAGTCATGGTAACCCGAGACCCCCGCCCCGCCTGCTGTC
              CACAGTGCTGGCCAAGAACAGCAAGCC
              [G,A]
              ATCCACACGACCATCCTGAACCCACACGTGCACGTCATTGGAGAGGATGCCGCCTGCATC
              GCTTACATCCGGCTCACGCAGTACATTGACGGGCAGGGCCGGCCCCGCACCAGCCAGTCT
              GAGGAGACCCGCGTGTGGCACCGCCGCGACGGCAAGTGGCAGAACGTGCACTTCCACTGC
              TCGGGCGCGCCTGTGGCCCCGCTGCAG  (SEQ ID NO:25)

23663  GCCTCCCCAATAAGGGGAGTTGAGAGAGGGAAAGGATTAGGCTGGTGGGTGGAAGACGG
              GCACCAGGGCAGTCATGGTAACCCGAGACCCCCGCCCCGCCTGCTGTCCACAGTGCTGGC
              CAAGAACAGCAAGCCGATCCACACGACCATCCTGAACCCACACGTGCACGTCATTGGAGA
              GGATGCCGCCTGCATCGCTTACATCCGGCTCACGCAGTACATTGACGGGCAGGGCCGGCC
              CCGCACCAGCCAGTCTGAGGAGACCCGCGTGTGGCACCGCCGCGACGGCAAGTGGCAGAA
              [T,C]
              GTGCACTTCCACTGCTCGGGCGCGCCTGTGGCCCCGCTGCAGTGAAGGTGAGTGTTCTGT
              GCTAAGTGACAGCTGGGGCAGAGGGGTGGCGGTGGTGTGAGTGGCTGCAGCCTGGGGAGG
              CGATGGGGAGCGGTGGGGCCTGTGCAGAGCCCATGCCTGGGAAGTCCCTGAGCTTTCCT
              GGTGAGGCCACAGGAATGATGTCAAATTAGGGACCACGGCAGGCTGGGTGTGGCAGGCCT
              CCCCAGAGGACTGGGGAGCTGGTGAGGGCCTGAGCAGTCCACACTGGCCAGAGCTGGGTG   (SEQ ID
       NO:26)

25427  TGTGGCAAGAGGACTCTGCCTGGGCTGGCCCCCCTCCTGTGTGAGGTGTCTGTCCCTTCT
              CTGCTGGCCAGCAGCAGATGCACTGGCAGCTCCCAACCCTGTTTCCGCCCCTCGGCCCTC
              CCCCAGCCTGTTCGGCTTCTCTGCAGCCCGCAAGGGGAGCAGACTTTTGACAAAGGACT
              GCGGGCCTCGCTCAAGTCCCTGAGCCCCAGCTGAAGCTGGGAGGGGAGGCCAGGCTTTG
              TGTCTGGGCATATTCGTCTGCTGATGGGGTTTGGGGAAGCCTGGGGCTTGGGGTTTGGTC
              [A,G]
              GGTGGTGCAGCTAGTGGCAGAGCGGGATCAGAGGTGGTGGCTGCCCAGCTTCTGGGCTGA
```

FIGURE 3O

```
              GACAAGGGTCTGTGCAGGGGTTTACTGAAGTGGGAGTGCCTTTGGAATCTGGGCCGGGAG
              CAGAAGGGAGCAAAAGCTACAGTGGGAGCCAGCCTAGGGCACATGGGAGGCGTGAGGGCA
              GTGCTGCCCGTGCAGTGTCAGGTGTGCCAGTGCCTTGGCGGGCTGCAGTGCGTGTGAGGG
              CACCTTCTAGGTGGGCCAGGGATGCAGCTATGGAGATAAGGCGGGCTGGGGACAGAAACA     (SEQ ID
NO:27)

27727         GCAAACTCTTAGGTTGGAGTAAGGAGTAACCCCCTGCCAAGTTTCTCCTGTCCTCAGGCT
              CCACCCACCACCTATGCTGCCTGGCCCCATGGGGCACACGCTCAGGCCCAGCCTGGGAAA
              GCAACTGCACCTGCCTGTGCTATGCTGGCCCTTCTCAGCCTCAATGCCCTCCTCCCTCCC
              CGACGCACCCTCGTGGCCCCCGCTGGGCCCCTGATGCACCCTCATGTCTCCATGGCAAC
              CTGCTCAGAGTGTGGCCCTGCCCTTGGCTCCCCTCCACACCTGTGTCCCAGGCAGTGCCA
              [C,T]
              GGCACTTTCCTAAACAGAAGGATGGGCTTCAAAACAGTCCCAGACACTAAACACACCTGC
              ATTTTGGGTCCAAGTAACTTCTGACAAGACGAGTGCCCCTACACACCCTCAGTCCTATCC
              ACTATGGGCAAGGAGCCTGAAGGATCCCCCAGAACTGGCTAAAGCCCTCAGTCTCCTCCT
              CCACCCTGAGCACCTTCACGCGGCAGAGTGGCCCTGGATGTCAGCTTCTTGCTCCCCATG
              GTCTGCACCTGGACAGGTGCTCTCAGGTGTGTGGGTGGGCAGGTGGCAGGTCCCAAGAGC     (SEQ ID
NO:28)

27834         CCAGCCTGGGAAAGCAACTGCACCTGCCTGTGCTATGCTGGCCCTTCTCAGCCTCAATGC
              CCTCCTCCCTCCCCGACGCACCCTCGTGGCCCCCGCTGGGCCCCCTGATGCACCCTCATG
              TCTCCATGGCAACCTGCTCAGAGTGTGGCCCTGCCCTTGGCTCCCCTCCACACCTGTGTC
              CCAGGCAGTGCCACGGCACTTTCCTAAACAGAAGGATGGGCTTCAAAACAGTCCCAGACA
              CTAAACACACCTGCATTTTGGGTCCAAGTAACTTCTGACAAGACGAGTGCCCCTACACAC
              [T,C]
              CTCAGTCCTATCCACTATGGGCAAGGAGCCTGAAGGATCCCCCAGAACTGGCTAAAGCCC
              TCAGTCTCCTCCTCCACCCTGAGCACCTTCACGCGGCAGAGTGGCCCTGGATGTCAGCTT
              CTTGCTCCCCATGGTCTGCACCTGGACAGGTGCTCTCAGGTGTGTGGGTGGGCAGGTGGC
              AGGTCCCAAGAGCCAGGTGCAAAGAATCTAGGCCAGTGCCCACGAGTGCTGCAGTGTCTG
              TCCCCAGCATGGTATCTAGGGCTCCACTTGCCTATCAGCTGTAATCGGAGGAGGCTTTCC     (SEQ ID
NO:29)
```

FIGURE 3P

28336  AAGAATCTAGGCCAGTGCCCACGAGTGCTGCAGTGTCTGTCCCCAGCATGGTATCTAGGG
CTCCACTTGCCTATCAGCTGTAATCGGAGGAGGCTTTCCAGGCCAGGCCTCCCCCAGGAA
GGCTGCAGGCACTGCGGATCGTGCGCCCTCACATGCATTATTCCTGAGGCCCTTCTGCAG
ATGCCATCAGGGCAGCAACTCTGATGAGGTATTAGGGCACAGCACACAGGGCTAAGCCAC
CCTGTACTGGGCCAAGCGCTACAGGCAAAAAGGACACCACCGACGGGCATTTCATTCATC
{G,A}
CTTTTATTTTTATATATTTTTGAGAGGGAGCCTCACTCTGTCGCCCAGGCTGGAGTGCAG
TGGCGCGATCTTGGCTCACTGCAACTTCTCCCTCCTGGGTTC  (SEQ ID NO:30)

FIGURE 3Q

NUCLEIC ACID MOLECULES ENCODING A SUBUNIT OF A HUMAN CALCIUM/CALMODULIN-DEPENDENT PROTEIN KINASE

FIELD OF THE INVENTION

The present invention is in the field of kinase proteins that are related to the calcium/calmodulin-dependent protein kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Calcium/Calmodulin-Dependent Protein Kinases

The novel human protein, and encoding gene, provided by the present invention is related to the family of calcium/calmodulin-dependent protein kinases, which are serine/threonine kinases. The protein of the present invention shows a high degree of similarity to calcium/calmodulin-dependent protein kinase II (CaM II), and the CaM II beta subunit in particular. Furthermore, the protein/cDNA of the present invention may be an alternative splice form of a protein provided in Genbank gi5326757 (see the amino acid sequence alignment in FIG. 2).

CaM II is comprised of alpha, beta, gamma, and delta subunits. Each subunit is encoded by a separate gene and alternatively splice forms of each subunit have been found (Breen et al., *Biochem. Biophys. Res. Commun.* 236 (2), 473–478 (1997)). CaM II exerts important effects on hormones and neurotransmitters that utilize calcium as a second messenger and has been implicated in a wide variety of neuronal and non-neuronal functions, including cell growth control (Tombes et al., *Biochim Biophys Acta* Mar. 1, 1997;1355(3):281–92). It has been found that certain CaM II isozymes are preferentially expressed in tumor cells and thus certain tumor cells express a completely different spectrum of CaM II isozymes compared with normal cells/tissues (Tombes et al., *Biochim Biophys Acta* Mar. 1, 1997;1355(3):281–92). Therefore, CaM II plays a key role in cell growth control and tumor proliferation and, importantly, novel human CaM II variants are valuable as potential diagnostic markers and therapeutic targets for cancer.

Expression of CaM II beta mRNA is elevated in the frontal cortex in schizophrenia and CaM II is known to play a key role in the amplified action of amphetamine induced-dopamine release, which is observed in schizophrenics (Novak et al., *Brain Res. Mol. Brain Res.* 82 (1–2), 95–100 (2000)). Thus, CaM II, and CaM II beta in particular, may play important roles in schizophrenia.

Beta-cell CaM II activity is associated with insulin secretion, and multiple isoforms of CaM II are expressed in human islets of Langerhans (Breen et al., *Biochem. Biophys. Res. Commun.* 236 (2), 473–478 (1997)). It has been suggested that CaM II controls activation-induced cellular differentiation, and is important for imparting antigen-dependent memory to T cells (Bui et al., *Cell* 100: 457–467, 2000). For a further review of CaM II and CaM II beta, see Wang et al., *FEBS Lett.* 475 (2), 107–110 (2000) and Li et al., *Cytogenet. Cell Genet.* 66: 113–116, 1994.

Calmodulin is a major Ca(2+)-binding protein in the brain, where it modulates numerous Ca(2+)-dependent enzymes and cellular functions. Ca2+/calmodulin-dependent protein kinase II (CaMKII) is particularly important in the brain and is involved in a variety of neuronal functions (Sola et al., *Prog Neurobiol* 1999 Jun;58(3):207–32), such as postsynaptic responses (such as long-term potentiation), neurotransmitter synthesis and exocytosis, cytoskeletal interactions and gene transcription (Colbran, *Neurochem Int* December 1992;21(4):469–97). Ca2+ and calmodulin antagonists inhibit seizures induced by convulsant agents, indicating that the Ca2+/calmodulin signaling system plays an important role in the onset of seizures. Changes in CaMKII expression has been observed following seizures and, furthermore, expression of calmodulin and CaMKII in microglial cells in the brain increases following seizures (Sola et al., *Prog Neurobiol* June 1999;58(3):207–32). CaMKII levels are also altered in pathological states such as Alzheimer's disease and ischemia (Colbran, *Neurochem Int* December 1992;21(4):469–97), suggesting a role of CaMKII in these disorders.

Calmodulin is also important for regulating the plasma membrane calcium pump, which transports Ca2+ out of cells. The pump is inactive in the absence of calmodulin, but is activated by calmodulin binding (Penniston et al., *J Membr Biol* Sep. 15, 1998;165(2):101–9).

Due to their importance in cell growth control, novel human CaM II proteins/genes, such as provided by the present invention, are valuable as potential targets for the development of therapeutics to treat cancer and other disorders. Furthermore, SNPs in CaM II genes, such as provided by the present invention, may serve as valuable markers for the diagnosis, prognosis, prevention, and/or treatment of cancer and other disorders.

Using the information provided by the present invention, reagents such as probes/primers for detecting the SNPs or the expression of the protein/gene provided herein may be readily developed and, if desired, incorporated into kit formats such as nucleic acid arrays, primer extension reactions coupled with mass spec detection (for SNP detection), or TaqMan PCR assays (Applied Biosystems, Foster City, Calif.).

Kinase proteins, particularly members of the calcium/calmodulin-dependent protein kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the calcium/calmodulin-dependent protein kinase subfamily.

SUMMARY OF THE INVENTION

The present invention is based in part on the identification of amino acid sequences of human kinase peptides and proteins that are related to the calcium/calmodulin-dependent protein kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in fetal brain, testis, lung small cell carcinoma, and uterus endometrium adenocarcinoma.

DESCRIPTION OF THE FIGURE SHEETS

FIG. 1 provides the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in fetal brain, testis, lung small cell carcinoma, and uterus endometrium adenocarcinoma.

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 26 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the calcium/calmodulin-dependent protein kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the calcium/calmodulin-dependent protein kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the calcium/calmodulin-dependent protein kinase subfamily and the expression pattern observed. Experimental data as provided in FIG. 1 indicates expression in fetal brain, testis, lung small cell carcinoma, and uterus endometrium adenocarcinoma. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known calcium/calmodulin-dependent protein kinase family or subfamily of kinase proteins.

Specific Embodiments

Peptide Molecules

The present invention provides nucleic acid sequences that encode protein molecules that have been identified as being members of the kinase family of proteins and are related to the calcium/calmodulin-dependent protein kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors, or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in fetal brain, testis, lung small cell carcinoma, and uterus endometrium adenocarcinoma. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press., New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 7 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 7 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 26 different nucleotide positions. Some of these SNPs that are located outside the ORF and in introns may affect gene transcription.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in fetal brain, testis, lung small cell carcinoma, and uterus endometrium adenocarcinoma, as indicated by virtual northern blot analysis. A large percentage of pharmaceutical agents are being developed that modulate the activity of kinase proteins, particularly members of the calcium/calmodulin-dependent protein kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in fetal brain, testis, lung small cell carcinoma, and uterus endometrium adenocarcinoma. Such uses can readily be determined using the information provided herein, that which is known in the art, and routine experimentation.

The proteins of the present invention (including variants and fragments that may have been disclosed prior to the present invention) are useful for biological assays related to kinases that are related to members of the calcium/calmodulin-dependent protein kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in fetal brain, testis, lung small cell carcinoma, and uterus endometrium adenocarcinoma, as indicated by virtual northern blot analysis.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in fetal brain, testis, lung small cell carcinoma, and uterus endometrium adenocarcinoma. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data, as provided in FIG. 1 indicates that kinase proteins of the present invention are expressed in fetal brain, testis, lung small cell carcinoma, and uterus endometrium adenocarcinoma, as indicated by virtual northern blot analysis.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in fetal brain, testis, lung small cell carcinoma, and uterus endometrium adenocarcinoma. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods, for detecting the presence, or levels of, the protein (or encoding mRNA) in a cell, tissue, or organism. Experimental data as provided in FIG. 1 indicates expression in fetal brain, testis, lung small cell carcinoma, and uterus endometrium adenocarcinoma. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in fetal brain, testis, lung small cell carcinoma, and uterus endometrium adenocarcinoma. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in fetal brain, testis, lung small cell carcinoma, and uterus endometrium adenocarcinoma, as indicated by virtual northern blot analysis. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in fetal brain, testis, lung small cell carcinoma, and uterus endometrium adenocarcinoma. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in fetal brain, testis, lung small cell carcinoma, and uterus endometrium adenocarcinoma. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in fetal brain, testis, lung small cell carcinoma, and uterus endometrium adenocarcinoma. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 7 (as indicated in FIG. 3), which is supported by multiple lines of evidence, such as STS and BAC map data.

FIG. 3 provides information on SNPs that have been found in the gene encoding the kinase protein of the present invention. SNPs were identified at 26 different nucleotide positions. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2× SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 26 different nucleotide positions.

The probe can correspond to any sequence along the entire length of the nucleic acid molecules provided in the Figures. Accordingly, it could be derived from 5' noncoding regions, the coding region and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 7 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in fetal brain, testis, lung small cell carcinoma, and uterus endometrium adenocarcinoma, as indicated by virtual northern blot analysis. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in fetal brain, testis, lung small cell carcinoma, and uterus endometrium adenocarcinoma, as indicated by virtual northern blot analysis.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in fetal brain, testis, lung small cell carcinoma, and uterus endometrium adenocarcinoma. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in fetal brain, testis, lung small cell carcinoma, and uterus endometrium adenocarcinoma, as indicated by virtual northern blot analysis. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in fetal brain, testis, lung small cell carcinoma, and uterus endometrium adenocarcinoma.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 26 different nucleotide positions. Some of these SNPs that are located outside the ORF and in introns may affect gene transcription. The gene encoding the novel kinase protein of the present invention is located on a genome component that has been mapped to human chromosome 7 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification a product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes it specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al, *PNAS* 85:4397 (1988); Saleeba et al, *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 26 different nucleotide positions. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in fetal brain, testis, lung small cell carcinoma, and uterus endometrium adenocarcinoma, as indicated by virtual northern blot analysis. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 26 different nucleotide positions. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors, contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., Gene 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion E. coli expression vectors include pTrc (Amann et al., Gene 69:301–315 (1988)) and pET 11d (Studier et al., Gene Expression Technology: Methods in Enzymology 185:60–89 (1990)).

Recombinant protein expression can be maximized in host bacteria by providing a genetic background wherein the host cell has an impaired capacity to proteolytically cleave the recombinant protein. (Gottesman, S., Gene Expression Technology: Methods in Enzymology 185, Academic Press, San Diego, Calif. (1990) 119–128). Alternatively, the sequence of the nucleic acid molecule of interest can be altered to provide preferential codon usage for a specific host cell, for example E. coli. (Wada et al., Nucleic Acids Res. 20:2111–2118 (1992)).

The nucleic acid molecules can also be expressed by expression vectors that are operative in yeast. Examples of vectors for expression in yeast e.g., S. cerevisiae include pYepSec1 (Baldari, et al., EMBO J. 6:229–234 (1987)), pMFa (Kurjan et al., Cell 30:933–943(1982)), pJRY88 (Schultz et al., Gene 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell Biol. 3:2156–2165 (1983)) and the pVL series (Lucklow et al., Virology 170:31–39 (1989)).

In certain embodiments of the invention, the nucleic acid molecules described herein are expressed in mammalian cells using mammalian expression vectors. Examples of mammalian expression vectors include pCDM8 (Seed, B. Nature 329:840(1987)) and pMT2PC (Kaufman et al., EMBO J. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of nucleotide sequence selected from the group consisting of:

(a) a nucleotide sequence that encodes a polypeptide having an amino acid sequence comprising [not shown in] SEQ ID NO: 2;

(b) a nucleotide sequence consisting of SEQ ID NO:1;

(c) a nucleotide sequence consisting of SEQ ID NO:3; and (d) a nucleotide sequence that is completely complementary to the nucleotide sequence of (a), (b) or (c).

2. A vector comprising the nucleic acid molecule of claim 1.

3. A isolated host cell containing the vector of claim 2.

4. A process for producing a polypeptide comprising culturing the host cell of claim 3 under conditions sufficient for the production of said polypeptide, and recovering said polypeptide.

5. An isolated polynucleotide, wherein the nucleotide sequence of said polynucleotide consists SEQ ID NO:1 or the complement thereof.

6. An isolated polynucleotide having a nucleotide sequence comprising SEQ ID NO:1 or the complement thereof.

7. An isolated polynucleotide, wherein the nucleotide sequence of said polynucleotide consists of SEQ ID NO:3 or the complement thereof.

8. The vector of claim 2, wherein said vector is selected from the group consisting of a plasmid, a virus, and a bacteriophage.

9. The vector of claim 2, wherein said isolated nucleic acid molecule is inserted into said vector in proper orientation and correct reading frame such that a polypeptide comprising SEQ ID NO:2 is expressed by a cell transformed with said vector.

10. The vector of claim 9, wherein said isolated nucleic acid molecule is operatively linked to a promoter sequence.

11. An isolated nucleic acid molecule comprising a nucleotide sequence selected from the group consisting of:

(a) transcript or cDNA sequence that encodes a polypeptide having an amino acid sequence comprising SEQ ID NO:2;

(b) SEQ ID NO:1;

(c) nucleotides 262-1809 of SEQ ID NO:1; AND (d) a nucleotide sequence that is completely complementary to the nucleotide sequence of (a), (b), or (c).

12. A vector comprising the nucleic acid molecule of claim 11.

13. An isolated host cell containing the vector of claim 12.

14. A process for producing a polypeptide comprising culturing the host cell of claim 13 under conditions sufficient for the production of said polypeptide, and recovering said polypeptide.

15. The vector of claim 12, wherein said vector is selected for the group consisting of a plasmid, a virus, and a bacteriophage.

16. The vector of claim 12, wherein said isolated nucleic acid molecule is inserted into said vector in proper orientation and correct reading frame such that a polypeptide comprising SEQ ID NO:2 is expressed by a cell transformed with said vector.

17. The vector of claim 16, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 2218
<212> TYPE: DNA
<213> ORGANISM: Human

<400> SEQUENCE: 1

| | | | | | | |
|---|---|---|---|---|---|---|
| cgggcgcggc | ggcggcggcg | gtgacagcgg | cgcccgcgcc | tcccgcgcg | taggtgtgcg | 60 |
| gcgcgctcct | ggcgaggacg | gagcgagcag | atctcgcgtg | cgctcgccgc | ccggcgcagc | 120 |
| ccagcccggc | ccccgcctgg | cgccgcgagc | cgaggtgtct | cccgcgcccg | cgcccgtgtc | 180 |
| gccgccgtgc | ccgcgagcgg | gagccggagt | cgccgccgcc | cgagcgcagc | cgagcgcacg | 240 |
| ccgagcccgt | ccgccgccgc | catggccacc | acggtgacct | gcacccgctt | caccgacgag | 300 |
| taccagctct | acgaggatat | tggcaagggg | gctttctctg | tggtccgacg | ctgtgtcaag | 360 |
| ctctgcaccg | gccatgagta | tgcagccaag | atcatcaaca | ccaagaagct | gtcagccaga | 420 |
| gatcaccaga | agctggagag | agaggctcgg | atctgccgcc | ttctgaagca | ttccaacatc | 480 |
| gtgcgtctcc | acgacagcat | ctccgaggag | ggcttccact | acctggtctt | cgatctggtc | 540 |
| actggtgggg | agctctttga | agacattgtg | gcgagagagt | actacagcga | ggctgatgcc | 600 |
| agtcactgta | tccagcagat | cctggaggcc | gttctccatt | gtcaccaaat | ggggtcgtc | 660 |
| cacagagacc | tcaagccgga | gaacctgctt | ctggccagca | agtgcaaagg | ggctgcagtg | 720 |
| aagctggcag | acttcggcct | agctatcgag | gtgcaggggg | accagcaggc | atggtttggt | 780 |
| ttcgctggca | caccaggcta | cctgtcccct | gaggtccttc | gcaaagaggc | gtatggcaag | 840 |
| cctgtggaca | tctgggcatg | tgggtgatc | ctgtacatcc | tgctcgtggg | ctacccaccc | 900 |
| ttctgggacg | aggaccagca | caagctgtac | cagcagatca | aggctggtgc | ctatgacttc | 960 |
| ccgtcccctg | agtgggacac | cgtcactcct | gaagccaaaa | acctcatcaa | ccagatgctg | 1020 |
| accatcaacc | ctgccaagcg | catcacagcc | catgaggccc | tgaagcaccc | gtgggtctgc | 1080 |
| caacgctcca | cggtagcatc | catgatgcac | agacaggaga | ctgtggagtg | tctgaaaaag | 1140 |
| ttcaatgcca | ggagaaagct | caaggagcc | atcctcacca | ccatgctggc | cacacggaat | 1200 |
| ttctcagtgg | gcagacagac | caccgctccg | gccacaatgt | ccaccgcggc | ctccggcacc | 1260 |
| accatggggc | tggtggaaca | agccaagagt | ttactcaaca | agaaagcaga | tggagtcaag | 1320 |
| ccccagacga | atagcaccaa | aaacagtgca | gccgccacca | gccccaaagg | gacgcttcct | 1380 |
| cctgccgccc | tggagcctca | aaccaccgtc | atccataacc | cagtgacgg | gattaaggag | 1440 |
| tcttctgaca | gtgccaatac | caccatagag | gatgaagacg | ctaaagcccg | gaagcaggag | 1500 |
| atcattaaga | ccacggagca | gctcatcgag | gccgtcaaca | acggtgactt | tgaggcctac | 1560 |
| gcattctact | tcgagaacct | gctggccaag | aacagcaagc | cgatccacac | gaccatcctg | 1620 |
| aacccacacg | tgcacgtcat | tggagaggat | gccgcctgca | tcgcttacat | ccggctcacg | 1680 |
| cagtacattg | acggcagggg | ccggccccgc | accagccagt | ctgaggagac | ccgcgtgtgg | 1740 |
| caccgccgcg | acggcaagtg | gcagaacgtg | cacttccact | gctcgggcgc | gcctgtggcc | 1800 |
| ccgctgcagt | gaagccaagg | gaggggcaca | gaatgggaa | caggacacag | gatcctaaac | 1860 |
| tccaagggga | ctgtccaccg | atgaacactc | agagtggaca | ccatcttccg | tccacgctgt | 1920 |
| gcccaggaca | gctgtcccca | tccatgaaca | cagggtaaac | atctgccggg | ctccgccacca | 1980 |
| gtggctccct | gggccatggg | acagcggcag | ggctcaccac | ggacagcacg | tggcccagca | 2040 |

```
gccggccacc ctggcgtcct ggggcctcct ccctcctct ccctctcacc ttgtcacctc   2100
cacggagctg cctgtctggg ataatttggg gatttttttt tctgggggat aattcttttg   2160 catgaccct aaagagcaag ccacaccggt ctgctagcta ggtgtccgcg gtgtggtg     2218
```

<210> SEQ ID NO 2
<211> LENGTH: 516
<212> TYPE: PRT
<213> ORGANISM: Human

<400> SEQUENCE: 2

```
Met Ala Thr Thr Val Thr Cys Thr Arg Phe Thr Asp Glu Tyr Gln Leu
 1               5                  10                  15

Tyr Glu Asp Ile Gly Lys Gly Ala Phe Ser Val Val Arg Arg Cys Val
            20                  25                  30

Lys Leu Cys Thr Gly His Glu Tyr Ala Ala Lys Ile Ile Asn Thr Lys
        35                  40                  45

Lys Leu Ser Ala Arg Asp His Gln Lys Leu Glu Arg Glu Ala Arg Ile
    50                  55                  60

Cys Arg Leu Leu Lys His Ser Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
            100                 105                 110

Ala Ser His Cys Ile Gln Gln Ile Leu Glu Ala Val Leu His Cys His
        115                 120                 125

Gln Met Gly Val Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Glu Ala Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala His Glu Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Lys Lys Phe Asn Ala Arg Arg Lys Leu Lys Gly Ala Ile
    290                 295                 300

Leu Thr Thr Met Leu Ala Thr Arg Asn Phe Ser Val Gly Arg Gln Thr
305                 310                 315                 320

Thr Ala Pro Ala Thr Met Ser Thr Ala Ala Ser Gly Thr Thr Met Gly
                325                 330                 335

Leu Val Glu Gln Ala Lys Ser Leu Leu Asn Lys Lys Ala Asp Gly Val
```

-continued

```
              340             345              350
Lys Pro Gln Thr Asn Ser Thr Lys Asn Ser Ala Ala Ala Thr Ser Pro
        355             360             365
Lys Gly Thr Leu Pro Pro Ala Ala Leu Glu Pro Gln Thr Thr Val Ile
    370             375             380
His Asn Pro Val Asp Gly Ile Lys Glu Ser Ser Asp Ser Ala Asn Thr
385             390             395             400
Thr Ile Glu Asp Glu Asp Ala Lys Ala Arg Lys Gln Glu Ile Ile Lys
        405             410             415
Thr Thr Glu Gln Leu Ile Glu Ala Val Asn Asn Gly Asp Phe Glu Ala
        420             425             430
Tyr Ala Phe Tyr Phe Glu Asn Leu Leu Ala Lys Asn Ser Lys Pro Ile
        435             440             445
His Thr Thr Ile Leu Asn Pro His Val His Val Ile Gly Glu Asp Ala
        450             455             460
Ala Cys Ile Ala Tyr Ile Arg Leu Thr Gln Tyr Ile Asp Gly Gln Gly
465             470             475             480
Arg Pro Arg Thr Ser Gln Ser Glu Glu Thr Arg Val Trp His Arg Arg
            485             490             495
Asp Gly Lys Trp Gln Asn Val His Phe His Cys Ser Gly Ala Pro Val
            500             505             510
Ala Pro Leu Gln
        515
```

<210> SEQ ID NO 3
<211> LENGTH: 28438
<212> TYPE: DNA
<213> ORGANISM: Human

<400> SEQUENCE: 3

| | | | | | |
|---|---|---|---|---|---|
| gagctgctgt | gtctctgtcc | ccaggggcag | aggggctgtg | gggttgcagg | ctcagcgtct | 60 |
| gggactctgg | ggtgaaggct | cagccatgcc | ctgcagacac | catggggcag | ggctcagacc | 120 |
| tgtgcacctg | tctcttgcaa | accactgttt | tctctgtttt | gtaaccccccc | acccaacccc | 180 |
| acataacacc | tctgggttta | acaacatgc | acccttgtgc | cggtcacctc | cctgcagccg | 240 |
| gagaacctgc | ttctggccag | caagtgcaaa | ggggctgcag | tgaagctggc | agacttcggc | 300 |
| ctagctatcg | aggtgcaggg | ggaccagcag | gcatggtttg | gtgagtgcca | ggggcagggt | 360 |
| gtgttggctg | gcagttggca | gggcaggagg | tgatgctgac | agcccccttgt | ggcctcttcc | 420 |
| cctctctcta | ggtttcgctg | gcacaccagg | ctacctgtcc | cctgaggtcc | ttcgcaaaga | 480 |
| ggcgtatggc | aagcctgtgg | acatctgggc | atgtggtgag | gcctggcctg | agttggtgcg | 540 |
| ggcagggcc | tcgggtgttt | caggacttcc | cacctacatc | ctggagtgtg | cagtggccag | 600 |
| cacgtcttgc | tctcatctgg | gtttatctgt | gtcagacctg | cccttgagct | gcctggcag | 660 |
| ggtctgccc | acacagccaa | gagccccctt | ccacccaga | ttagaattgc | tcacatgaac | 720 |
| ctggcgcacc | ccagtgctcg | cctgcgctca | gcagaggtct | ggtccagaag | tgtggtgggt | 780 |
| ggatgggagt | ggagaagaga | ggtcaggggc | tgttgggcca | tgggcagggc | acctccttg | 840 |
| ggtagggtc | tcctcccaca | gaggtgggga | gcagcagagg | ggcttgacat | caccctcatc | 900 |
| cctgtgatag | tgtgggtgtg | gggcagaggt | caggggccg | gctgtgccct | tctaccccag | 960 |
| tgtctgctgc | acaggtgggg | gcaaaggaat | gctgaggacc | ccaatgccct | ccagggcca | 1020 |
| caggagctag | gcagtgaggg | tgcagggcat | gggcttcatg | gacggtggca | ccctgcaagt | 1080 |

-continued

```
ggctgcggtg ctcacaggcc ccatccgcag gggtgatcct gtacatcctg ctcgtgggct   1140 acccacccctt ctgggacgag gaccagcaca agctgtacca gcagatcaag gctggtgcct   1200
atgacgtgag tgcaccagcc cctctctgat gagctcccct cctccaggtg tggccgggtg   1260
agggcagcgt gggaagaggc taggagtggg gtgaagccac ctgtggccag gtcctgggtc   1320
ctgctctccc agattcgtgg ctggagatga agcccctttgg agaattcttg ccctgcctg   1380 agagggagct tcaggcccgg ccggggcgct gtttccttct gcagttcccg tccctgagt   1440 gggacaccgt cactcctgaa gccaaaaacc tcatcaacca gatgctgacc atcaaccctg   1500
ccaagcgcat cacagcccat gaggccctga agcacccgtg ggtctgcgtg agtcgccctt   1560
ggtgcccatg gtggggaggg ggctcctggt ggagatggcc tcagaccact cccctggcaa   1620
ggaccccaag agggtcctgt tcctgacatc caagagctcc cttgggtccc ctgggtgctc   1680
cttgtggcct ctggcttggg acataccagc acgtttgtga ggcctgggggc ttggaaggca   1740 ttagagggta gaggtgatcc cttcctccca actgcagtcc tgtctgtgag gggcagagtg   1800
gacgaggcaa gggagagacg agtcttgaag tcccaggcgg gtggggacag acaacccttg   1860
ccgcaatggt ggccggtggc tcttggcaag tggggacccc agggtgccac aagccttgcc   1920
accctggcct ctccctgtg cctcgggctc ggctgccata tgaccaccca tttccccaca   1980
gcaacgctcc acggtagcat ccatgatgca cagacaggag actgtggagt gtctgaaaaa   2040
gttcaatgcc aggagaaagc tcaaggtgag gccctggccc ctagtcccag gcacggccat   2100
gcttctctgt gtccctctgg gctggagcag ggggccttg ggggtctgg gcagacctag   2160 gggttactgc tgcccccaag actgactgtt agcaagtccc agactggatg catcaggtga   2220
actcaggcca gcttgggaat gagtccagag gggccctggg ccaggtgtgg ctcctcctag   2280
ttgtctgtgc cacctcctag cagcccttgg aggagctgtc ctgaagcgct cgctgtgggc   2340
tcctcacccg ggtctgcag gcagcactca ccctctggca gtcacactgt ttagtacaag   2400
caagtccgaa gcttccggct cagacaggtt tggtaaggag agcagagcca cacacactgg   2460
tcttgggtgg gctgggggag ttctgggagg gaggtgggtc ccagtagggt atccaacctg   2520
cctgctttgg tcagggctgg ctccggtgac cgcacactgg cagtccctct acttgtgggt   2580
tccgggatgg ggacttgttg cctgactgcc ctctgctggt ctctgagcag ttctccccgg   2640
aagccccagg actgttgccc tgtctgagcc tgtcaggaaa agaagggct gtcagggagc   2700 tggaccccag aggagctgcc gtggtgacca gctgttctgg tgaccctga ggcttgaggg   2760 gtcttgaagc agctagaagc tgtagttggt caacaggttt aggcccaggg tgtgtgtagt   2820
tctgaaaata ggtgatctgt ctcagtgcgc tgctggctt cctggagctc ttgcctctct   2880
ggaaggctga ggtcatgtca gcctcatgac aatgaggctg agcatctggg caggaggaca   2940
ggggtcttat cctggccaga agccagcagg gaacactgat gggatagccc cggttttatc   3000
tgtgtctctc cccagggagc catcctcacc accatgctgg ccacacggaa tttctcaggt   3060 gagccttttct tctccaggga gacaggcgct gcccctccc tgctggccca cgcaggagag   3120
cgcctccttc ctcaccagcc tctccactcc tcctctgcgg caggcctgcc ctcggcgtct   3180
gccctcagct ctgagaccca ctgcccacct ggccccgctg gctcccacc ttgggtgata   3240 ccacagggtc cagccccccg aggccatcac cttcgtgctg ggtctgtgtc cctccacccc   3300
ctgaacacga gcgtctgtgc tgccccactg gggctcacag catcgtgtgt gtctgtccag   3360
gcgtttgtcg ggcatctatg tggcctcctt gtcattttga gtgctctgaa cattgtgttt   3420
tgtgcgggag gtgggcagaa gggatgcggg gtgatgcggg aggctcgggg gcctccttcc   3480
```

-continued

```
aagttctgga tgagctgcag cctcctgtcc cggctgctca gggtgggtgg ttgggaagca    3540
agttctcttg gcagggggt ggggtctgtt atagacccct gaggcccagg gcgctggcag     3600
acccatcggg gcatgatgtt agccccggag tggagccggc agcccaggtc tggacaagct    3660
gtacctgtgg cttctccgtc gtccgacact ccgtgtgcga gcgtctgtga tccgtctctc    3720
tcgttgtccg tttgcatctg gtgccccca cccgccatcc tgttactttt gctgtgatgc     3780
tgtaatgccg ggaacgcgtg cacacggtca caccaacact aataggactg tcctgtctgc    3840
tgtgtgctca ccacacccctt tgggcatgag aagcccccac tggggttttc taaggagaaa   3900
ggaggcaaat gcttttccgt gtcaatcagt ccaatcttgt tttcactctc ttgagcaaag    3960
gattctggaa ccatctgtca cctaaacttt aactctaatc ttcttctgct tcctttgtct    4020
cttttcttcc cttacctcgc ccacccctcg tctgtgtccg cccaccccctc ccttcccctc   4080 gtctctaacc cggtgctaac agtgggcaga cagaccaccg ctccggccac aatgtccacc    4140
gcggcctccg gcaccaccat ggggctggtg gaacaaggta gatgtgtctc gaccagcgtc    4200
ccgcccgctc ccgcccgtcc ctcctgccag catgcagccc cctgctgcac gcagccgctg    4260
gccgggctcc agagccgccc cagaggccgc caggcccccg ggagcccctg ctccgtgtg    4320 gtcacatccc agcagagccc accacaaggg cagggaggca gccccaagg ctcctcgcct     4380 gtaagaggag gggctgggct aggtggcccc tgggctacac caagcccttc tggtcctggc    4440
ccccgaggtc tggggtccg gagacccca ttaagaatgg cctgggcccc acagggagcc      4500
actgggcctg ctgctggggg gtctgaatcc tgaaaggaga gccttgagga gcagagccag    4560
agaggcagag gcccttgggg cagacacaca ccctgcccct ctggggccgc atggagacgg    4620
tggtctgtgc tgctgagtcc tacacatgca tgtctgccct gagcatcccc ccaggacaag    4680
ccgctctgga gtgggtgagg gttttatgca ccctgaggag actttcaagg cttcctcttg    4740
ggttgtttct gcaaagtcct cctcccctgg cctcaaaccc tgtgagggaa aaggccggca    4800
ctggccacct gctcctctgg gctgtgcggg gccagagccc agaggcccaa gttggcttct    4860
gcccacctgc tggcttgtga ccatgggcag accccatgag ggctaggcga ccccaagacc    4920
tccttgcagc tccagcctga gctgaaggct ggtgagagct tagggcaggc caagctgaca    4980
acgcctggcc acagaacaca gagggctaca ggggtgaccc cagatcctcc ctgggctgag    5040
ctgctgagtt ccctgtcggt gcctccaacg tgggctgggg accggcagga ggttccaggg    5100
tgctggagac tgccttcccc aggcctcctc atgacccaca gggtgagcag cctggccttc    5160
ccagccagag aaccctcctt ctggggaggc ccagggcgtc ctcggggagg gcagtctatt    5220
ctcctcccat gagcccagtg gacgtgtcta gcaggcagca ccccgggaga gccctcccac    5280
gtcttctcca tttgacaggc ctttccagag cgcaggcggg aggggctgt gattagaaaa     5340 gagtgaggct agtggcttct ggggaggcac tgctgcccag gggacagtgc tgagagacag    5400
ctgcctctac gctgccctgt gcccggggct cccgctgcaa tgcccgcctg tctgcaagtg    5460
aacgtggggc gacggtgcat gaggccctgc atgtgtggct ccaccctggg cgccgagagc    5520
agctctgtcc tggagggtgg tcagtgcatg tggacagagc ccagcatggc tgtcctgggt    5580
gaccagctaa ggggacaagg cagaggcagg gctgagagga ccaccatcc tgctaggtca     5640 gcccagctca gccatatcac acggcagtga gcatggagct cagttctctg ccaatggcag    5700
ctgagtctag taccatccag tcagagtctg gtaccagccc atgtggcata gcccctcgg    5760 cccgcagaga gacccccgtct gtcgagtgtg cttcagtttg gcctctgtgg tctctcctgc   5820
```

-continued

| | |
|---|---:|
| attgatcagg tgtaagggca taggagaccc agtgtccggc cagctgcagg gtggcagcag | 5880 |
| ttgccccggc ctggagaccc gggaatgggc agtgccttcc caggatggag ggcagagggt | 5940 |
| ctctccttgt cccacagagg cctgcagaac ccccaaccca ggtgtctgag atgcctgtga | 6000 |
| ctgctccgcc tacccctgggc tcctgcggca cctaacgcat gctttgaact tgagacacag | 6060 |
| aaaggaagtt cccgtgccct tgaatgctag tgtagatggg catcgacagg actctggcca | 6120 |
| cggtgaatct ggagttagtc ccaggcagag atgtgaaatg agcagccccc caaaaaatgg | 6180 |
| ttggccggga gccatgcact caggagggcc gggcccatgc accccacact gcgcccaagg | 6240 |
| cgtgcacaag cgattgtttt aaaagcgggt tcacaaggaa ggatgtttgg gaactgactg | 6300 |
| agacaacagg gacgtctgct gcagggcttc ccagagctct gatggcagcg tcggcctgag | 6360 |
| tccttcgagg agggctggtt tgtacgtggc atttgctgcc cactggactg tgaacttctg | 6420 |
| tcttttattt tcccactgct gctgtggtac atctccagta gcatagtttg gaatgcagg | 6480 |
| ttttgataga ctcaaggatc taaatagaac cctcttagta ccaaggactg tccggggtct | 6540 |
| ctgccagccc cgccgatggg cctaactgtg gtgcctcctt tcctgtgaga atcttctgag | 6600 |
| gacatgcccg gggaaagagc tcagttctgc tgctgcctag ggtgccatgc tggccccggt | 6660 |
| tccaatgcag agcctagctg gaagtaccgc tgggttggcg gaggctacgt gcctgactgt | 6720 |
| cccctcgggg gtggggtgga actagccttc tgaaaccgcc tgcttcagtt ggccacagct | 6780 |
| ttttgaaatg tgtgtttctg gaagggactg ggtcccttcc ttgcctgttc agctccccac | 6840 |
| gacaaatgtc ctcaaggcga ggctggatgc ttccttcctc aggctcctag gaggagcccg | 6900 |
| tcccccagct gtgtcgggca gctggtcacc agcaaggaca ggatccctca gctgcagcct | 6960 |
| caggctggct ggcactgggc gggtgtttct ggatgagtt gtgtgtactg gagatggag | 7020 |
| gggagctgag agggtgggat gcacagacag gagagggac tgtgggggtc ctggaaccct | 7080 |
| gagttccaag tcttcaggac tctccctcca tagcaagtta cagggaagca gatttgagcc | 7140 |
| acagggaagc agatttgagc tgcagcgagg gggagggttt tcagtctgtg ctatagggaa | 7200 |
| gtgggcagtc ggcatttctg gtcctgggaa ctcactgggc agggctgcct tgggacatca | 7260 |
| gggaggtggc gctgtgctca gcttcaccag gagggccttt aggcctgggg acggagagtg | 7320 |
| atgcctgagg cccctctact tctccatgga tcctgggagg gactcctggg ctggatacaa | 7380 |
| aattgttgag agttaagaga tctgtgagga aggggaggct gggaatagaa agtgtgtgcc | 7440 |
| cactgcacat ggggtccgca gggccacgtg cagccactgc gcaggcacaa ccccagtccc | 7500 |
| cacagagccc aggaggggcc agagccatgg aggaggcagc actgggcatt tggacaggga | 7560 |
| gggggtggtc agcaggcagc aggcccaggc ctgtctatgc cctgcgtggt gcagcctcct | 7620 |
| gatctccacg gcaacctgga gcacccagcg tcagaaccac cgggagggct tatggaacag | 7680 |
| atgtccagcc ctgcagaagt tctggctcag gagggcgggg tgggcctggg aatttgcatt | 7740 |
| tctgactgta cagggcgatt ctgctgctgc tgctgctgct ggggttgggg gaggatccca | 7800 |
| tttgagaagc gctgcagtcc taggttgaaa cgtgcctgtc tgtccccacc caggcctgca | 7860 |
| tgggcagcac gggatcccca ggcaggagga cccaatttca tggcctggcc agccagggtc | 7920 |
| ctggagccag gcggtggggg agggatgggg gattgctgtg ccaccttcct tcccggcttg | 7980 |
| gcccgggggc aagcatcctc acacttccca tgtcgtcatc cccttggctc cagcctggct | 8040 |
| gcctctctaa ccctgctgta ccggctggcc gcatggccct ggctcttttt ggtgagcgtg | 8100 |
| gtccaggact ggtgacctgt gagtcctggg cccgcagtct tgcgccctg cccgaaccaa | 8160 |
| cacaaatctt gttttctctc tctctcttcc ttcctcactc cctccccttc tcacctttcc | 8220 |

-continued

```
ttttctgtaa ggtaagctga cttcctcttt tggttttta ttatttta tttttagtt    8280
ctgtaattaa aatcctaaca gccatggagg gtgtgggcac cggggctgg ggccaggccc    8340
ctctgacctc tgagggaa tgctgggtga ggcaggggcc ccgctgctgg gaccaagtat    8400
cctcagggc ttgtgggcag aaaggcctgt gctggcccca gtcagtgcac agaagcggcc    8460
ccaaggccag ggctgctggg cagctcggaa tgagggcgag cagggctgcc cttggtgcct    8520
gagccaagga gccaatggga cagacctctg agcctgggtg ccaagtatga ggtctgagac    8580
agggtgagcg cctgggctgg gacaaggccc tctgagtggg cggccagctg cagcccaccc    8640
accctaccc caggaaggca gggcccggga gggcatgacc tctggggtgc tggctcagct    8700
gccccccaccc caacctgaca ccgctagtcc tgagttccca tcaggagga agcagcatcc    8760
tgccttcctc taggaagagc ttgcatgtgg cccagaagcc aagggggctc cccagcaccc    8820
acgggcatct ctgggtctgg tcagaggaga aatctggatg cttgcaggag ccccagggtc    8880
atggaggagg ctggagacag ggctgtcctg gggtgatggg atggcccccc cacctgctca    8940
gagccagcct gggtgctgga accacacttg cctcaggacc ctgggcttgc tcctggggaa    9000
agagtgggt caggcaaagg ggtgggttg cgctgcagcg agacccaggc ccatcactca    9060
ccataccttc ttcctcccca tgcagcagcc aagagtttac tcaacaagaa agcagatgga    9120
gtcaaggtga ggctccagcc gggccctgtg gtgccgggga gcccagagcc tgcagcttca    9180
cccccacgcc ctgggctcc tgctctggag tcccctccc cccatgccct gagagacacg    9240
ggacagggaa tggcgagtga ggggcttctc ccacctaaga gttcctcttc cctctctcca    9300
cagccccaga cgaatagcac caaaaacagt gcagccgcca ccagccccaa agggacgctt    9360
cctcctgccg ccctggtact gagctcctca aattctgcct ctcagcccct cctacgcccc    9420
tggctgtgtg attgccgctg gtcagagggg gccgggtgaa ggtggggtct ggccccgcct    9480
ggcctgtctg acagcactcg catggcccccc gcccctcatc cctcaccggt ggtgaagtgg    9540
agagaagagg ccactgttgt gggggctcc aattcagaca ggtttaggac tgctctgggg    9600
agcccctggc tgagacccac agatgttggg gtgcaggga gaggcccagc ctcccaccca    9660
tgttgacttg tggatgtctc tccaggagtg ttcaggaagt cagtgaggca gaagataccc    9720
tctccccacc aggaccccac cctcagctcc tccaccatcc tcaacaggcc gacccacaga    9780
ccactccgaa ggtctggctt ggtggggctg ggccaggatc tgcaggggga acagcccata    9840
gtggcacatt ccacggccca tggggagacg gggccacggt ggtgcagtag agaggtgtct    9900
aagccagtgg cagccaaggg gagggcttgc cgtcacctct gtgttccctc agtgctgctc    9960
tgtggctgcc tgagaggcag ggcttagggg ctccctgccg gggaggggag gggtccccac   10020
catgctccgc tccaactgcg cccctcagtg ccccttgccc tgggggctcc tacaggtgaa   10080
ccctatagca gtactcccaa ggatgtaaag ttgtggctgg tgggtgccgg ccttcctgct   10140
ggggcgctgt gctgtgtccc ctcagctgtc ctaagagctt tggggcttgc tggcccgtag   10200
gtccccatat ttgctggaag caggcttggt gtccctgag aacccaggc caggcttcgg   10260
gagccagccc cagaccgccc acgggaatac tgggtttgcc aaatggccac cttgagaccc   10320
aggagaggag agcggtcctg ggaggggcga gctgctcaga gcagccaggc cgtggctgga   10380
gggtggcctg gtgcagccta cctagggcct tccagtggcc agggcagccc acgtgccagc   10440
ctcacagcca gccccatctc ggaccctgtc catcccatgt gccaccgcca cccccatgac   10500
atcttcaaac ctgtgccccc caccacgctg gggcacaggt tcaggcagta aagggtaggg   10560
```

```
agaacccctc aagaccgagc ctggcttctc tggctcccac acacattgtg cagcttgtcg    10620
gggccccaca cggtccatct cccaccctgg acagcagcac ctccgccagc ctggacagag    10680
ctcctgtcca ttccatccct gccggctgac ccaggctcct cccccagctg ctccacgccg    10740
cctccatccc tgtccccac tctgctctgc acttctttct cgcaggctct ggccacccac    10800
acctcctctg tctccctgtt ccctcctgg tggtctccgc ttcctcctct tctcactttc    10860
cctctctttc cttcctctgt gtcttccttc ttctgtagga gcctcaaacc accgtcatcc    10920
ataacccagt ggacgggatt aaggtactgc cccacttttcc tcctcccgct ttccccaggc    10980
aggaggctcc aggccaggag agaggtctgg ggcagcattt gtgccagagt ggagggcaga    11040
tgtcccatgg ccctggccgc ccctccccgc agtacggtag ggccccagtc cgtcttcgtg    11100
ggcaacaaca ggacagactg gctcaggccc caggcgcgcc cctggaggtg cttggcacag    11160
ttgcgcccgg tccccatgtg gccgacactc tcagaccagg gctctgcgtg tcccacctac    11220
ggcaggcagt agggcttcct gaggtctgga gcagggcctg catctcagga gctgcatcct    11280
tggccctcct ggctgtcctc cacccccacct ccctcacgtg gccccagtg cttcctgctg    11340 agcagaccct ccctcctctg ctcccctctc tgctctggcc atcagctccc atcacattgg    11400
catcatcact ctggggccag ggaaggggct ggctctctgg ggtggtggga gggatggggc    11460
cagcagccaa gccatttcca ggacttccaa aacagcgcca ctacacccaa cacggccctc    11520
cagcccagct cccacctagg cctgggctcc ttacagagcc cccagagtgc ctctgtgggg    11580 acccccccact tccttctggc cagtgccacc acccagccca tcatcagaag acatctttct    11640
ccatggcagg gaccaggggg tccaaggggc acccatggtg ctaggcacca gggcctgggc    11700
attcttccca tctggcagct ggggatgggt gccctggga cccgtgtgtg tctggggtgg    11760
gtcatgctct ctgcaggact cctaaacaac cttctgggct gtggtgaact ctgagcctgc    11820
acctaaaaga cctgtagttc tggtctaggg cctccaagca gtgtccaggc agtgtccaga    11880
ccagggggcg gtcccccagg gaccttgtaa gatgtttcct ctgaggagca gagcaggcct    11940 cctgggggacc tggggggatgg tcttttgaag ggcagcagcc ctggagcagg gtgggagagt    12000
ctggggccac ctctgccctc taaggccacc tgagaggtga ggccggggcc tgactggacg    12060
tccagtccca gagggggcagg tgccctgagg gaatgtgggc gacaggaatg ctctgcctgg    12120
ggccaggcca aggttcctgg agccctgtgc ggatctgcag agctcctggg aacgcctcac    12180
cctgtatttt ggatgacacc ggctgctgct tcattggaac cagccagtcc cattgtgttt    12240
tacgtcttgg aatttcaaaa agcccatttt cctctcttgt taaagagtca gctgagcata    12300
ccagtctctc tgccaggctc atcttgctgg gagaagtgga gccctcatgt gttggggatg    12360
cagggtggcc acagcactag ggtggcaggg ccggcctcgg actccgtgcc agcctgtgct    12420
ggctgccgtg agaatgcacc ctggtgaggg gcgccctccc agggaccagc acagaactgg    12480
gtgtcttctc cggtcactgc cgcatgaggt ccacagagct ggggccctgc agccgccaga    12540
gggcatgtcc cctgagcccc tggcctttaa gccccgtgga agcagccgag gcagagatca    12600
gcttcagagc ctgggctggt cctgacacag gcccagccct gtccacctgc cctcagccac    12660
gtcccaccta tccttggccg catcctgacc cgctgcctcc cgtgtttcct caggagtctt    12720
ctgacagtgc caataccacc atagaggatg aagacgctaa aggtacctgc acttgagtcc    12780
ttgccccccc agcggccttg gcattgctgg gttgctcttt gaggtgggtg ggacttgggc    12840
agggtcaact ctcctgcgac gcctagttta tgcatgtgtt gagggctca gggaccctgt    12900 agctgtaatc ctgctccaag cctgggtgtc aggcctgccc agagcggaga agcatggcag    12960
```

```
agatgaccga cagctgggca gtctcggtca ccgcatccaa gtgaggaagc cacggctttg    13020
catggaggca ggttctccac accaggaccc tcacggggaa acaggcccat gggtagaatt    13080
tgttccaaga tgctgtcctt gtcttaaagc tccttaagct tgcgtttctg tccagcatgc    13140
acttgccaag tggccgggca gctgggtgag tgtttccgtg tttgcctttg cttagccagg    13200
agtgtcctgc tgccgtgggt ttctgcacca cagattccag ggcccctcc cttgctcacc     13260 caggccaatg tcttgtgtgt tccccaagag gcccccaggg caccaggcac tgggcatgc     13320 tccatggatt ctgccgcctc cagaccaccc acatggggcc tcctgaccct catcgctcac    13380
acggtcacct aataagcctt atgctgttct cagggctacc ctggtgccca aaagggtca     13440 gccactctgc cagtttaggg gagaaaactt ctcacctgtc caaagcatag ccttgctcct    13500
gcccggccta cccagctatg acactgtccc tgagcagaga tgagcacagg actttgggcc    13560
ctggatgccg gagagtgggt gtttgtgtga ttcccctgca gtctggaaca ggccccaaag    13620
gcaacagcat gaaggctgtc cagaggttct ccatcaccct cagccgagtg gggtgctgag    13680
cagtgaggga ggggacctgg gagggggggcc cagcctggat cctgcagggg agaagagaag   13740
acagccagaa gccagcagct gtggctcaga tctgagcccg agcagcctct cgaggtggag    13800
gcagacaccc cccaccccac cccgtgcaga aagaagcctt gccagcctgc cctgaggctg    13860
gtacagagtc caggcaggct cagtggccat catgccccta cgatgactgt cactccctct    13920
ccgtgcgcct ggcctctgct ggctctggcc aggggtggtc acagcactag ggtggcaggg    13980
tggcctctga ctctgcgcca gcctgcactg gcctgtgctg ccctggcctc tgctggctct    14040
ggctctggca ccgtcccgt gttggctcct tcagccttca catacctgct gcggccacca     14100
caggcccagg accccacag ggtggccacc ccacctccac cccaggagcc ccaggtatcc     14160
agctgtcacc ccctccctcc ctcctggcct cccctgtcc ttctccagtt gccttctttt     14220
cctgcgggcg caccacccac ctgcctgcct cacctgttcc gcctcagccc caggtgtccc    14280
cgacatcctg agctcagtga ggaggggctc gggagcccca gaagccgagg ggcccctgcc    14340
ctgcccatct ccggctccct ttagccccct gccagcccca tgtaagtagc ctgggtcctg    14400
ctgctgtggg ggtcatgttg gagggctggc aaccccctag aggggccact ccagagccga    14460
gggcaggctg agcgtggacc ctggctccag cctcatcacc ccacaatccc tcactggggc    14520
tttccagggt ggccccagcc catcgagccc cacctctttg tgaggagggc cctggaccac    14580
tttcctgctc aaggccactg ggcaggatgg gaggccctgg aggctcgggc ctcaattcca    14640
gtcttcaggg tcggtgcagg cctcactcca cctcagcttg cgggcggggg ggctccctgc    14700
tattgaggca ggctctgatt cagggcctga tcccagggcc caagggggtct agaacacggg   14760 accctcccca ctggcctcct ccgccttgcc gccgcctcgt gtgtctgtct gcctcatgtt    14820
cacgtctcat ctgttccacc ccagccccca gggatctctg acatcctgaa ctctgtgaga    14880 agggggttcag gaaccccaga agccgagggc ccctctcag cggggccccc gccctgcctg    14940
tctccggctc tcctaggccc cctgtcctcc ccgtgtaagt agtggccccc aggcctgccg    15000
cctctgctgc cggacagctc cctgcgaatg gccggcgctc agcagcttcc cacctgcatg    15060
cacggcccag ctaccctgcc ccggcgccgc agcctggagt cctgccctgg cggggcttcc    15120
tgtgggctcc catgctaacc agcagggcag ctcctggctt ctccctaagg ggcccagacc    15180
cctccacggc tcctgctccc actgccactc ccgctcgct gtccagcccc aggcccctct     15240
ccaaaatgtc tgtcccagcc ctgggcagcc ctggcccctc cgaggccccc catgcccta     15300
```

```
ggccctctct gctgatcact gtcccagccc cacagacttc acaccaccc aggggccctg   15360 cccatggtgc ccaggagctg cactcagggc caccctggtt cctgatgtgg ccccaacccc   15420
tgagcaccct ccctcagtct aggaggctga ggaaggtgcc aaaactggaa ccccgaccag   15480
ggtctctgga gctcaccaac aaggggatag tacggagaat cataagcctg cctctgctg    15540 acctgggctg tcctcatggg gccaggccag gcctcctctg taacgcccgt gactccctcc    15600
tctccctgta accccgtcca gcgttcctca agggccactt acctgacagc ttccttgctgg   15660 ccagcagcct ctccctggag ggtgccctct gccccagca gcttcagccc acgccacccg     15720
acagccagag catctgccct tcactcctgc agcctcctct ccacgcacca cgctgtccgc    15780
agcagcaccc tctgtccccc tgtctccctc cgtccccca tatccccctc ggtcagccta     15840
caacctctcc acgtccccct aagtccacgc tctatcccta catccccctc tgtccccaa      15900 attcccctct ttccctcatt tccattttcc tccccaaact ctgctctgcc cctcacattc    15960
tccctctgtc ccccacaccc tcctctgtcc cccacaccct cctgtgtccc ccacaccctc    16020
ctctgtcccc catataccc tctgtccccc acacccacct tggtcccttg cacgcccttt    16080
tctgtccccc acacccctc tgttccctac actctccctc tgtcctccag accctcctct    16140
gtcccccaca ctccctctgt cccccacacc cctgtccccc cacactctcc ctctgccccc    16200
cagaccctcc tctgtcccct acactccctc tgtcccccat atccccctct gtcccccaca    16260
ccctcctctg tcctccaccc cctgcccccc ataccccctt ctgtccccca cacttcctct    16320
gtcttccaca cccctcctg tccccacac ccctctgtc cccagactc tccctctgtc      16380 ccccacactc cgtctgtccc ccacacctc tgtcttccac accccttcct gtccccaca    16440 ccccctctgt ccccatact ctcctctgtc ccccacctcc cctctgttcc ccacaccgct   16500
tctgtccccc acacccctc tgtcttccac ttccctctg tccccacat ccccctctgt     16560 ccctgcacc ctcctctgtc ccctgcaccc tcctctgtcc catgcacctc tctctgtccc     16620
ccacatcccc ctctgtcctc cacactccct ctgtccccca catccacctt ggtcccctca    16680 cgcacccca tccccatga ccccttctgt ccccccacacc cctctgtct tccacacccc     16740 cctctgtccc ccacacccac cttggtcccc tcatgccccc catcccctac accccacttt    16800 tgtccccca catgcccctc tgtccccac gttcccttct gtctcccacg tctcctccat     16860
ttcccgtttc cctctctgtc cccaagctc ccctccatcc ccacatcccc cttctttccc     16920
ctatatcccc tctgtcggcc caggtccacc atcttccccc cacacccccc cattctccct   16980
tcctcccctc tgtccccttg tgcccatcc ccacatctg cctctgtgcc cctcaatctc     17040
tggcttggct gtctgcccat ggtttctctc ctgcgtgccc ccgtgcctg ccttgtgttc     17100 acgtctcgtc tgttccgccc cagccccag gatctctgac atcctgaact ctgtgaggag     17160
gggctcaggg accccagaag ccgagggccc tcgccagtg gggcccccgc cctgcccatc     17220
tccgactatc cctggcccc tgcccacccc atgtaagtag caccttgagt ggccgtggca    17280
gcggctgcct ggaggggctc ggggcgtgcg agcctggcag tggtgctctg ggaagggcca    17340
ttcttgcgga ggagggcggg gcacaggatc cctctgctgg gtcccaggga attgctttga    17400
agcacatgaa ggtgccactg ggtctcagaa aatggaggtt atggttatga agtgtgtatg    17460
acatatgtgt ataggaagag cgtccgaaag agcaggtttg ttgccgaccc cagcattcgc    17520
aaccctgagg tccacagctt tctcctgatg ggaggggaat gggtggcaaa gggtctgcgc    17580
gtgtggcaag ggctagcacg ccaggagctg ctggcttggg tcaaggtgga cctgctgggc    17640
cgggacagaa aagtgtcagt cccggcctga gacgctctag cattagagct gtccaagtcc    17700
```

-continued

```
agacagcagg gagcaggtgg ggatcgggag gcgcggatct ggggggcagc tggggccagg    17760
ctgaaacaga gcgggcggga caggaagcac aggctgggca gcctcccgg ccagggagga     17820 gccaggctgg gccacctccc ggtctgtctg ccgactaccc gcagtatcac ttacagggat    17880
ggatgacatc ccagggctgc tgccaccccc acctgtgggg agacaccaga ctggggtgg     17940 tgtggagata ctcttagaga agaggctgct gggccacggg ctcggcatgg cagggcagtg    18000
gctaggtaag tacttgaggg acaggtgggg tctgcttgcc accgtccct ctgcaggctg     18060 ggcctggggg ctgctgcagg cggccagggc agaagggtgt ggggagagtg aacccacagg    18120
agcagcggct cgaggagggg gatgcaggct gcaggctcaa aggggcactg gatccaccct    18180
gggtgcccga gagagcaggg ggcagcccct ggaggggtac tcaccccag agcttctgtg     18240 gtcggctgag acccccagc aggggttgac tgagggatc agaggcaagc agctgagggg      18300
agaggccagg ttcttgatgc tgatagggtc ggggtgcctg ggcgaccaga actcaaggag    18360
ggaggcatgg ggagggccg ccgtgcagct gggtgggtg caccgcagag cctctgggag      18420
tggtcagaac ccccgacacc tgccacttct acagcagctc atctgattt aaggggcttg     18480 ctgcccttgc agaagtggag gggtgtgccc aaaggagcct gcctggaagg tcaccccatc    18540
aggttggcat gaccccagcc caggactgca gcctgccctc aagtctgtg cagtatctgg     18600 ggtgagtcct ctgaggacag ggcccagggt gggtgtggag tggccagctc ggggctcggt    18660
gtccaggctc accttcaggg gccacagcac agacctgccc ttccagagtc ttccctgagc    18720
ttggctgggg aggagggggc tgcaggaagg agctgtgagc agggcaggat ggagattcgt    18780
gtggccctcc tgggaggggc tgggcagggc tgggaaaggg gtgggtgaga tgttccggaa    18840
ctcagggaaa ggaagagtct gggtactgcc ctgggggcac ctgggcccag gtggcaggtg    18900
gccagctttc tgcctccttt ccacctcctt tctccagaag gcacccacca gctgtgtaaa    18960
tagggcaggt gcccacggcc cgcctcaggc cccgtctcct ccccacccac gctctctaat    19020
cgcggattat acacaatcca gcctgatccc tgggcagctg ccctccctcc cgcagccacc    19080
tctggctctg agagatgggc ttggggccag cctgggtcc caggagtcca ggccaggatg     19140
agaacctgct ctgaccccac ctggacgcat taggcctgcc tggacctgtt gcctcacccc    19200
aagagagcca caggcaatgc aaaggctcct gttcatgtca gggcacctgg aaggcctgac    19260
ttgcagaggc tcttggctcg tgcagacccc tccaagccca ggccctgccc accacctccc    19320 cttttgtctct ggaactgcca ggacagcttg tcctcagcca gcaggtttcc cgacccgggc   19380
acctcttcat gttgggcccc cctccttttcc ctccatcagg gatcatgccc ttcttcaggg   19440
gcctggatat caaggacaca aaagctccca tgtgctatgt ggggaggcag agtggggct    19500 gggttgagct ggggtctggg cagcgccatt ccgcagggca gggcagcct aggcttccca     19560 tctgtggaat gggtgggtgg gtctcacaac ggacctgctt cccgtacttc agcacggtta    19620
ccactcttga ttggaactct gaccatgcat ctcctcttct gtttacttca cgctttctct    19680
tcccatcaac tccatttta attacaattt gtttaaaagc actgcatatt acttcattaa     19740
acagaagatt agtttcactt accattagtg taaggtgact atagaaccaa agcagactgg    19800
aaaccaaatg acataatgtc attctcttct ccattccagc tgcctgctgc tgtgcgcctg    19860 agaaccctg tggagtggga ggggcagctg tctctgtaca ttagaaaggg aggttaacta     19920
agtgacagga ggtgtttggg acatgtggac accagacttc tctcttgatg caaggaggc     19980 agagccaggc agcctagtgg gggctggctt ggggggctgct ggaaggactg gctacaggtg   20040
```

```
gaagagaggt cagacctgaa gcttggggcc acctccagga aaggacaggt gaaagtggag    20100
gcatgaggca ggggagaggc aggtgccagg cagagggtgg agaggaggca ggaacatagc    20160
agctggggcg ggggcggggcc ctcaagtgtc atatgctact ttcctgggggc ccaggggcaa   20220
ggacaggaac agccacagca tgtgttggga cagagccctg tgccttccta gagctgggca    20280
ggtggaatgg ggcaggaatg ggactcgtgg tggctgcagc aggaactgga ggggaagggg    20340
cttctggatc ctgcagccta ccttcctaga ggccagcttt ccggggtcca ccaggtgggt    20400
gggaactggg cttgtgtagc aagactgccc tgaggaccat ccatgacatg gtctagatga    20460
aagttaggaa agaaagggag acaagctggc agcagaagta cagctgggtc aggagcaagg    20520
gcctttccag atagggacaa cccaagagtg cacatgtgcc cacgccacac aacacaggca    20580
cacacgacac gtgcacgctc ataggcactg cacacacaca tgcacaggtg ctcatgcata    20640
tgtatgagct tcatctacac acattcacat gccgtcctgc ttatgtgcat gtttccatac    20700
atgcacatga atgcacaatc acgtgtacac acatgcatgt gatcacatac atgaacatgt    20760
gtgcacccca ctcctcaggt gccatcgggc tcctcctgct gtcactgtgc agcaggggac    20820
atgaggcccc agagcagaca ggtgcagcac aggcgttccc aggcagtgcc ccacacacat    20880
gcatgagcac acccgggcat gtggcgcctc ctttgtggac tcagtccacc tgccaggtgg    20940
gctccctggt ggtgtgagct cccagaggtc tggcgagaga gataaaggca accccaccac    21000
caggcgtgct gagaattccc tcttctggct gggcacagtg gctcatacct gtaatcccag    21060
cactttggga ggccgaggtg ggcagatcac ttgaggttag gagtttgaga ccagcctggc    21120
caatatggtg aaacctcatc tccactaaaa atatacacac acaaaaatta gctgggtgtg    21180
gtggtgtgca cctgtagttc cagctactcg ggaggctgag gcaggagaat cgcttgaacc    21240
tgggagtcag agactgcagt gagccgagat catgtcactg cactccagcc cgggtgacag    21300
agtgagactc catctaaaaa aaaaaagaa ttccctcctc tgggaattta gaccacagac    21360
aggttgcatg tatgtggccg ttggaggcag cactcacagc aaagagtgga aacgtcacca    21420
cagggcctgc cttctggtga aaatggtgtc ctgcagggcg ggcagctgtt tgagggcagg    21480
tgtcccaggt gcggcctgca gcagcctgag ggtcacagag cgcagtgctg ggagtgcaga    21540
gacttccccc acagggagag ttcccaggaa cctgcttccg gtgcacttct gggggtttga    21600
gttttttcca cggacgaatt actttgagaa accactgtta ctcgtgtgta taggtgagcg    21660
tgcgtgtgca tgtgtgttct gtgtgtgagt gtgcatgtat gtgcgtgcct gcgtatatat    21720
cctcgcagat acggctaggg acctcactca ggacagtagt tctgcctgag gagagtgaat    21780
gcggcaagat tgaggagaac acaggcatct tcaaactaca tgtgcggtgc tttatttctt    21840
taaaaatgcg tctaaagcaa ataggaaaat gttaagattt gaatccgtag agtgtgggtt    21900
ctattattct ctccacatct tccatacgtt taaaatcttt tgcaatgaaa ataagctgta    21960
gttaaagcag caatgcaggc tgccagtgag cgccccggag gccagtgagg accagcatgg    22020
ctgggtggcc tgttggaatc aaggggggc gggcaggagc tgcaggcagg cgcccgggag    22080
tagcccgggc atgggggtgc ggggcaacag ggatgtctgc aggggtagca tgtgggcccc    22140
ggactgcaag caggtggagc cagccggatg cggctcctat gagaaaagcg gggaacaaga    22200
gaccacgctc gttcttcctg ctgcgggggac agccctggtc atcgctccgg ggaaccctgc    22260
agcctgcgcc gcacgtggcc gcccctgct gcttcctcct cccgggcctc cgggtggcct    22320
tgctgacggc tccttctctg aggcaggtct ctgccttctc gcctggtgcc tgcactcagt    22380
agccccctca ccagagctgc tgggtgaagg aagcactaag aacccaaggc tcgggaggag    22440
```

```
agtgggccg ggaagctgca gggaagcgca gggccaggcc tggtgggccc aggggctggc   22500
tcacgggagg gcaggaggga gactgtggcg gacagcacgt ggggccagga ggtgacctcc   22560
aagtggattg tgggtgggtt ttttgtcctc tttctgcatt ttccaggcat tttgtaatgt   22620
ggatagaata tttctgttct tcaaaaatac tttagttaag aaaataaga tggaagctgt    22680 tgcacttgaa aatgaggaag ccactggtga tgcaggggg gcggcggaga ggacctcttc    22740
tgcaaatagc ggcaggaaca cggcatggat gcagctcgcg ctcccccagg ccctcccctg   22800
ggctgtgtgg aggggtccgg ggggaatggg ccagcgccca gtggtcacct ggccatgtct   22860
ccccacagcc cggaagcagg agatcattaa gaccacggag cagctcatcg aggccgtcaa   22920
caacggtgac tttgaggcct acgcgtgagt ccctggggct gggggggggc tgtgcaggac   22980
aaggatgtgg gacccttggg ggggcctgct cagagtcagg ggtccacggg gcccctcctc   23040
acttggattt ggcccccagg aaaatctgtg acccagggct gacctcgttt gagcctgaag   23100
cactgggcaa cctggttgaa gggatggact tccacagatt ctacttcgag aaccgtgagt   23160
gaggaagccc gggtgggcat gaggggggcgg tgccccagg agagcctctc ggcccctccc   23220
agggacagca tggtggctgc ctatggaagc cctgtcccct ctgtgcccag ggttggccag   23280
ccacctctcc cccgccagag gccataccca gcccccagaa tcccactctt ggaggggccc   23340
atgctgctcc caggagagcc gagcctcccc aataagggga gttgagagag ggaaaggatt   23400
aggctggtgg ggtggaagac gggcaccagg gcagtcatgg taacccgaga cccccgcccc   23460
gcctgctgtc cacagtgctg gccaagaaca gcaagccgat ccacacgacc atcctgaacc   23520
cacacgtgca cgtcattgga gaggatgccg cctgcatcgc ttacatccgg ctcacgcagt   23580
acattgacgg gcagggccgg ccccgcacca gccagtctga ggagacccgc gtgtggcacc   23640
gccgcgacgg caagtggcag aacgtgcact ccactgctc gggcgcgcct gtggccccgc    23700
tgcagtgaag gtgagtgttc tgtgctaagt gacagctggg gcagagggt ggcggtggtg    23760 tgagtggctg cagcctgggg aggcgatggg gagcggtggg gcctgtggca gagcccatgc   23820
ctgggaagtc cctgagcttt cctggtgagg ccacaggaat gatgtcaaat tagggaccac   23880
ggcaggctgg gtgtggcagg cctccccaga ggactgggga gctggtgagg gcctgagcag   23940
tccacactgg ccagagctgg gtgggttgca ggtggatggg ccccgggcag cacagtcctg   24000
ggcaccatgc cctgttttgtg aggactgtta gagccccaga tgggcgttcc ccaggtggtg   24060
ggtgcagcgg gcccagagcc cagttttaca gggatagtag taattgggtt gggcaccttg   24120
aacctctctc ccgagtgggc cctttttctgg actttaaccc tctctgcagt gccgcatggc   24180
agacagcaga gcctgggggt ggatgggaga ggggctgct gaggagctga cccacccgcc    24240
ccatttcaga gctgcgccct ggtttcgccg gacagagttg gtgtttggag cccgactgcc   24300
ctcgggcaca cggcctgcct gtcgcatgtt tgtgtctgcc tcgttccctc ccctggtgcc   24360
tgtgtctgca gaaaacaag accagatgtg atttgttaaa aaaaaaaaa aaaaaaaa      24420 aaaaacaag atgacgacga caaccacaaa aaaattgac atcagatgaa atgaaaaaaa     24480 aaaaaacaa aaaaaactaa aggaaggaaa aagctgtaaa aatcactggc attcgtgggg   24540
ccactcccca cccaagctcc acgtgtgtcc gtctgtgctc ctggcctctg ggaccagc     24600 tgggacatga acttgtctgc caggcccccg tcgcgtgctg aacggtgtta gtttgtaggt   24660
aacgcacaca ccccacacct aaggtgtctg catcctcctg ccaacgcatg ggctccacgt   24720
ggtgtgctcg ctggctgtcg tgactgtcag ctgtctcttg ggagggggctg tgggggcccg  24780
```

| | | | | |
|---|---|---|---|---|
| ctgggctgcc | tcctttcccg | ctagttgtgc | ctgagagttg | ctgttgttcc tgctttccct | 24840 |
| tcccttcctt | tcatcccctg | aagggctagg | tgtgggtttt | ccgtgccgg tatccccaca | 24900 |
| cacccagcac | ggacaaccct | tcggcagagc | ccaggccggc | ccctcacccc ctggagtatt | 24960 |
| gaaactggag | tcccgtcccc | aaggccttca | gagatgcccc | tacacaccca gggctccagc | 25020 |
| tctggtcctt | ctgggggagt | aaagtgcaaa | gaggggcaca | gcttagtttt gggcctctcg | 25080 |
| ccgagcaaga | gacagcactg | ctggctacag | ctccaacaca | gccagctgtg caagaggac | 25140 |
| tctgcctggg | ctgccccccc | tcctgtgtga | ggtgtctgtc | ccttctctgc tggccagcag | 25200 |
| cagatgcact | ggcagctccc | aaccctgttt | ccgcccctcg | gccctccccc agcctgttcg | 25260 |
| gcttctctgc | agcccgcaag | ggggagcaga | cttttgacaa | aggactgcgg gcctcgctca | 25320 |
| agtccctgag | cccccagctg | aagctgggag | gggaggccag | gctttgtgtc tgggcatatt | 25380 |
| cgtctgctga | tggggtttgg | ggaagcctgg | ggcttggggt | ttggtcgggt ggtgcagcta | 25440 |
| gtggcagagc | gggatcagag | gtggtggctg | cccagcttct | gggctgagac aagggtctgt | 25500 |
| gcaggggttt | actgaagtgg | gagtgccttt | ggaatctggg | ccgggagcag aagggagcaa | 25560 |
| aagctacagt | gggagccagc | ctagggcaca | tgggaggcgt | gagggcagtg ctgcccgtgc | 25620 |
| agtgtcaggt | gtgccagtgc | cttggcgggc | tgcagtgcgt | gtgagggcac cttctaggtg | 25680 |
| ggccagggat | gcagctatgg | agataaggcg | ggctggggac | agaaacaggt gggcacaggg | 25740 |
| cccaggacac | cagcggatgg | agggcagggt | ctagccctgt | gctcctgagc gtcggctgcc | 25800 |
| tgggttcgag | gcggtgggtc | cccggcccct | tgtgatggtg | tgtaccatgg gggagctcgg | 25860 |
| ggacagggca | agcccgagca | tggtgggggct | gcagggtggg | tctgaagcca ggttgggtgg | 25920 |
| gggtggtcac | aagccctgac | tgcagagggt | caggggctcc | tgccccagtg cctgcccact | 25980 |
| ttcaattcac | attgttttca | acaaggattt | tctttatctt | ccctacaaa tcaagccaag | 26040 |
| ggaggggcac | agaatgggga | acaggacaca | ggatcctaaa | ctccaagggg actgtccacc | 26100 |
| gatgaacact | cagagtggac | accatcttcc | gtccacgctg | tgcccaggac agctgtcccc | 26160 |
| atccatgaac | acagggtaaa | catctgccgg | gctccgcacc | agtggctccc tgggccatgg | 26220 |
| gacagcggca | gggctcacca | cggacagcac | gtgggcccagc | agccggccac cctggcgtcc | 26280 |
| tggggcctcc | tcccctcctc | tccctctcac | cttgtcacct | ccacggagct gcctgtctgg | 26340 |
| gataatttgg | ggattttttt | tctgggggat | aattcttttg | catgacccct aaagagcaag | 26400 |
| ccacaccggt | ctgctagcta | ggtgtccgcg | gtgtggtggt | ggcggccgct ggccagcgct | 26460 |
| gcaaggggtc | ggctgcccac | ggtgctggct | ggcctcccct | cctctctctt tttgctgagt | 26520 |
| ttcattgtct | tttcttttctg | agccttgtaa | gtgtacaaaa | attattctta ttttgttctg | 26580 |
| tctcgggaaa | ctgcaaataa | agaaaaaca | ggacaaactg | cttcaagtgc agctgggtgc | 26640 |
| tttagctgga | atcctgccga | cctcctgcgc | caaaatacag | actcaagccc ggtccctggc | 26700 |
| caagacccta | cttgggcccc | tcctccaatg | aaaggtagtg | ctatgggagc cctgagctgg | 26760 |
| ccctgacagt | cctgagcccc | tctagggtga | acggctcacc | ccaggtaggg cactagtcat | 26820 |
| agatcatagc | tctaccagct | gtctccacct | cttcctctgg | tcctctgaag tcttctgggc | 26880 |
| ccagcgctgt | ccaccctgaa | tgctggaact | gaaactggat | cccagccccc aacacccctg | 26940 |
| acctctccat | tcacccccgg | tggccgctaa | ggatgtggcc | agggcagcct ctgggcagga | 27000 |
| aggagcccca | ggaccaagac | ctctggctgt | cctgctgttt | ccttccgccc ctgctacatg | 27060 |
| tattggctat | tctggatgct | gaggacacac | agtgaccaca | gagccgggct ccaccccagt | 27120 |
| ggattatgca | gacagatggc | acgcaggcct | gtgtggacat | cagcctcggg caccagacat | 27180 |

```
aggcaaggcg caaggtgata cagtaggcag ccaccatggg ggccaggagg ctccagcaga   27240
ggccacacaa ccagcccaga atccaggaca gagagctgga atggagacag gaagccaga    27300 taccaggcca gactggccag gtgctacagg cctgtgggcc aggccaggct tggggacttc   27360
gtcctgggtg tgaaggagac aggcacccct gaggccttcc ctctgcatct ccagcccaag   27420
ctaagcgcaa actcttaggt tggagtaagg agtaaccccc tgccaagttt ctcctgtcct   27480
caggctccac ccaccaccta tgctgcctgg ccccatgggg cacacgctca ggcccagcct   27540
gggaaagcaa ctgcacctgc ctgtgctatg ctggcccttc tcagcctcaa tgccctcctc   27600
cctccccgac gcaccctcgt ggccccgct gggcccctg atgcaccctc atgtctccat      27660
ggcaacctgc tcagagtgtg gccctgccct tggctcccct ccacacctgt gtcccaggca   27720
gtgccacggc actttcctaa acagaaggat gggcttcaaa acagtcccag acactaaaca   27780
cacctgcatt ttgggtccaa gtaacttctg acaagacgag tgccctaca caccctcagt     27840 cctatccact atgggcaagg agcctgaagg atccccccaga actggctaaa gccctcagtc  27900
tcctcctcca ccctgagcac cttcacgcgc agagtggcc ctggatgtca gcttcttgct     27960
ccccatggtc tgcacctgga caggtgctct caggtgtgtg ggtgggcagg tggcaggtcc   28020
caagagccag gtgcaaagaa tctaggccag tgcccacgtg tgctgcagtg tctgtcccca   28080
gcatggtatc tagggctcca cttgcctatc agctgtaatc ggaggaggct ttccaggcca   28140
ggcctccccc aggaaggctg caggcactgc ggatcgtgcg ccctcacatg cattattcct    28200
gaggcccttc tgcagatgcc atcagggcag caactctgat gaggtattag ggcacagcac   28260
acagggctaa gccaccctgt actgggccaa gcgctacagg caaaaaggac accaccgacg    28320
ggcatttcat tcatcgcttt tattttata tatttttgag agggagcctc actctgtcgc     28380
ccaggctgga gtgcagtggc gcgatcttgg ctcactgcaa cttctccctc ctgggttc     28438

<210> SEQ ID NO 4
<211> LENGTH: 542
<212> TYPE: PRT
<213> ORGANISM: Human

<400> SEQUENCE: 4

Met Ala Thr Thr Val Thr Cys Thr Arg Phe Thr Asp Glu Tyr Gln Leu
  1               5                  10                  15

Tyr Glu Asp Ile Gly Lys Gly Ala Phe Ser Val Val Arg Arg Cys Val
                 20                  25                  30

Lys Leu Cys Thr Gly His Glu Tyr Ala Ala Lys Ile Ile Asn Thr Lys
             35                  40                  45

Lys Leu Ser Ala Arg Asp His Gln Lys Leu Glu Arg Glu Ala Arg Ile
         50                  55                  60

Cys Arg Leu Leu Lys His Ser Asn Ile Val Arg Leu His Asp Ser Ile
 65                  70                  75                  80

Ser Glu Glu Gly Phe His Tyr Leu Val Phe Asp Leu Val Thr Gly Gly
                 85                  90                  95

Glu Leu Phe Glu Asp Ile Val Ala Arg Glu Tyr Tyr Ser Glu Ala Asp
                100                 105                 110

Ala Ser His Cys Ile Gln Gln Ile Leu Glu Ala Val Leu His Cys His
            115                 120                 125

Gln Met Gly Val Val His Arg Asp Leu Lys Pro Glu Asn Leu Leu Leu
        130                 135                 140

Ala Ser Lys Cys Lys Gly Ala Ala Val Lys Leu Ala Asp Phe Gly Leu
```

-continued

```
145                 150                 155                 160
Ala Ile Glu Val Gln Gly Asp Gln Ala Trp Phe Gly Phe Ala Gly
                165                 170                 175

Thr Pro Gly Tyr Leu Ser Pro Glu Val Leu Arg Lys Glu Ala Tyr Gly
                180                 185                 190

Lys Pro Val Asp Ile Trp Ala Cys Gly Val Ile Leu Tyr Ile Leu Leu
                195                 200                 205

Val Gly Tyr Pro Pro Phe Trp Asp Glu Asp Gln His Lys Leu Tyr Gln
                210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala His Glu Ala Leu Lys His Pro Trp Val
                260                 265                 270

Cys Gln Arg Ser Thr Val Ala Ser Met Met His Arg Gln Glu Thr Val
                275                 280                 285

Glu Cys Leu Lys Lys Phe Asn Ala Arg Arg Lys Leu Lys Gly Ala Ile
                290                 295                 300

Leu Thr Thr Met Leu Ala Thr Arg Asn Phe Ser Val Gly Arg Gln Thr
305                 310                 315                 320

Thr Ala Pro Ala Thr Met Ser Thr Ala Ala Ser Gly Thr Thr Met Gly
                325                 330                 335

Leu Val Glu Gln Ala Lys Ser Leu Leu Asn Lys Lys Ala Asp Gly Val
                340                 345                 350

Lys Pro Gln Thr Asn Ser Thr Lys Asn Ser Ala Ala Ala Thr Ser Pro
                355                 360                 365

Lys Gly Thr Leu Pro Pro Ala Ala Leu Glu Pro Gln Thr Thr Val Ile
                370                 375                 380

His Asn Pro Val Asp Gly Ile Lys Glu Ser Ser Asp Ser Ala Asn Thr
385                 390                 395                 400

Thr Ile Glu Asp Glu Asp Ala Lys Ala Arg Lys Gln Glu Ile Ile Lys
                405                 410                 415

Thr Thr Glu Gln Leu Ile Glu Ala Val Asn Asn Gly Asp Phe Glu Ala
                420                 425                 430

Tyr Ala Lys Ile Cys Asp Pro Gly Leu Thr Ser Phe Glu Pro Glu Ala
                435                 440                 445

Leu Gly Asn Leu Val Glu Gly Met Asp Phe His Arg Phe Tyr Phe Glu
                450                 455                 460

Asn Leu Leu Ala Lys Asn Ser Lys Pro Ile His Thr Thr Ile Leu Asn
465                 470                 475                 480

Pro His Val His Val Ile Gly Glu Asp Ala Ala Cys Ile Ala Tyr Ile
                485                 490                 495

Arg Leu Thr Gln Tyr Ile Asp Gly Gln Gly Arg Pro Arg Thr Ser Gln
                500                 505                 510

Ser Glu Glu Thr Arg Val Trp His Arg Arg Asp Gly Lys Trp Gln Asn
                515                 520                 525

Val His Phe His Cys Ser Gly Ala Pro Val Ala Pro Leu Gln
                530                 535                 540
```